(12) United States Patent
Al-awar et al.

(10) Patent No.: US 11,850,287 B2
(45) Date of Patent: Dec. 26, 2023

(54) HETEROCYCLIC ACYL HYDRAZONE LINKERS, METHODS AND USES THEREOF

(71) Applicant: Ontario Institute for Cancer Research (OICR), Toronto (CA)

(72) Inventors: Rima Al-awar, Toronto (CA); Ahmed Mamai, Mississauga (CA)

(73) Assignee: ONTARIO INSTITUTE FOR CANCER SEARCH (OICR), Toronto (CA)

( * ) Notice: Subject to any disclaimer, the term of this patent is extended or adjusted under 35 U.S.C. 154(b) by 271 days.

(21) Appl. No.: 16/956,021

(22) PCT Filed: Dec. 20, 2018

(86) PCT No.: PCT/CA2018/051638
§ 371 (c)(1),
(2) Date: Jun. 19, 2020

(87) PCT Pub. No.: WO2019/119141
PCT Pub. Date: Jun. 27, 2019

(65) Prior Publication Data
US 2021/0106694 A1    Apr. 15, 2021

Related U.S. Application Data

(60) Provisional application No. 62/609,495, filed on Dec. 22, 2017.

(51) Int. Cl.
*C07D 498/18*      (2006.01)
*C07D 215/42*      (2006.01)
(Continued)

(52) U.S. Cl.
CPC .......... *A61K 47/6889* (2017.08); *A61K 38/07* (2013.01); *A61K 45/06* (2013.01);
(Continued)

(58) Field of Classification Search
CPC .. C07D 498/18; C07D 215/42; C07D 223/16; C07D 311/68; C07D 335/06; A61K 47/68; A61P 35/00
See application file for complete search history.

(56) References Cited

U.S. PATENT DOCUMENTS

| | | |
|---|---|---|
| 2005/0009751 A1 | 1/2005 | Senter et al. |
| 2007/0197455 A1 | 8/2007 | Moran et al. |
| 2009/0076076 A1 | 3/2009 | Siles et al. |

FOREIGN PATENT DOCUMENTS

| | | |
|---|---|---|
| CA | 2977032 A1 | 1/2014 |
| CA | 2642273 C | 9/2016 |

(Continued)

OTHER PUBLICATIONS

Arbuzov et al. (Zhurnal Obshchei Khimii (1952), 22, 1645-7). Abstarct.*

(Continued)

*Primary Examiner* — Bruck Kifle
(74) *Attorney, Agent, or Firm* — Bereskin & Parr LLP/S.E.N.C.R.L., s.r.l.; Shuo Xing

(57) ABSTRACT

The present application is directed to compounds of Formula (I): compounds of Formula (II): compounds of Formula (III): and compounds of Formula (IV): compositions comprising these compounds and their uses, for example as medicaments and/or diagnostics. Specifically claimed are: (1) compounds containing reactive functional groups (compound of formula I), compounds containing compounds to be linked together (compound of formula II) and compounds having a reactive functional group/a compound to be linked (compound of formula IV), (2) an antibody-drug conjugate (compound of formula III), wherein the antibody is covalently attached by a linker to one or more drugs, (3) pharmaceutical compositions comprising compounds of Formula (II) or Formula (III), (4) treatment/diagnosis of disease comprising compounds of Formula (II) or Formula (III), and (5) methods of preparing an ADC of Formula III.

(I)

(II)

(III)

(Continued)

-continued

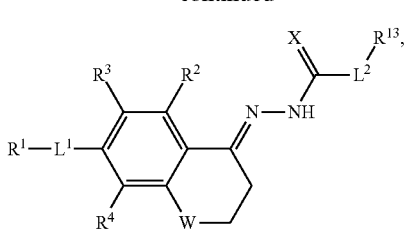
(IV)

19 Claims, 2 Drawing Sheets

(51) Int. Cl.
C07D 223/16 (2006.01)
C07D 311/68 (2006.01)
C07D 335/06 (2006.01)
A61K 47/68 (2017.01)
A61P 35/00 (2006.01)
A61K 38/07 (2006.01)
A61K 45/06 (2006.01)

(52) U.S. Cl.
CPC ...... A61K 47/6811 (2017.08); A61K 47/6855 (2017.08); A61P 35/00 (2018.01); C07D 215/42 (2013.01); C07D 223/16 (2013.01); C07D 311/68 (2013.01); C07D 335/06 (2013.01); C07D 498/18 (2013.01)

(56) References Cited

FOREIGN PATENT DOCUMENTS

| CA | 2987322 A1 | 2/2017 |
|---|---|---|
| CA | 2891280 C | 3/2018 |
| CN | 101434595 A | 5/2009 |
| CN | 103739589 A | 4/2014 |
| CN | 105985265 A | 10/2016 |
| DE | 102005060813 A1 | 6/2007 |
| WO | 2002096910 A1 | 12/2002 |
| WO | 2005005378 A1 | 1/2005 |
| WO | 2011019882 A1 | 2/2011 |
| WO | 2014031784 A1 | 2/2014 |
| WO | 2014068443 A1 | 5/2014 |
| WO | 2016196280 A1 | 12/2016 |
| WO | WO 2016/196280 | * 12/2016 |
| WO | 2017004519 A1 | 1/2017 |
| WO | 2018175622 A | 9/2018 |
| WO | 2019109188 A1 | 6/2019 |
| WO | 2020248065 A1 | 12/2020 |

OTHER PUBLICATIONS

Naylor et al. (Journal of the Chemical Society (1958) 1190-3). Abstract.*
International Search Report and Written Opinion for WO2019119141 dated Mar. 21, 2019.
European Search Report of corresponding EP application No. EP 18891218 dated Nov. 30, 2021.
Doronina, S. O.; Toki, B. E.; Torgov, M. Y.; Mendelsohn, B. A.; Cerveny, C. G.; Chace, D. F.; DeBlanc, R. L.; Gearing, R. P.; Bovee, T. D.; Siegall, C. B.; Francisco, J. A.; Wahl, A. F.; Meyer, D. L.; Senter, P. D. Development of potent monoclonal antibody auristatin conjugates for cancer therapy, Nat. Biotechnol. 2003, 21, 778-784.
Widdison, W. C.; Wilhelm, S. D.; Cavanagh, E. E.; Whiteman, K. R.; Leece, B. A.; Kovtun, Y.; Goldmacher, V. S.; Xie, H.; Steeves, R. M.; Lutz, R. J.; Zhao, R.; Wang, L.; Blattler, W. A.; Chari, R. V. Semisynthetic maytansine analogues for the targeted treatment of cancer, J. Med. Chem. 2006, 49, 4392-4408.
Bulter, T. et al., "Chemoenymatic Synthesis of Biotinylated Nucleotide Sugars as Substrates for Glycosyltransferases", ChemBioChem., Nov. 26, 2001, vol. 2(12), pp. 884-894.
Song, J. et al., "Small-molecule inhibitors of cathespin L incorporating functionalized ring-fused molecular frameworks". Bioorganic & Medicinal Chemistry Letters, vol. 23, 2013, pp. 2801-2807.
International Search Report and Written Opinion of corresponding PCT/CA2018/051638 dated Mar. 21, 2019.
Song et al., "Synthesis and Biochemical Evaluation of Thiochromanone Thiosemicarbazone Analogues as Inhibitors of Cathepsin L", ACS Medicinal Chemistry Letters, vol. 3, 2012, pp. 450-453.
Song et al., "Synthesis and Antifungal Activity of Some Thiazole Derivatives", Asian Journal of Chemistry, vol. 25, 2013, pp. 1849-1852.
Wang G, "Preparation of carboxamide compounds as antiviral agents for the treatment of paramoxyvirus viral infections", vol. 160, 2014, pp. 1-3.
Hamann, P. R.; Hinman, L. M.; Hollander, I.; Beyer, C. F.; Lindh, D.; Holcomb, R.; Hallett, W.; Tsou, H. R.; Upeslacis, J.; Shochat, D.; Mountain, A.; Flowers, D. A.; Bernstein, I. Gemtuzumab ozogamicin, a potent and selective anti-CD33 antibody-calicheamicin conjugate for treatment of acute myeloid leukemia, Bioconjug. Chem. 2002, 13, 47-58.
Bennett Celsa and Jane Andres, USPTO, "Making a Prima Facie Case (e.g. In Polymorph Cases)", Jun. 12, 2013.
Ducry, L.; Stump, B. Antibody-drug conjugates: linking cytotoxic payloads to monoclonal antibodies, Bioconjug. Chem. 2010, 21, 5-13.
Casi, G.; Neri, D. Antibody-drug conjugates: basic concepts, examples and future perspectives, J. Control. Release 2012, 161, 422-428.
Adair, J. R.; Howard, P. W.; Hartley, J. A.; Williams, D. G.; Chester, K. A. Antibody-drug conjugates—a perfect synergy, Expert Opin. Biol. Ther. 2012, 12, 1191-1206.
Carter, P. J. Potent antibody therapeutics by design, Nat. Rev. Immunol. 2006, 6, 343-357.
Doronina, S. O.; Toki, B. E.; Torgov, M.; Mendelsohn, B. A.; Cerveny, C. G.; Chace, D. F.; DeBlanc, R. L.; Gearing, R. P.; Bovee, T. D.; Siegall, C. B.; Francisco, J. A.; Wahl, A. F.; Meyer, D. L.; Senter, P. D. Development of potent monoclonal antibody auristatin conjugates for cancer therapy, Nat. Biotechnol. 2003, 21, 778-784.
Widdison, W. C.; Wilhelm, S. D.; Cavanagh, E. E.; Whiteman, K. R.; Leece, B. A.; Kovtun, Y.; Goldmacher, V. S.; Xie, H.; Steves, R. M.; Lutz, R. J.; Zhao, R.; Wang, L.; Blattler, W. A.; Chari, R. V. Semisynthetic maytansine analogues for the targeted treatment of cancer, J. Med. Chem. 2006, 49, 4392-4408.
Doronina, S. O.; Mendelsohn, B. A.; Bovee, T. D.; Cerveny, C. G.; Alley, S. C.; Meyer, D. L.; Oflazoglu, E.; Toki, B. E.; Sanderson, R. J.; Zabinski, R. F.; Wahl, A. F.; Senter, P. D. Enhanced activity of monomethylauristatin F through monoclonal antibody delivery: effects of linker technology on efficacy and toxicity, Bioconjug. Chem. 2006, 17, 114-124.
Dosio, F.; Brusa, P.; Cattel, L. Immunotoxins and Anticancer Drug Conjugate Assemblies: The Role of the Linkage between Components, Toxins (Basel) 2011, 3, 848-883.
Wu, A. M.; Senter, P. D. Arming antibodies: prospects and challenges for immunoconjugates, Nat. Biotechnol. 2005, 23, 1137-1146.
Arbuzov et al. Zhurnal Obshchei Khimii (1952), 22, 1645-7.
Hamann, P. R.; Hinman, L. M.; Beyer, C. F.; Lindh, D.; Upeslacis, J.; Flowers, D. A.; Bernstein, I. An anti-CD33 antibody-calicheamicin conjugate for treatment of acute myeloid leukemia. Choice of linker, Bioconjug. Chem. 2002, 13, 40-46.
van Der Velden, V. H.; te Marvelde, J. G.; Hoogeveen, P. G.; Bernstein, I. D.; Houtsmuller, A. B.; Berger, M. S.; van Dongen, J. J. Targeting of the CD33-calicheamicin immunoconjugate Mylotarg (CMA-676) in acute myeloid leukemia: in vivo and in vitro saturation and internalization by leukemic and normal myeloid cells, Blood 2001, 97, 3197-3204.
Kovtun, Y. V.; Audette, C. A.; Ye, Y.; Xie, H.; Ruberti, M. F.; Phinney, S. J.; Leece, B. A.; Chittenden, T.; Blattler, W. A.;

(56) References Cited

OTHER PUBLICATIONS

Goldmacher, V. S. Antibody-drug conjugates designed to eradicate tumors with homogeneous and heterogeneous expression of the target antigen, Cancer Res. 2006, 66, 3214-3221.

Dascalu, A.E et al., "Design, Synthesis and Evaluation of Hydrazine and Acyl Hydrazone", Boorganic & Medicinal Chemistry Letters, Apr. 28, 2020, vol. 30, pp. 1-4.

Alley, S. C. et al., "Antibody-drug conjugates: targeted drug delivery for cancer", Curr. Opin. Chem. Biol. 2010, 14, 529-537.

Hartley, J. A. et al., "The development of pyrrolobenzodiazepines as antitumour agents", Expert Opin. Investig. Drugs 2011, 20, 733-744.

Soraires Santacruz Maria C et al. "Synthesis, antiviral evaluation and molecular docking studies of N-aryl substituted/unsubstituted thiosemicarbazones derived from 1-indanones as potent anti-bovine viral diarrhea virus agents", Biooorganic & Medicinal Chemistry, Elseveir, Amsterdam, NL, vol. 25, No. 15, May 27, 2017, pp. 4055-4063.

Hutter, M. L. et al., "Gemtuzumab ozogamicin in non-acute promyelocytic acute myeloid leukemia", Expert Opin. Biol. Ther. 2011, 11, 1369-1380.

Siegel, M.M. et al., Calicheamicin Derivatives Conjugated to Monoclonal Antibodies: Determination of Loading Values and Distributions by Infrared and UV Matrix-Assisted Laser Desorption/Ionization Mass Spectrometry and Electrospray Ionization Mass Spectrometry, Anal. Chem, Jul. 15, 1997, vol. 69(14), pp. 2716-2726.

Howard, P.W., Antibody-drug Conjugates (ADCs), Protein Therapeutics, Aug. 14, 2017, Ed. 1, Chapter 9, pp. 271-309.

Chang, M. et al., "Smart Linkers in Polymer-drug Conjugates for Tumor-targeted Delivery", Journal of Drug Targeting, Nov. 11, 2015, vol. 24(6), pp. 475-491.

Toki, B. E.; Cerveny, C. G.; Wahl, A. F.; Senter, P. D. Protease-mediated fragmentation of p-amidobenzyl ethers: a new strategy for the activation of anticancer prodrugs, J. Org. Chem. 2002, 67, 1866-1872.

Naylor et al. Journal of Chemical Society (1958) 1190-3.

Khongorzul et al. "Antibody-Drug Conjugates: a Comprehensive Review", Mol Cancer Res; 18(1) Jan. 2020, 3-19.

"Michael addition reaction", Wikipedia, Jul. 9, 2023, pp. 1-8, https://en.wikipedia.org/wiki/Michael_addition_reaction.

"Aldehyde", Wikipedia, Jan. 1, 2023, pp. 1-8, https:/en.wikipedia.org/wiki/Aldehyde.

* cited by examiner

HETEROCYCLIC ACYL HYDRAZONE LINKERS, METHODS AND USES THEREOF

CROSS-REFERENCE TO RELATED APPLICATIONS

This application is a National Stage of co-pending International Application No. PCT/CA2018/051638 filed on Dec. 20, 2018 which claims the benefit of priority from co-pending U.S. Provisional Patent Application Ser. No. 62/609,495, filed on Dec. 22, 2017, the contents of each of which are incorporated herein by reference in their entirety.

FIELD

The present application relates to novel linker groups, to processes for their preparation, and for their use to link two chemical entities together, as well as to linked compounds comprising the linker groups and compositions comprising these linked compounds and to their use for example in the treatment or diagnosis of diseases and conditions, including, but not limited to, cancer.

BACKGROUND

Chemotherapy, which targets rapidly dividing cancer cells, has proven to be one of the primary weapons in the arsenal to fight cancer. However, this approach is limited by the fact that it also affects healthy cells, typically resulting in moderate to severe side effects.[1-2] Targeted therapies have the potential to greatly enhance the state of cancer therapeutics by selectively targeting cancerous cells while not harming healthy cells.[3-7] Biologics such as monoclonal antibodies have emerged as options for cancer therapy due to their inherent specificity for cancer associated targets and their potential to have fewer off-target effects.[8-10] In addition to carrying out the immune modulating functions of antibodies,[11] monoclonal antibodies have been used as a means of delivering cytotoxic drugs to cancer cells with high specificity, giving way to a type of therapeutics known as antibody-drug conjugates (ADC).[12-16] ADCs have gained significant attention as a means of targeted delivery of cytotoxic agents to cancer cells. ADCs consist of a cytotoxic drug chemically attached to an antibody through a linker, and upon target cell binding and internalization, the drug is released. While this idea has limitless potential, its application is limited by the variable in vivo stability of the linker, which may lead to lower efficacy and higher off-target effects.

ADCs (FIG. 1) contain three distinct entities: (1) an antibody designed to target a tumor-associated antigen,[17-18] (2) cytotoxic drugs,[19-21] and (3) linkers that connect the drugs to the antibody.[22-23] It is desirable that the ADC be stable, but upon antibody binding to the target cell and internalization, the drug is ideally released from the antibody to exert its actions.[16] The efficacy and toxicity of ADCs depend heavily on the linker between the drug and the antibody and is affected by several factors, including, for example, stability in plasma, drug to antibody ratio (DAR) and conjugation sites.[24] Currently, over 60 ADCs are in clinical trials, with 4 clinically approved. Adcetris™ (Brentuximab vedotin) targeting CD30 for anaplastic large cell lymphoma and Hodgkin lymphoma was approved in 2011. Kadcyla™ (Trastuzumab emtansine) was approved in 2013 for Her2+ metastatic breast cancer. Mylotarg™ (Gemtuzumab ozogamicin) targeting CD33 for acute myeloid leukemia, was withdrawn from the market in 2010 due to excessive toxicity, but was re-approved in 2017 under a different dosing regimen. Besponsa (Inotuzumab ozogamicin) was approved for the treatment of refractory acute lymphoblastic leukemia.[27-28]

There are currently two major classes of linkers used in ADCs: cleavable linkers such as acyl hydrazones,[12,27,37-38] disulfides,[20,39-42] and peptides,[22,43-46] and non-cleavable linkers.[22,40-41] ADCs with acyl hydrazones as linkers are cleaved by the acidic environments of the lysosome. Disulfides and peptidic linkers are cleaved in thiol rich environments and by lysosomal peptidases but may have reduced potency, in part due to a greater difficulty of cleavage.[37,47] Noncleavable linkers will only break apart upon proteolytic degradation of the antibody post-internalization. While this linkage is very stable, internalization is essential, which may reduce its range of targets.[48] Taken together it is clear that the structure of the linker has a great impact on the stability, efficacy and safety of ADCs.

SUMMARY

The present application relates to the design and optimization of novel heterocyclic acyl hydrazone linkers. Different substitution patterns have been identified that allow for modulation and tuning of conjugate stability in different media mimicking biological environments.

Known clinical or marketed ADCs possess diverse linkers that have a wide range of intracellular cleavage rates. Ranging from the intracellularly readily cleavable linkers such as the acyl hydrazones to the relatively stable non-cleavable linkers, having the ability to tune the rate of release of the payload and to improve plasma stability provides opportunities not only to target a greater variety of diseased cells, but also to design agents tailored to achieve a better therapeutic window. Towards the goal of developing enhanced control of ADC linker stability, several model heterocyclic acyl hydrazones whose lability is modulated either by steric or stereoelectronic effects have been prepared. Starting with the acyl hydrazone structure (A) present in Mylotarg the adjacent steric and electronic environments were varied and the half-life tested in a simulated lysosomal environment (pH 4.5) and in human plasma.

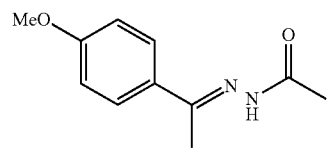

A

When the imine carbon atom of the linker group is part of a heterocyclic structure containing, for example, an oxygen atom (as in the compounds of the application), about a 7-fold increase in half-life was observed compared to A. Incorporation of a fluoro group ortho to the acyl hydrazone provided a half-life to a similar range as A. On the other hand, incorporation of a fluoro group in the meta position rendered the heterocyclic hydrazone even more stable with about 9 fold increase in half-life. Comparisons were also made with the corresponding carbocyclic linkers, with heterocyclic linkers providing about 2 times the half-life of their corresponding carbocyclic partner. In addition, model compound A showed a moderate stability when incubated in human plasma with 37% remaining at the end of the assay. When the imine carbon is part of a ring containing a heteroatom, the plasma stability improved considerably. These results suggest that the adjacent steric and electronic environment can affect the stability of acyl hydrazones. Analogues of the model linkers have been incorporated into actual linker molecules as described in greater detail herein below.

Therefore, in one aspect, the present application includes a compound of Formula (I) or a pharmaceutically acceptable salt and/or solvate thereof:

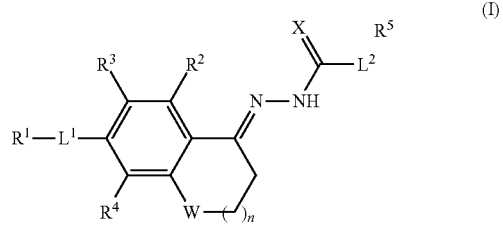

$R^1$ and $R^5$ are independently a reactive functional group;

$R^2$ is selected from H, halo, $C_{1-6}$-alkyl, $C_{1-6}$fluoroalkyl, $OR^6$, $SR^6$ and $NR^6R^7$;

$R^3$ and $R^4$ are independently selected from H, CN, $NO_2$, halo, $C_{1-6}$-alkyl, $C_{1-6}$fluoroalkyl, OR, $SR^8$ and $NR^8R^9$;

X is selected from O, S and $NR^{10}$;

W is selected from O, $NR^{11}$, S, S(O) and $S(O)_2$;

$R^6$, $R^7$, $R^8$, $R^9$, $R^{10}$ and $R^{11}$ are independently selected from H, $C_{1-6}$alkyl and $C_{1-6}$fluoroalkyl;

$L^1$ and $L^2$ are independently a linker moiety; and n is 0, 1, 2 or 3.

In another aspect, the present application includes a compound of Formula (II) or a pharmaceutically acceptable salt and/or solvate thereof:

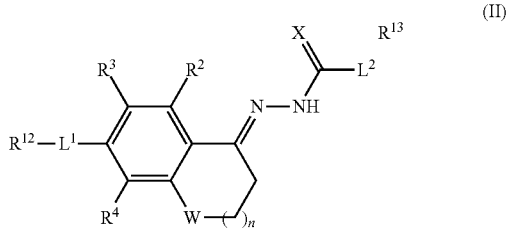

wherein:

$R^{12}$ and $R^{13}$ are different and are selected from compounds to be linked together; and $L^1$, $L^2$, $R^2$, $R^3$, $R^4$, X, W and n are as defined above.

In some embodiments, the compounds to be linked together are selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex and solid support In a further aspect, the present application includes an antibody-drug conjugate comprising an antibody covalently attached by a linker to one or more drugs, the conjugate having a Formula (III):

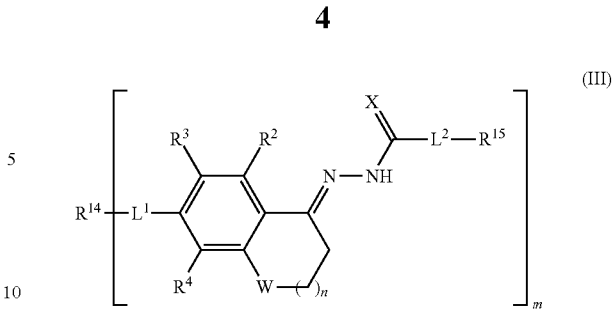

or a pharmaceutically acceptable salt and/or solvate thereof, wherein $R^{14}$ is an antibody;

$R^{15}$ is a drug;

$L^1$, $L^2$, W, $R^2$, $R^3$, $R^4$ and n are as defined as above; and m is an integer from 1 to 20.

In a further aspect, the present application includes a compound of Formula IV or a pharmaceutically acceptable salt and/or solvate thereof

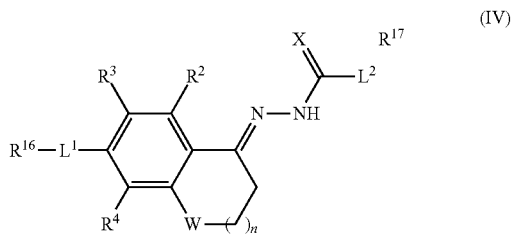

wherein one of $R^{16}$ and $R^{17}$ is a reactive functional group and the other of $R^{16}$ and $R^{17}$ is a compound to be linked to another different or same compound; and $L^1$, $L^2$, $R^2$, $R^3$, $R^4$, X, W and n are as defined above.

The present application includes a composition comprising one or more compounds of the application and a carrier. In an embodiment, the composition is a pharmaceutical composition comprising one or more compounds of Formula II or III and a pharmaceutically acceptable carrier.

The present application also includes a method of treating and/or diagnosing one or more diseases, disorders or conditions by administering an effective amount of one or more compounds of Formula (II) or (III), or a pharmaceutically acceptable salt and/or solvate thereof, to a subject in need thereof. In an embodiment of the present application, the disease, disorder or condition is cancer.

In another aspect, the present application includes a method of synthesizing one or more compounds of Formula (II), (III) or (IV) as defined above, or a pharmaceutically acceptable salt and/or solvate thereof, wherein the method comprises reacting one or more compounds of Formula (I) as defined above with a first compound, for example, selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex or solid support, and then a second, different compound, for example, selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex and solid support.

In another aspect the present application includes a method of preparing an ADC of Formula (III) comprising:
   (a) reacting a compound of Formula (I) with a drug to provide a Formula (I)-drug conjugate;
   (b) reacting the Formula (I)-drug conjugate with an antibody to provide the ADC of Formula (III); and optionally
   (c) purifying the ADC of Formula (III).

In another aspect, the present application includes a method of preparing an ADC of Formula (III) comprising:
   (a) reacting a compound of Formula (IV) as defined above with an antibody to provide the ADC of Formula (III); and optionally
   (b) purifying the ADC of Formula (III).

In another aspect of the present application is a use of one or more compounds Formula (II) or (III), as defined above, or a pharmaceutically acceptable salt and/or solvate thereof, as a medicament and/or a diagnostic agent.

In another aspect of the present application is a use of one or more compounds Formula (I) or (IV), as defined above, or a pharmaceutically acceptable salt and/or solvate thereof, for preparing an antibody-drug conjugate.

The novel acyl hydrazone linkers of this present application have been demonstrated in an exemplary embodiment as linkers for ADCs. Therefore, compounds of Formula (II) and (III) may be useful for treating diseases, disorders or conditions treatable by ADCs. In a further aspect, the present application includes a method of administering an antibody or a drug to a subject comprising administering a compound of Formula (II) or (III), or a pharmaceutically acceptable salt and/or solvate thereof, to the subject.

In a further aspect of the application there is provided a use of one or more compounds of Formula (II) and (III) as defined above, or a pharmaceutically acceptable salt and/or solvate thereof, to treat and/or diagnose cancer.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which.

DETAILED DESCRIPTION

1. Definitions

Figure 1:
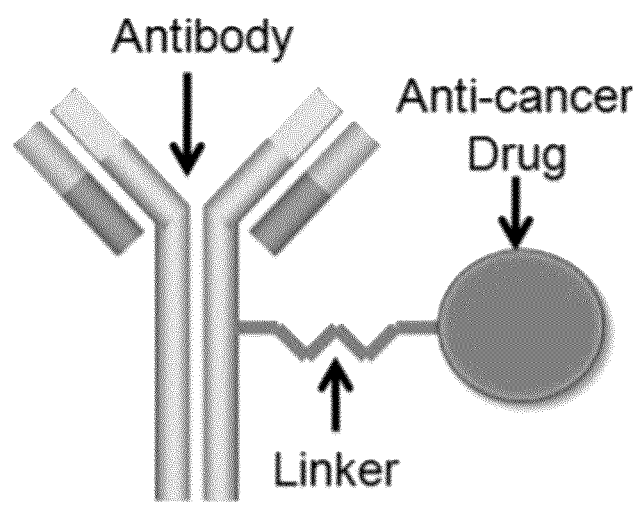
FIG. 1 is a schematic showing the general structure of an antibody-drug conjugate.

Unless otherwise indicated, the definitions and embodiments described in this and other sections are intended to be applicable to all embodiments and aspects of the present application herein described for which they are suitable as would be understood by a person skilled in the art.

The term "compound(s) of the application" or "compound(s) of the present application" and the like as used herein refers to a compound of Formula (I), (II), (III) or (IV), or salts and/or solvates thereof.

The term "composition(s) of the application" or "composition(s) of the present application" and the like as used herein refers to a composition comprising one or more compounds of the application and a carrier.

The term "and/or" as used herein means that the listed items are present, or used, individually or in combination. In effect, this term means that "at least one of" or "one or more" of the listed items is used or present. The term "and/or" with respect to salts and/or solvates thereof means that the compounds of the application exist as individual salts or hydrates, as well as a combination of, for example, a salt of a solvate of a compound of the application, or a solvate of a salt of a compound of the application.

As used in the present application, the singular forms "a", "an" and "the" include plural references unless the content clearly dictates otherwise. For example, an embodiment including "a compound" should be understood to present certain aspects with one compound or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

In embodiments of the present application, the compounds described herein may have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having alternate stereochemistry. It is intended that any optical isomers, as separated, pure or partially purified optical isomers are racemic mixtures thereof are included within the scope of the present application.

The compounds of the present application may also exist in different tautomeric forms and it is intended that any tautomeric forms which the compounds form, as well as mixtures thereof, are included within the scope of the present application.

The compounds of the present application may exist as mixtures of E and Z isomers or cis and trans isomers and it is intended that any above mentioned isomer, as well as mixtures thereof, are included within the scope of the present application.

The compounds of the present application may further exist in varying polymorphic forms and it is contemplated that any polymorphs, or mixtures thereof, which form are included within the scope of the present application.

The compounds of the present application may further be radiolabeled and accordingly all radiolabeled versions of the compounds of the application are included within the scope of the present application.

The compounds of the present application also include those in which one or more hydrogen atoms are replaced with deuterium.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

The present description refers to a number of chemical terms and abbreviations used by those skilled in the art. Nevertheless, definitions of selected terms are provided for clarity and consistency.

The term "linker moiety" as used herein refers to any molecular structure that joins two or more other molecular structures together.

The term "small molecule" as used herein refers to a molecule having a low molecular weight and with a size, for example, on the order of about 10 nm.

The term "reactive functional group" as used herein refers to a group of atoms or a single atom that will react with another group of atoms or a single atom (so called "complementary functional group") to form a chemical interaction between the two groups or atoms.

The term "chemical interaction" as used herein refers to the formation of either a covalent or ionic bond between the reactive functional groups. The chemical interaction is one that is strong enough to append the acyl hydrazone linkers of the present application to compounds to be linked together.

The term "reacts with" as used herein generally means that there is a flow of electrons or a transfer of electrostatic charge resulting in the formation of a chemical interaction.

The term "conjugating" as used herein means to bind two molecules together via a chemical interaction.

The term "binding moiety" as used herein refers to any moiety that binds to a receptor or active site in a biological molecule. In an embodiment, the binding is specific binding, that is, the binding moiety will bind to one receptor or active site preferentially over other receptors or active sites.

The term "labelling agent" as used herein refers to any agent that is used for detection of molecules. Different types of labelling agents are known in the art depending on the form of detection to be used. For example, the labelling agent is selected from a radiolabel, a fluorescent label, a spin label, isotope label, a positron emission topography (PET) and a single-photon emission computer tomography label.

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-6}$alkyl means an alkyl group having 1, 2, 3, 4, 5 or 6 carbon atoms. All alkyl groups are optionally fluorosubstituted unless otherwise indicated.

The term "alkylene" as used herein, whether it is used alone or as part of another group, means a straight or branched chain, saturated alkylene group, that is, a saturated carbon chain that contains substituents on two of its ends. The number of carbon atoms that are possible in the referenced alkylene group are indicated by the prefix "$C_{n1-n2}$". For example, the term $C_{1-10}$alkylene means an alkylene group having 1, 2, 3, 4, 5, 6, 7, 8, 9 or 10 carbon atoms. All alkylene groups are optionally fluorosubstituted.

The term "alkenylene" as used herein, whether it is used alone or as part of another group, means a straight or branched chain, unsaturated alkylene group, that is, an unsaturated carbon chain that contains substituents on two of its ends and at least one double bond. The number of carbon atoms that are possible in the referenced alkenylene group are indicated by the prefix "$C_{n1-n2}$". For example, the term $C_{2-6}$alkenylene means an alkenylene group having 2, 3, 4, 5 or 6 carbon atoms. All alkenylene groups are optionally fluorosubstituted, unless otherwise indicated.

The term "alkynylene" as used herein, whether it is used alone or as part of another group, means a straight or branched chain, unsaturated alkylene group, that is, an unsaturated carbon chain that contains substituents on two of its ends and at least one triple bond. The number of carbon atoms that are possible in the referenced alkynylene group are indicated by the prefix "$C_{n1-n2}$". For example, the term $C_{2-6}$alkynylene means an alkynylene group having 2, 3, 4, 5 or 6 carbon atoms. All alkynylene groups are optionally fluorosubstituted, unless otherwise indicated.

The term "optionally substituted" refers to groups, structures, or molecules that are either unsubstituted or are substituted with one or more substituents.

The term "fluorosubstituted" refers to the substitution of one or more, including all, hydrogens in a referenced group with fluorine.

The term "halo" or "halogen" as used herein, whether it is used along or as part of another group, refers to a halogen atom and includes fluoro, chloro, bromo and iodo.

The term "cell" as used herein refers to a single cell or a plurality of cells and includes a cell either in a cell culture or in a subject.

The term "subject" as used herein includes all members of the animal kingdom including mammals, and suitably refers to humans. Thus the methods of the present application are applicable to both human therapy and veterinary applications.

The term "pharmaceutically acceptable" means compatible with the treatment of subjects, for example humans.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with the treatment of subjects.

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. In an embodiment, the mono- or di-acid salts are formed, and such salts exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

A base addition salt suitable for, or compatible with the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide as well as ammonia. Illustrative organic bases which form suitable salts include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. [See, for example, S. M. Berge, et al., "Pharmaceutical Salts," *J. Pharm. Sci.* 1977, 66, 1-19]. The selection of the appropriate salt may be useful, for example, so that an ester functionality, if any, elsewhere in a compound is not hydrolyzed. The selection criteria for the appropriate salt will be known to one skilled in the art. Other non-pharmaceutically acceptable salts may be used, for example in the isolation of compounds of the application for laboratory use, or for subsequent conversion to a pharmaceutically acceptable base addition salt The term "solvate" as used herein means a compound, or a salt of a compound, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

The term "atm" as used herein refers to atmosphere.

The term "MS" as used herein refers to mass spectrometry.

The term "aq." As used herein refers to aqueous.

DCM as used herein refers to dichloromethane.

DIPEA as used herein refers to N,N-diisopropyl ethylamine

DMF as used herein refers to dimethylformamide.

THE as used herein refers to tetrahydrofuran.

DMSO as used herein refers to dimethylsulfoxide.

EtOAc as used herein refers to ethyl acetate.

MeOH as used herein refers to methanol.

MeCN as used herein refers to acetonitrile.

HCl as used herein refers to hydrochloric acid.

TFA as used herein refers to trifluoroacetic acid.

CV as used herein refers to column volume.

Hex as used herein refers to hexanes.

PBS as used herein refers to phosphate-based buffer.

MW as used herein refers to molecular weight.

HPLC as used herein refers to high performance liquid chromatography.

LCMS as used herein refers to liquid chromatography-mass spectrometry.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3$^{rd}$ Edition, 1999 and in Kocienski, P. Protecting Groups, 3$^{rd}$ Edition, 2003, Georg Thieme Verlag (The Americas).

The term "treating" or "treatment" as used herein and as is well understood in the art, means an approach for obtaining beneficial or desired results, including clinical results. In some embodiments, beneficial or desired clinical results may include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" may also mean prolonging survival as compared to expected survival if not receiving treatment. "Treating" and "treatment" as used herein may also include prophylactic treatment. For example, a subject with early cancer may be treated to prevent progression, or alternatively a subject in remission may be treated to prevent recurrence. Treatment methods comprise administering to a subject a therapeutically effective amount of one or more of the compounds and optionally consist of a single administration, or alternatively comprise a series of administrations. For example, compounds may be administered at least once a week. However, in another embodiment, the compounds may be administered to the subject from about one time per two weeks, three weeks or one month. In another embodiment, the compounds may be administered about one time per week to about once daily. In another embodiment, the compounds may be administered 2, 3, 4, 5 or 6 times daily. The length of the treatment period depends on a variety of factors, such as the severity of the disease, disorder or condition, the age of the subject, the concentration and/or the activity of the compounds, and/or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration is required. For example, the compounds may be administered to the subject in an amount and for duration sufficient to treat the subject.

As used herein, the term "effective amount" or "therapeutically effective amount" means an amount of one or more compounds that is effective, at dosages and for periods of time necessary to achieve the desired result. For example in the context of a treatment for a disease, disorder of condition, an effective amount is an amount that, for example, increases said treatment compared to the treatment without administration of the one or more compounds. In an embodiment, effective amounts vary according to factors such as the disease state, age, sex and/or weight of the subject. In a further embodiment, the amount of a given compound or compounds that will correspond to an effective amount will vary depending upon factors, such as the given drug(s) or compound(s), the pharmaceutical formulation, the route of administration, the type of condition, disease or disorder, the identity of the subject being treated, and the like, but can nevertheless be routinely determined by one skilled in the art.

The term "administered" as used herein means administration of a therapeutically effective amount of one or more compounds or compositions to a cell, tissue, organ or subject.

The term "neoplastic disorder" as used herein refers to a disease, disorder or condition characterized by cells that have the capacity for autonomous growth or replication, e.g., an abnormal state or condition characterized by proliferative cell growth. The term "neoplasm" as used herein refers to a mass of tissue resulting from the abnormal growth and/or division of cells in a subject having a neoplastic disorder. Neoplasms can be benign (such as uterine fibroids and melanocytic nevi), potentially malignant (such as carcinoma in situ) or malignant (i.e. cancer). Exemplary neoplastic disorders include the so-called solid tumours and liquid tumours, including but not limited to carcinoma, sarcoma, metastatic disorders (e.g., tumors arising from the prostate), hematopoietic neoplastic disorders, (e.g., leukemias, lymphomas, myeloma and other malignant plasma cell disorders), metastatic tumors and other cancers.

The term "cancer" as used herein refers to cellular-proliferative disease states.

The term "antibody" as used herein refers to a full-length antibody molecule or an immunologically active portion of a full-length antibody molecule, i.e., a molecule that contains an antigen binding site that immunospecifically binds antigen of a target of interest or part thereof, such targets including but not limited to, cancer cells that produce specific identifiable antigens. The term "antibody" also refers to monoclonal antibodies, polyclonal antibodies, multispecific antibodies (e.g., bispecific antibodies), and antibody fragments. Antibodies may be murine, human humanized, chimeric, or derived from other species.

The term "monoclonal antibody" as used herein refers to an antibody obtained from a population of substantially homogenous antibodies, i.e., the individual antibodies comprising the population are identical except for possible naturally occurring mutations that may be present in minor amounts. Monoclonal antibodies are highly specific, being directed towards a single antigenic site. In contrast to polyclonal antibody preparations which include different antibodies directed against different determinants (epitopes), each monoclonal antibody is directed against a single determinant on the antigen. In addition to their specificity, the monoclonal antibodies are advantageous as they can be synthesized uncontaminated by other antibodies. The modifier "monoclonal" indicates the character of the antibody as being obtained from a substantially homogenous population of antibodies, and is not to be construed as requiring production of the antibody by any particular method.

The term "ErbB" as used herein is a receptor protein tyrosine kinase which belongs to the ErbB receptor family responsible for mediating cell growth, differentiation and survival. The ErbB receptor family includes four distinct members including epidermal growth factor receptor (EGFR, ErbB1, HER1), HER2 (ErbB2 or p185$^{neu}$), HER3 (ErbB3) and HER4 (ErbB4 or tyro2).

The terms "epidermal growth factor receptor" or "EGFR", includes naturally occurring and mutant forms thereof (e.g., a deletion mutant EGFR).

The term "ErbB-expressing cancer" is a cancer characterized by comprising cells which have ErbB protein present at least at their cell surface. In an embodiment, the ErbB protein is the EGFR protein which is produced at sufficient levels at the surface of the cells such that an anti-EGFR antibody can bind thereto and have a therapeutic and/or diagnostic effect with respect to the cancer.

A "chemotherapeutic agent" or "anticancer agent" are terms that refer to a chemical compound useful in the treatment of a neoplastic disorder or cancer.

The term "drug" as used herein, is intended to refer to any compound or mixture of compounds which is capable of exerting an effective or useful pharmacological effect.

The term DM1 as used herein refers to a compound of the formula

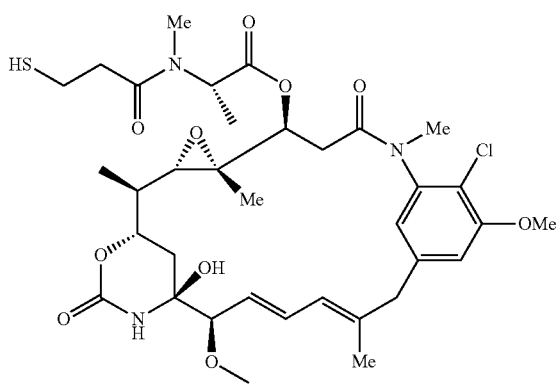 [SMILES: COc1cc2cc(c1Cl)N(C)C(=O)C[C@H](OC(=O)[C@H](C)N(C)C(=O)CCS)[C@]1(C)O[C@H]1[C@H](C)[C@@H]1C[C@@](O)(NC(=O)O1)[C@H](OC)/C=C/C=C(\C)C2]

including pharmaceutically acceptable salts and/or solvate thereof. DM1 is also known as mertansine, and in some of its forms, emtansine.

The term "MMAE" or "monomethyl auristatin E" as used herein refers to a compound of the formula

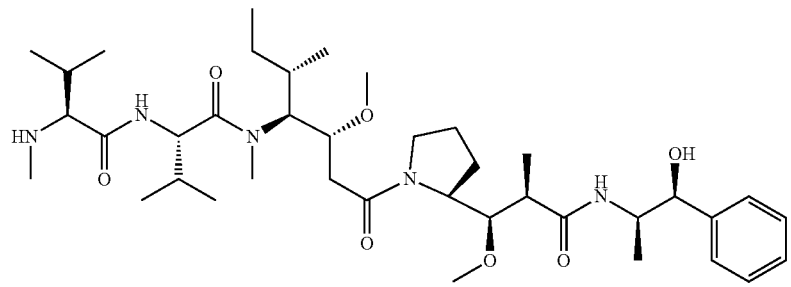 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

including pharmaceutically acceptable salts and/or solvates thereof.

II. Compounds of the Application

The present application includes the design and optimization of acyl hydrazone linkers that can generally be used with a wide variety of molecular classes and tolerate many different functional groups.

Accordingly, the present application includes a compound of Formula (I) or a pharmaceutically acceptable salt and/or solvate thereof:

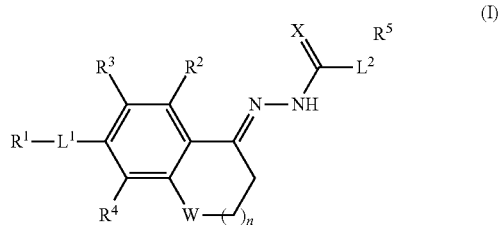

wherein:
$R^1$ and $R^5$ are independently a reactive functional group;
$R^2$ is selected from H, halo, $C_{1-6}$-alkyl, $C_{1-6}$-fluoroalkyl, $OR^6$, $SR^6$ and $NR^6R^7$;
$R^3$ and $R^4$ are independently selected from H, CN, $NO_2$, halo, $C_{1-6}$-alkyl, $C_{1-6}$fluoroalkyl, $OR^8$, $SR^8$ and $NR^8R^9$;

X is selected from O, S and $NR^{10}$;
W is selected from O, $NR^{11}$, S, S(O) and $S(O)_2$;
$R^6$, $R^7$, $R^8$, $R^9$, $R^{10}$ and $R^{11}$ are independently selected from H, $C_{1-6}$alkyl and $C_{1-6}$fluoroalkyl;
$L^1$ and $L^2$ are independently a linker moiety; and
n is 0, 1, 2 or 3.

In some embodiments, $L^1$ and $L^2$ independently comprise at least one ester, carbonate, carbamate or amide linkage although a person skilled in the art would appreciate that other linker moieties, such as ethers, sulfones, sulfoxides, thioethers, thioamides, thioesters and/or amines can additionally, or alternatively, be present. In some embodiments, $L^1$ and $L^2$ independently also comprise one or more $C_1$-$C_{20}$alkylene groups, $C_2$-$C_{20}$alkenylene groups and/or $C_2$-$C_{20}$alkynylene groups.

In some embodiments, $L^1$ and $L^2$ are independently selected from a direct bond, Z, $R^a$, Z—$R^a$, $R^a$—Z, $R^a$—Z—$R^b$ and Z—$R^a$—$Z^a$, wherein Z and $Z^a$ are independently selected from O, S, S(O), $SO_2$, NH, N($C_{1-6}$-alkyl), C(Q), C(Q)Y, YC(Q), YC(Q)$Y^a$, (Y$C_{1-6}$-alkylene)$_p$, ($C_{1-6}$alkyleneY)$_p$ and Y—($C_{1-6}$alkyleneY)$_p$, wherein $R^a$ and $R^b$ are independently selected from $C_{1-10}$alkylene, $C_{2-10}$alkenylene and $C_{2-10}$alkynylene; Q, Y and $Y^a$ are independently selected from O, S, NH and N($C_{1-6}$alkyl); and p is selected from 1, 2, 3, 4, 5 and 6.

In some embodiments, $R^a$ and $R^b$ are independently selected from $C_{1-6}$alkylene, $C_{2-6}$alkenylene and $C_{2-6}$alkynylene. In some embodiments, $R^a$ and $R^b$ are independently selected from $C_{1-6}$-alkylene.

In some embodiments, Q, Y and $Y^a$ are independently selected from O, S, NH and N($CH_3$).

In some embodiments Z and $Z^a$ are independently selected from O, S, S(O), $SO_2$, NH, N($CH_3$), C(O), C(O)NH, NHC(O), NHC(O)O, OC(O)O, NHC(O)NH, OC(O)NH, NHC(NH)NH, ($C_{1-6}$alkyleneO)$_p$ and O—($C_{1-6}$alkyleneO)$_p$.

In some embodiments $L^1$ is selected from OC(O)$C_{1-10}$alkyleneO, NHC(O)$C_{1-10}$alkyleneO, $C_{1-6}$alkyleneO, OC(O)$C_{1-10}$alkyleneNH, NHC(O)$C_{1-10}$alkyleneNH, $C_{1-6}$-alkyleneNH, C(O)$C_{1-10}$alkyleneO and C(O)$C_{1-10}$alkyleneNH.

In some embodiments, $L^2$ is selected from $C_{1-10}$alkyleneS and $C_{1-10}$alkylene.

In some embodiments, the reactive functional groups of $R^1$ and/or $R^5$ are nucleophilic and are reactive to a complementary electrophilic group present on the compound to be attached. Useful electrophilic groups on the compound include, but are not limited to, aldehyde, olefin, acetylene, carboxylic acid, ester and ketone functional groups. In some embodiments, the reactive functional groups of $R^1$ and/or $R^5$ are electrophilic and are reactive to a complementary nucleophilic group present on the compound to be attached. Useful nucleophilic groups on the compound include, but are not limited to, hydrazide, oxime, amino, thiol, hydrazine, thiosemicarbazone, hydrazine carboxylate and aryl hydrazide. In some embodiments, the nucleophilic group is selected from amino and thiol groups provided by reactive lysine and cysteine amino acid groups, respectively.

In some embodiments, the nucleophilic and electrophilic reactive functional groups of $R^1$ and $R^5$ include, but are not limited to, Michael addition acceptors, olefins, acetylenes, alcohols, phenols, ethers, oxides, halides, aldehydes, ketones, carboxylic acids, esters, amines, thiols, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids, isonitriles, amidines, imides, imidates, nitrones, hydroxylamines, oximes, hydroxamic acids, thiohydroxamic acids, allenes, ortho esters, sulfites, enamines, ureas, semicarbazides, carbodiimides, carbamates, N-hydroxysuccinimide esters, imines, azides, azo compounds and nitroso compounds.

In some embodiments, the reactive functional groups of $R^1$ and $R^5$ are independently selected from a nucleophilic group and an electrophilic group. In some embodiments, the reactive functional groups of $R^1$ and $R^5$ are selected from Michael addition acceptors, amines and thiols.

In some embodiments, the reactive functional groups in the compounds of Formula I are an electrophilic reactive functional group such as a N-hydroxysuccinimide ester or other activated ester, or an acid chloride. In some embodiments, the reactive functional groups are a nucleophilic reactive functional group, such as $NH_2$, $NHC_{1-4}alkyl$, OH or SH.

To attach different entities on each side of the linkers of the application it is desirable that each of the reactive functional groups in $R^1$ and $R^5$ have different reactivities so that one of $R^1$ and $R^5$ is functionalized by reaction with a complementary functional group in the presence of the other of $R^1$ and $R^5$, and without the other of $R^1$ and $R^5$ participating in the reaction. In some embodiments, one of $R^1$ and $R^5$ is masked or in protected form (i.e. comprising a protecting group) to prevent it from reacting while the other of $R^1$ and $R^5$ is being functionalized and the masking or protecting group is removed after the first reaction and functionalization is complete.

In some embodiments, $R^2$ is selected from H, Cl, F, $CH_3$, $CF_3$ and $OR^6$. In some embodiments, $R^2$ is $OR^6$.

In some embodiments, $R^3$ and $R^4$ are independently selected from H, CN, $NO_2$, halo, $C_{1-6}$-alkyl, $C_{1-6}$-fluoroalkyl, $OR^8$ and $SR^9$. In some embodiments, $R^3$ and $R^4$ are independently selected from H, CN, F, Cl, $C_{1-6}$-alkyl and $C_{1-6}$fluoroalkyl. In some embodiments, $R^3$ and $R^4$ are independently selected from H, CN, F and $C_{1-6}$alkyl. In some embodiments, $R^3$ and $R^4$ are independently selected from H, F and $C_{1-6}$-alkyl.

In some embodiments, X is O.

In some embodiments, W is selected from O, $NR^{11}$ and S. In some embodiments, W is O.

In some embodiments, $R^6$, $R^7$, $R^8$, $R^9$, $R^{10}$ and $R^{11}$ are independently selected from H, $C_{1-4}$alkyl and $C_{1-4}$fluoroalkyl. In some embodiments, $R^6$, $R^7$, $R^8$, $R^9$, $R^{10}$ and $R^{11}$ are independently selected from H and $C_{1-4}$alkyl. In some embodiments, $R^6$ is H. In some embodiments, $R^6$ is selected from methyl, ethyl, propyl, isopropyl, sec-butyl, n-butyl and t-butyl. In some embodiments, $R^6$ is H or methyl. In some embodiments, $R^7$ is H. In some embodiments, $R^8$, $R^9$, $R^{10}$ and $R^{11}$ are independently selected from H and $CH_3$.

In some embodiments, n is 0, 1 or 2. In some embodiments, n is 1. In some embodiments, n is 2.

In some embodiments, the compound of Formula I has the following structure:

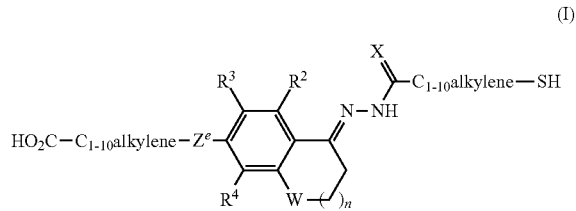

wherein
$R^2$, $R^3$ and $R^4$ are as defined above;
W is as defined above;
$Z^e$ is O or C(O)NH; and
n is 0, 1, 2 or 3.

In some embodiments, the compound of Formula I has the following structure:

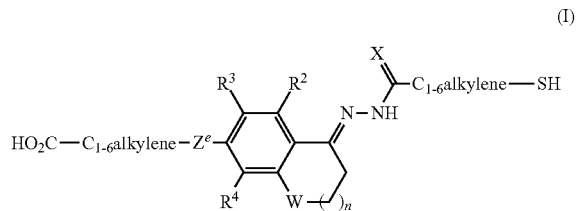

wherein
$R^2$, $R^3$ and $R^4$ are as defined above;
W is as defined above;
$Z^e$ is O or C(O)NH; and
n is 0, 1, 2 or 3.

In some embodiments, the compound of Formula I has the following structure

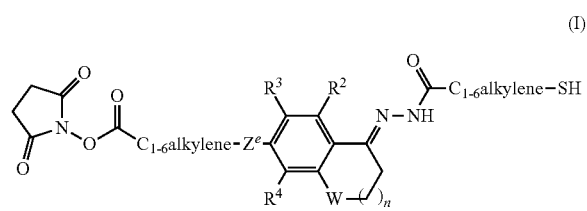

wherein
$R^2$, $R^3$ and $R^4$ are as defined above;
W is as defined above;
$Z^e$ is O or C(O)NH; and
n is 0, 1, 2 or 3.

In some embodiments, $Z^e$ is O.

In some embodiments, the compound of Formula I is selected from

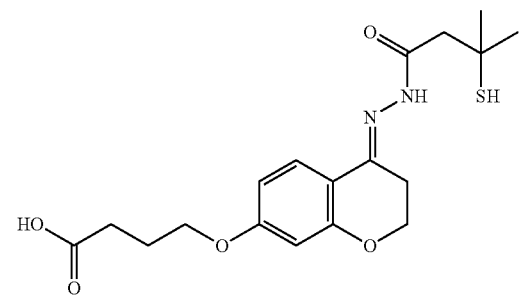
Ia
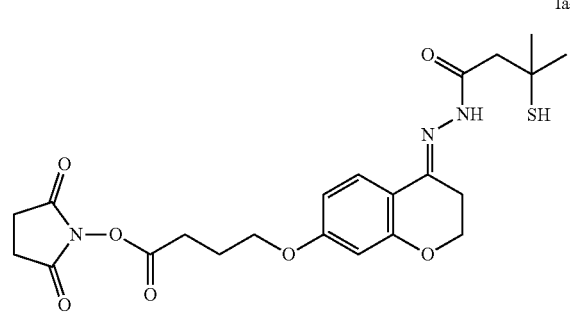
Ia-1
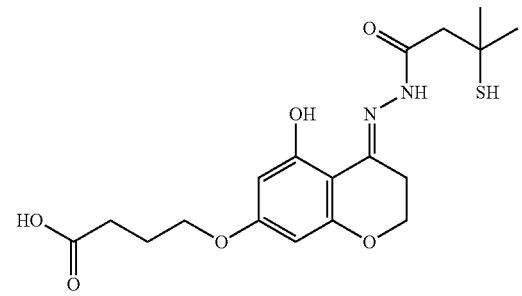
Ib
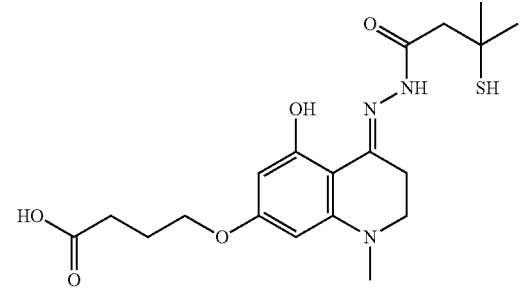
Ic
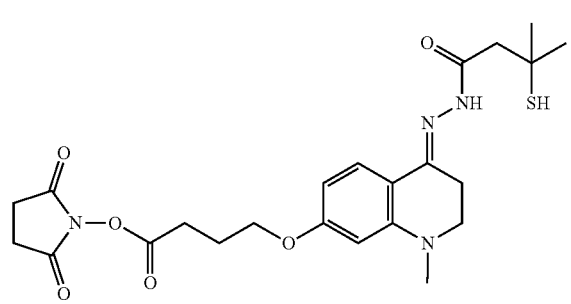
Ic-1
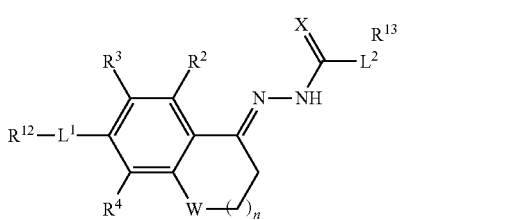
Id
Id-1
If
If-1
or a pharmaceutically acceptable salt and/or solvate thereof.
The present application also includes a compound of Formula (II) or a pharmaceutically acceptable salt and/or solvate thereof:
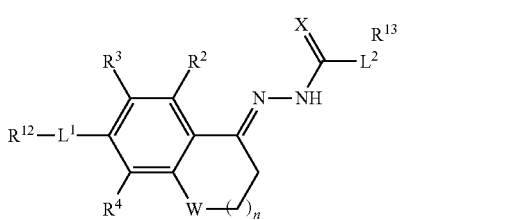
(II)

wherein:
R[12] and R[13] are different and are selected from compounds to be linked together; and
L[1], L[2], R[2], R[3], R[4], X, W and n are as defined above.

In some embodiments, R[12] and R[13] are independently selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex and solid support. In some embodiments, R[12] and R[13] are independently selected from a fluorescent dye, drug, small molecule, antibody, lipid, carbohydrate, nucleic acid, peptide, radiolabel, PET label, nanoparticle, polymer, macrocycle and metal complex.

In some embodiments, R[12] and R[13] are independently selected from an antibody and drug. In some embodiments, one of R[12] and R[13] is an antibody and the other of R[12] and R[13] is a drug. In some embodiments, R[12] is an antibody and R[13] is a drug.

In some embodiments, the compound of Formula (II) is for targeting a binding moiety, a labelling agent and/or a therapeutic agent to a specific site in the body of a subject. Accordingly, in some embodiments, R[12] and R[13] are complementary or dependent on the identity of each other. For example, if R[12] is a payload such as a drug or a label, then R[13] is a complementary group such as a binding moiety targeting a specific site in the body (e.g. a ligand specific for a receptor or an antibody specific for an antigen) which can deliver the payload to that specific site in the body.

In some embodiments, R[12] is an antibody and R[13] is a drug. In some embodiments, the antibody binds to one or more tumor-associated antigens. In some embodiments, the antibody binds to one or more tumor-associated cell-surface receptors and the drug is a drug for treating cancer.

In some embodiments, the antibody is any antibody of therapeutic value. In some embodiments, the antibody is a wild type antibody amenable to cysteine or lysine conjugation. In some embodiments, the antibody is bio-engineered for site specific conjugation to enable a more controlled DAR ratio.

In some embodiments, the antibody is of the immunoglobulin (Ig) type. The immunoglobulin can be of any type (e.g., IgG, IgE, IgM, IgD and IgA), class (e.g., IgG1, IgG2, IgG3, IgG4, IgA1 and IgA2) or subclass of immunoglobulinmolecule.

In some embodiments, the antibody specifically binds to a receptor encoded by an ErbB gene. In some embodiments, the antibody specifically binds to an ErbB receptor selected from EGFR, HER2, HER3 and HER4. In some embodiments, the tumor-associated cell-surface receptor is an ErbB receptor. In some embodiments, the antibody specifically binds to the EGFR receptor.

In some embodiments, the antibody is a monoclonal antibody of the IgG isotype. In some embodiments, the antibody is a chimeric antibody. In some embodiments, the antibody is selected from zalutumumab, nimotuzumab, matuzumab, trastuzumab, and cetuximab. In some embodiments, the antibody is cetuximab. In some embodiments, the antibody is trastuzumab.

In some embodiments, the drug is a drug for treating cancer. In some embodiments, the drug is selected from a protein kinase inhibitor, proteasome inhibitor, topoisomerase inhibitor, aromatase inhibitor, anthracycline, tubulin inhibitor and an alkylating agent. In some embodiments, the drug is a tubulin inhibitor. In some embodiments, the drug is a macrolide. In some embodiments, the drug is a maytansinoid. In some embodiments, the drug is DM1. In some embodiments the drug is a DNA binding agent selected from the pyrrolobenzodiazepine family. In some embodiments, the anticancer drug is a tubulin polymerization inhibitor. In some embodiments, the drug is MMAE.

In some embodiments, the compound of Formula II has the following structure:

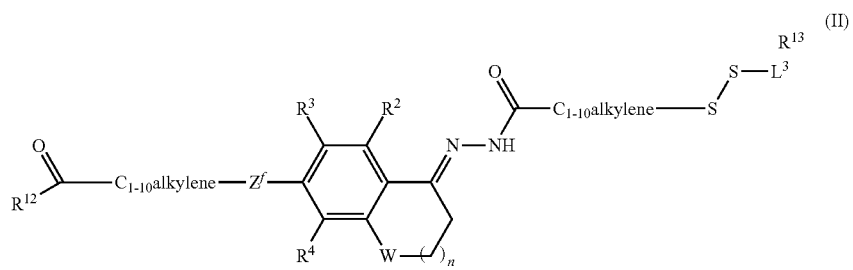

(II)

wherein
R[2], R[3], R[4] and W are as defined above;
R[12] and R[13] are independently selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex and solid support;
L[3] is a linker moiety;
Z[f] is O or C(O)NH; and
n is 0, 1, 2 or 3.

In some embodiments, the compound of Formula II has the following structure:

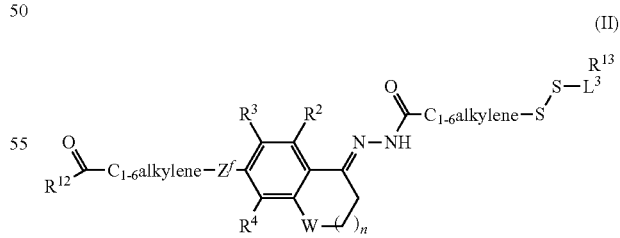

(II)

wherein
R[2], R[3], R[4] and W are as defined above;
R[12] and R[13] are independently selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex and solid support;

L³ is a linker moiety;
Z^f is O or C(O)NH; and
n is 0, 1, 2 or 3.

In some embodiments L³ is selected from a direct bond, Z^bR^c, Z^b—R^c, R^c—Z^b, R^c—Z^b—R^d and Z^b—R^c—Z^c, wherein Z^b and Z^c are independently selected from O, S, S(O), SO₂, NH, N(C$_{1-6}$alkyl), C(Q^a), C(Q^a)Y^b, Y^bC(Q^a) Y^bC(Q^a)Y^c, (Y^bC$_{1-6}$alkylene)$_p$, (C$_{1-6}$alkyleneY^b)$_p$ and Y^b— (C$_{1-6}$alkyleneY^b)$_p$, wherein R^c and R^d are independently selected from C$_{1-10}$alkylene, C$_{2-10}$alkenylene and C$_{2-10}$alkynylene; Q^a, Y^b and Y^c are independently selected from O, S, NH and N(C$_{1-6}$alkyl); and p is selected from 1, 2, 3, 4, 5 and 6.

In some embodiments, R^c and R^d are independently selected from C$_{1-6}$alkylene, C$_{2-6}$alkenylene and C$_{2-6}$alkynylene. In some embodiments, R^c and R^d are independently selected from C$_{1-6}$alkylene.

In some embodiments, Q^a, Y^b and Y^c are independently selected from O, S, NH and N(CH₃).

In some embodiments Z^b and Z^c are independently selected from O, S, S(O), SO₂, NH, N(CH₃), C(O), C(O)NH, NHC(O), NHC(O)O, OC(O)O, NHC(O)NH, OC(O)NH, NHC(NH)NH, (C$_{1-6}$alkyleneO)$_p$ and O—(C$_{1-6}$alkyleneO)$_p$.

In some embodiments L³ is selected from OC(O)C$_{1-10}$alkyleneO, NHC(O)C$_{1-10}$alkyleneO, C$_{1-6}$alkyleneO, OC(O)C$_{1-10}$alkyleneNH, NHC(O)C$_{1-10}$alkyleneNH, C$_{1-6}$alkyleneNH, C(O)C$_{1-10}$alkyleneO and C(O)C$_{1-10}$alkyleneNH. In some embodiments, the acidic half-life of the compounds of Formula II is controlled by the substituent selection for R², R³ and/or R⁴. In some embodiments, to increase the acidic half-life of the compounds of Formula II, R² is OH or R³ is halo, such as F. In some embodiments, to decrease the acidic half-life of the compounds of Formula II, R² is OMe.

In some embodiments, Z^f is O.

In a further aspect, the present application includes a compound of Formula IV or a pharmaceutically acceptable salt and/or solvate thereof

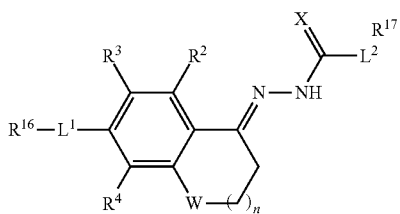

(IV)

wherein
one of R¹⁶ and R¹⁷ is a reactive functional group and the other of R¹⁶ and R¹⁷ is a compound to be linked to another different or same compound; and
L¹, L², R², R³, R⁴, X, W and n are as defined above.

In some embodiments, the reactive functional group in the compounds of Formula IV is an electrophilic reactive functional group such as a N-hydroxysuccinimide ester or other activated ester, or an acid chloride. In some embodiments, the reactive functional group is a nucleophilic reactive functional group, such as NH₂, NHC$_{1-4}$alkyl, OH or SH In some embodiments, R¹⁶ is a reactive functional group and R¹⁷ is a compound to be linked to another different or same compound.

In some embodiments, the compound of Formula IV has the following structure:

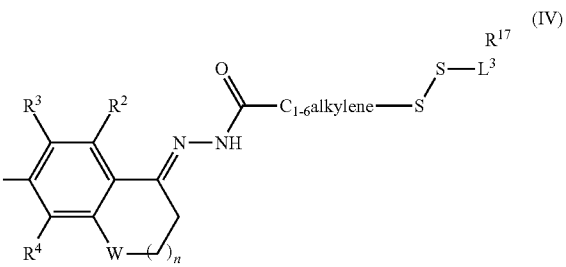

(IV)

wherein
R², R³, R⁴ and W are as defined above;
R¹⁷ is selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex and solid support;
L³ is a linker moiety;
Z^g is O or C(O)NH; and
n is 0, 1, 2 or 3.

In some embodiments L³ is selected from a direct bond, Z^bR^c, Z^b—R^c, R^c—Z^b, R^c—Z^b—R^d and Z^b—R^c—Z^c, wherein Z^b and Z^c are independently selected from O, S, S(O), SO₂, NH, N(C$_{1-6}$alkyl), C(Q^a), C(Q^a)Y^b, Y^bC(Q^a) Y^bC(Q^a)Y^c, (Y^bC$_{1-6}$alkylene)$_p$, (C$_{1-6}$alkyleneY^b)$_p$ and Y^b— (C$_{1-6}$alkyleneY^b)$_p$, wherein R^c and R^d are independently selected from C$_{1-10}$alkylene, C$_{2-10}$alkenylene and C$_{2-10}$alkynylene; Q^a, Y^b and Y^c are independently selected from O, S, NH and N(C$_{1-6}$alkyl); and p is selected from 1, 2, 3, 4, 5 and 6.

In some embodiments, R^c and R^d are independently selected from C$_{1-6}$alkylene, C$_{2-6}$alkenylene and C$_{2-6}$alkynylene. In some embodiments, R^c and R^d are independently selected from C$_{1-6}$alkylene.

In some embodiments, Q^a, Y^b and Y^c are independently selected from O, S, NH and N(CH₃).

In some embodiments Z^b and Z^c are independently selected from O, S, S(O), SO₂, NH, N(CH₃), C(O), C(O)NH, NHC(O), NHC(O)O, OC(O)O, NHC(O)NH, OC(O)NH, NHC(NH)NH, (C$_{1-6}$alkyleneO)$_p$ and O—(C$_{1-6}$alkyleneO)$_p$.

In some embodiments L³ is selected from OC(O)C$_{1-10}$alkyleneO, NHC(O)C$_{1-10}$alkyleneO, C$_{1-6}$alkyleneO, OC(O)C$_{1-10}$alkyleneNH, NHC(O)C$_{1-10}$alkyleneNH, $C_{1-6}$alkyleneNH, $C(O)C_{1-10}$alkyleneO and $C(O)C_{1-10}$alkyleneNH. In some embodiments, the acidic half-life of the compounds of Formula IV is controlled by the substituent selection for $R^2$, $R^3$ and/or $R^4$. In some embodiments, to increase the acidic half-life of the compounds of Formula IV, $R^2$ is OH or $R^3$ is halo, such as F. In some embodiments, to decrease the acidic half-life of the compounds of Formula IV, $R^2$ is OMe.

In some embodiments, $R^{17}$ is selected from selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex and solid support. In some embodiments, $R^{13}$ is selected from an antibody and a drug as defined above.

In some embodiments, $R^{17}$ is an anticancer drug as defined above. In some embodiments, $R^{13}$ is selected from DM1 and MMAE.

In some embodiments, $R^{17}$ is an antibody as defined above. In some embodiments, $R^{17}$ is selected from zalutumumab, nimotuzumab, matuzumab, trastuzumab, and cetuximab. In some embodiments, the antibody is cetuximab. In some embodiments, the antibody is trastuzumab.

In some embodiments, $Z^g$ is O.

In some embodiments, the compound of Formula IV is selected from

IVa

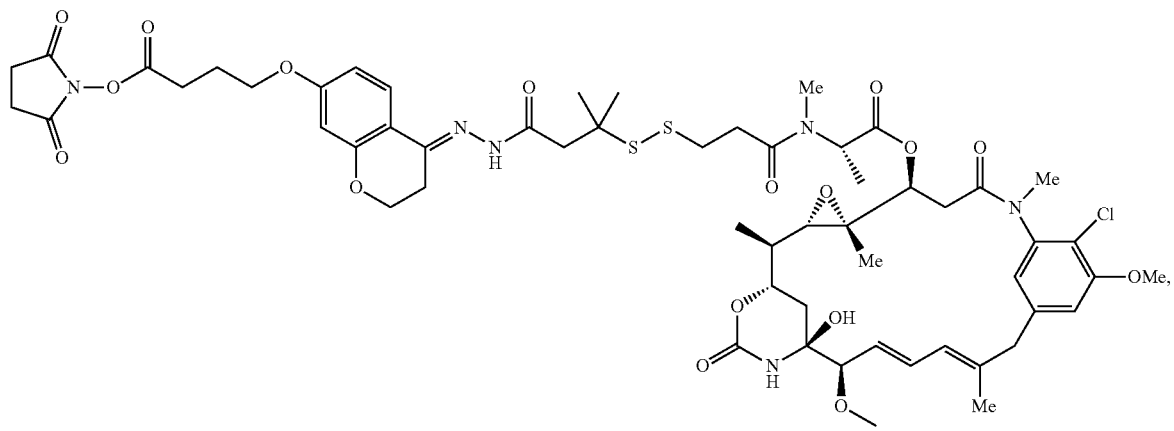

IVb

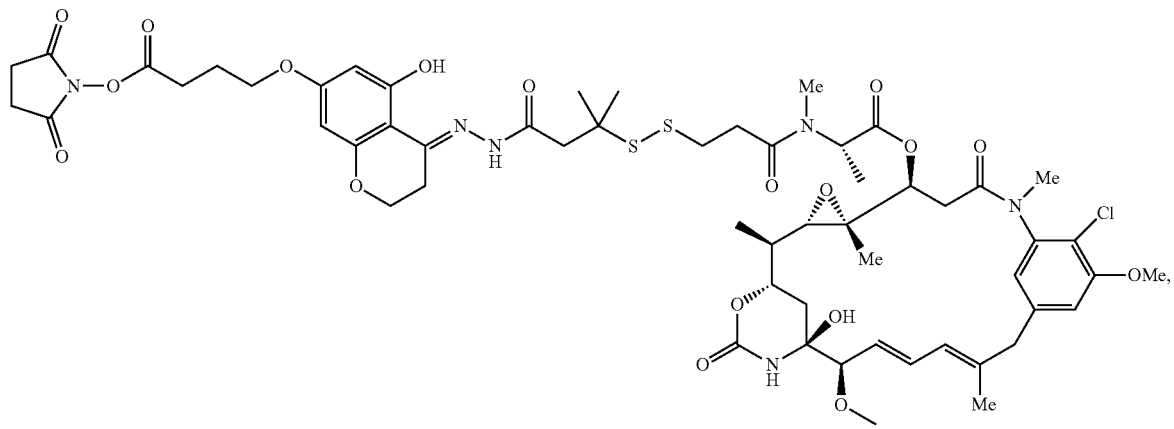

-continued
IVc
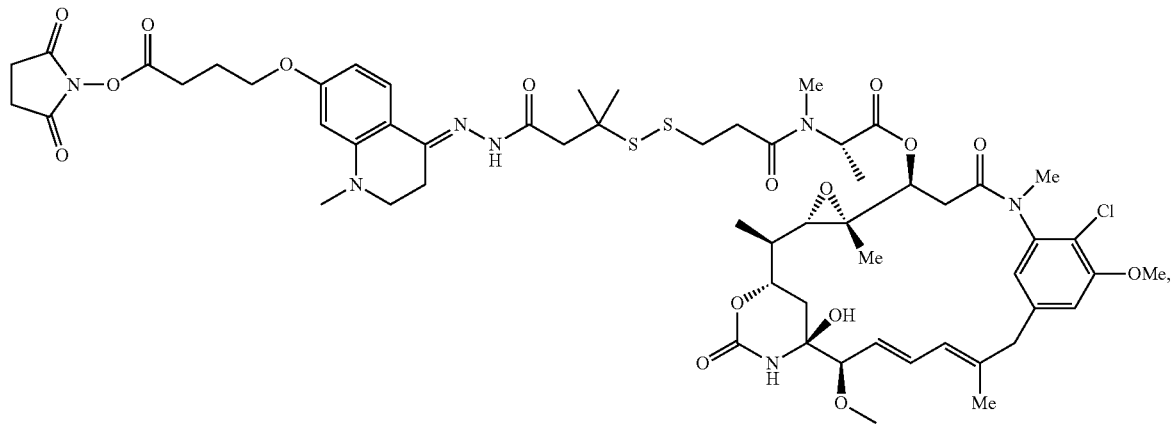
IVd
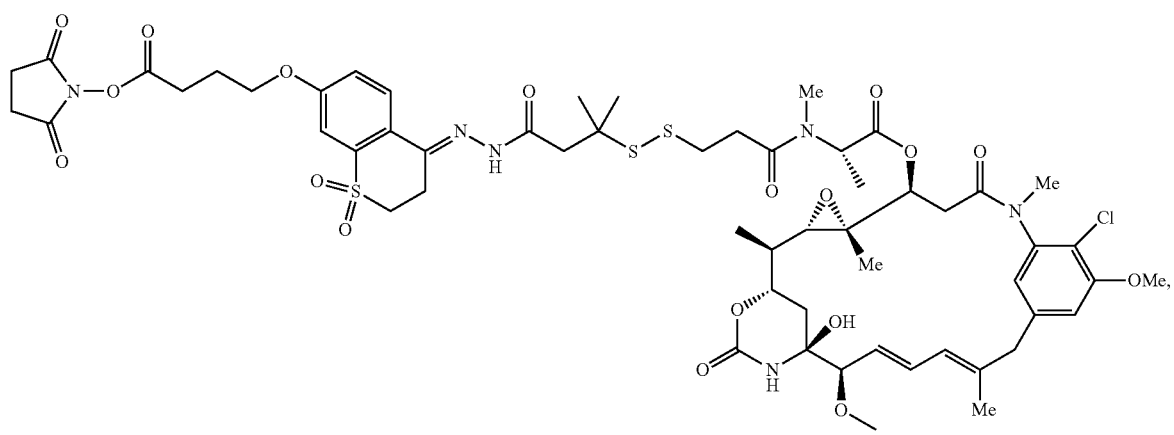
IVf
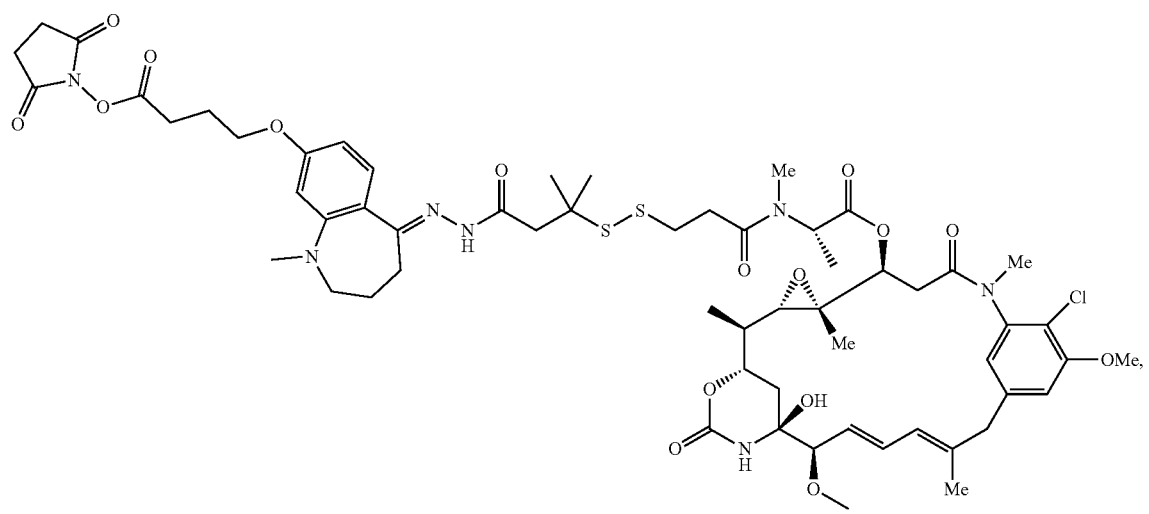
IVg
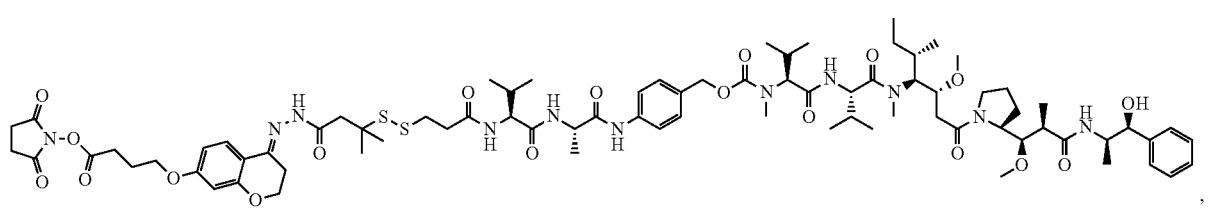

-continued

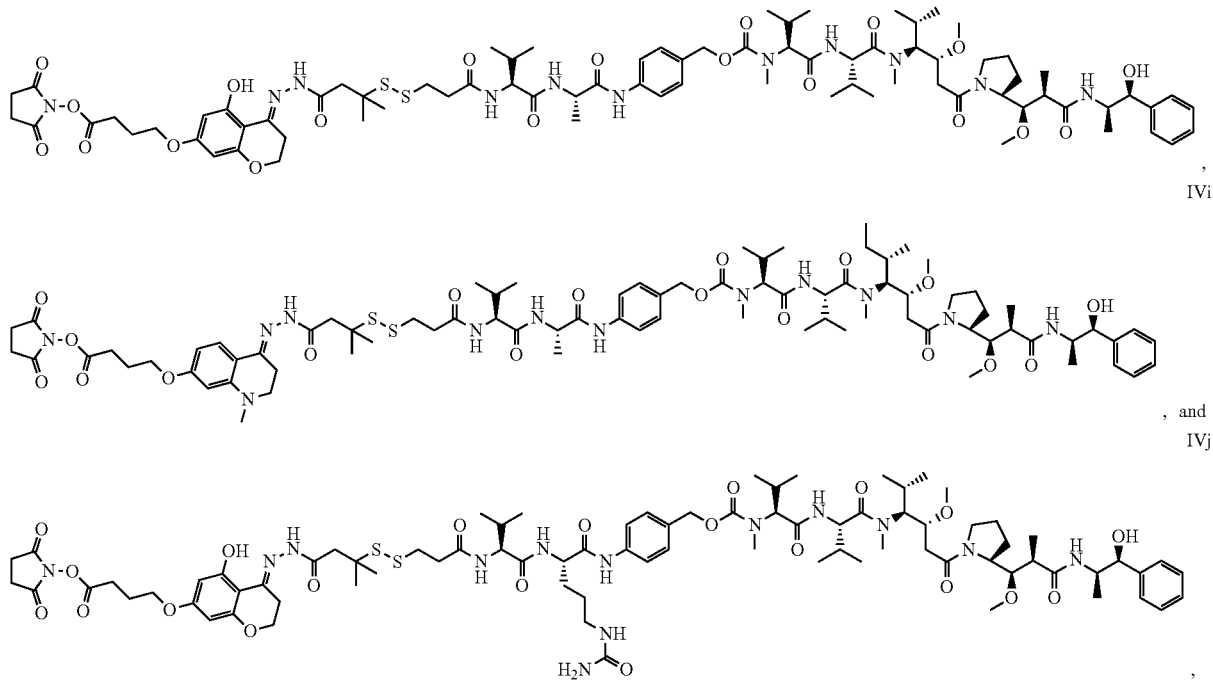

III. Antibody-Drug Conjugates of the Application

The present application includes an antibody-drug conjugate (ADC) comprising an antibody covalently attached by a linker to one or more drugs, the conjugate having a Formula (III):

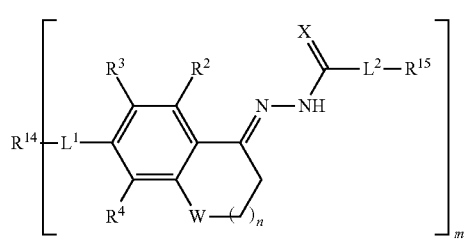

or a pharmaceutically acceptable salt and/or solvate thereof, wherein $R^2$, $R^3$, $R^4$ and W are as defined above;
$R^{14}$ is an antibody;
$R^{15}$ is a drug;
$L^1$, $L^2$, $R^2$, $R^3$, $R^4$, X, W and n are as defined as above; and
m is an integer from 1 to 20.

In some embodiments, the compound of Formula III has the following structure:

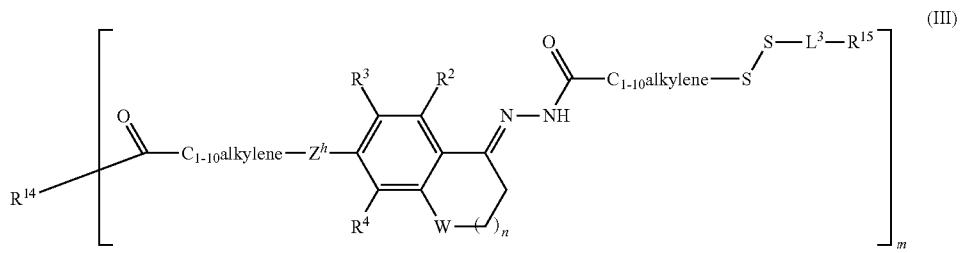

or a pharmaceutically acceptable salt and/or solvate thereof, wherein $R^2$, $R^3$, $R^4$ and W are as defined above;
$R^{14}$ is an antibody;
$R^{15}$ is a drug;
$L^1$, $L^2$, $R^2$, $R^3$, $R^4$, W and n are as defined as above;
$L^3$ is a linker moiety;
$Z^h$ is O or C(O)NH; and
m is an integer from 1 to 20.

In some embodiments, the compound of Formula III has the following structure:

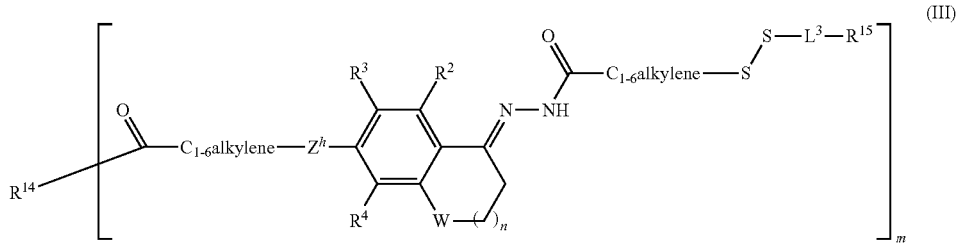

or a pharmaceutically acceptable salt and/or solvate thereof, wherein $R^2$, $R^3$, $R^4$ and W are as defined above;
$R^{14}$ is an antibody;
$R^{15}$ is a drug;
$L^1$, $L^2$, $R^2$, $R^3$, $R^4$, W and n are as defined as above;
$L^3$ is a linker moiety;
$Z^h$ is O or C(O)NH; and
m is an integer from 1 to 20.

In some embodiments in the compounds of Formula III $L^3$ is selected from a direct bond, $Z^b R^c$, $Z^b$—$R^c$, $R^c$—$Z^b$, $R^c$—$Z^b$—$R^d$ and $Z^b$—$R^c$—$Z^c$, wherein $Z^b$ and $Z^c$ are independently selected from O, S, S(O), $SO_2$, NH, N($C_{1-6}$alkyl), C($Q^a$), C($Q^a$)$Y^b$ $Y^b$C($Q^a$), $Y^b$C($Q^a$)$Y^c$, ($Y^b C_{1-6}$alkylene)$_p$, ($C_{1-6}$alkylene$Y^b$)$_p$ and $Y^b$—($C_{1-6}$alkylene$Y^b$)$_p$, wherein $R^c$ and $R^d$ are independently selected from $C_{1-10}$alkylene, $C_{2-10}$alkenylene and $C_{2-10}$alkynylene; $Q^a$, $Y^b$ and $Y^c$ are independently selected from O, S, NH and N($C_{1-6}$alkyl); and p is selected from 1, 2, 3, 4, 5 and 6.

In some embodiments in the compounds of Formula III $R^c$ and $R^d$ are independently selected from $C_{1-6}$alkylene, $C_{2-6}$alkenylene and $C_{2-6}$alkynylene. In some embodiments, $R^c$ and $R^d$ are independently selected from $C_{1-6}$alkylene.

In some embodiment in the compounds of Formula III $Q^a$, $Y^b$ and $Y^c$ are independently selected from O, S, NH and N($CH_3$).

In some embodiments in the compounds of Formula III $Z^b$ and $Z^c$ are independently selected from O, S, S(O), $SO_2$, NH, N($CH_3$), C(O), C(O)NH, NHC(O), NHC(O)O, OC(O)O, NHC(O)NH, OC(O)NH, NHC(NH)NH, ($C_{1-6}$alkyleneO)$_p$ and O—($C_{1-6}$alkyleneO)$_p$.

In some embodiments, the antibody binds to one or more tumor-associated antigens. In some embodiments, the antibody binds to one or more tumor-associated cell-surface receptors. In some embodiments, the antibody specifically binds to a receptor encoded by an ErbB gene. In some embodiments, the tumor-associated cell-surface receptor is an ErbB receptor.

In some embodiments, the antibody specifically binds to an ErbB receptor selected from EGFR, HER2, HER3 and HER4. In some embodiments, the antibody specifically binds to the EGFR receptor. In some embodiments, the antibody is a monoclonal antibody. In some embodiments, the antibody is a chimeric antibody. In some embodiments, the antibody is selected from zalutumumab, nimotuzumab, matuzumab, trastuzumab and cetuximab. In some embodiments, the antibody is cetuximab. In some embodiments, the antibody is trastuzumab.

In some embodiments, the drug is a drug for targeting cancer. In some embodiments, the drug is selected from a protein kinase inhibitor, proteasome inhibitor, topoisomerase inhibitor, aromatase inhibitor, anthracycline, tubulin inhibitor and an alkylating agent. In some embodiments, the drug is tubulin inhibitor. In some embodiments, the drug is a macrolide. In some embodiments, the drug is a maytansinoid. In some embodiments, the one or more drug moieties is DM1. In some embodiments the drug is a DNA binding agent selected from the pyrrolobenzodiazepine family.

In some embodiments, the drug is an anticancer drug. In some embodiments, the anticancer drug is a thiol-containing anticancer drug or a calicheamicin derivative. In some embodiments, the thiol containing anticancer drug is a maytansinoid, such as DM1. In some embodiments the drug is a DNA binding agent selected from the pyrrolobenzodiazepine family. In some embodiments, the anticancer drug is a tubulin polymerization inhibitor. In some embodiments, the drug is MMAE.

The drug loading of ADCs is represented by the integer m, which indicates the average number of drugs conjugated per antibody in the conjugate of Formula (III). The drug to antibody (DAR) ratio is relevant for the preparation of ADC's, as higher drug loading, e.g. m>5, may cause aggregation, insolubility, toxicity or loss of cellular permeability. Further, the DAR ratio is dependent upon the number of reactive sites present on the antibody. For example, where the attachment point is a cysteine thiol or lysine amine, as in the exemplary embodiments of the present application, an antibody may have only one or few number of these reactive groups through which a linker maybe attached. Additionally, the antibody may be subjected to denaturing conditions to reveal reactive nucleophilic groups such as lysine and cysteine. In some embodiments, the DAR ratio of the compounds of Formula (III) ranges from 1 to 20 drugs per antibody.

In some embodiments, $Z^h$ is O.

In some embodiments, m is an integer from 1 to 10. In some embodiments, m is an integer from 1 to 5.

Known antibodies for the treatment and prevention of cancer can be conjugated as ADCs. Antibodies immunospecific for a cancer cell antigen are obtained commercially or produced by any method known to a person skilled in the art, including, e.g., chemical syntheses or by recombinant expression techniques. In some embodiments, the nucleotide sequence encoding antibodies immunospecific for a cancer cell antigens is obtained, for example, from the GenBank database or a similar nucleotide sequence database, literature publications, or through routine cloning and sequencing.

In some embodiments, the ADCs of the present application selectively deliver an effective dose of a cytotoxic agent, such as a drug, to tumor tissue with greater selectivity, i.e., a lower effective dose is achieved, than upon delivery of the same dose of drug not conjugated to an antibody.

In some embodiments, the drug of the compound of Formula III is not cleaved from the antibody until the compound enters a cell with a cell-surface receptor specific for the antibody of the compound, at which time the drug is cleaved from the antibody. In some embodiments, the drug is intracellularly cleaved from the antibody of the compound of Formula III through enzymatic action, hydrolysis, oxidation or pH conditions. In some embodiments, the acidic half-life of the compounds of Formula III is controlled by the substituent selection for $R^2$, $R^3$ and/or $R^4$. In some embodiments, to increase the acidic half-life of the compounds of Formula III, $R^2$ is H or $R^3$ is halo, such as F.

In some embodiments, the compound of Formula III is selected from

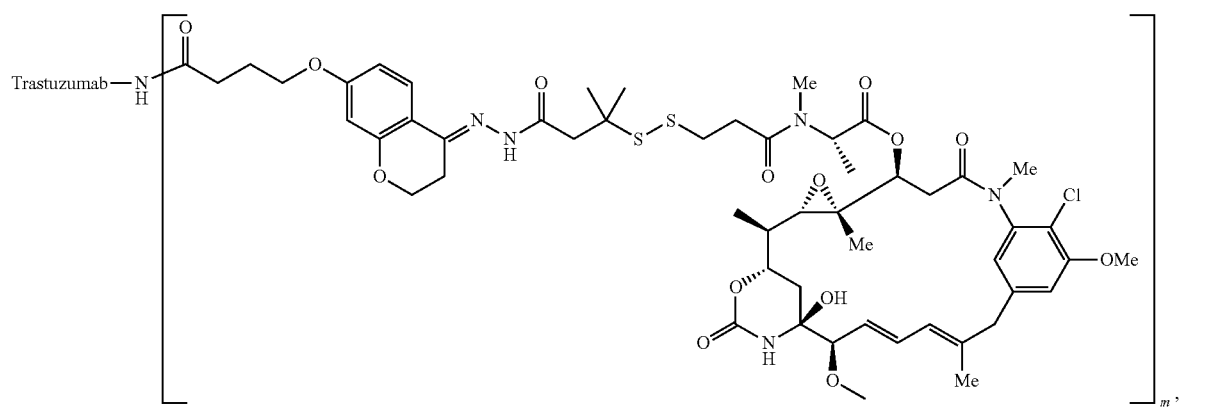

IIIa

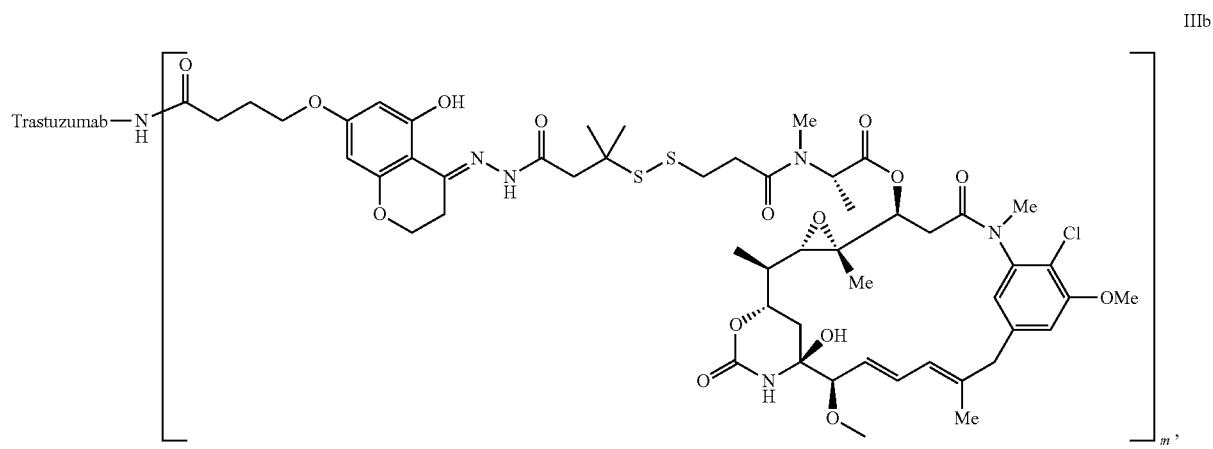

IIIb

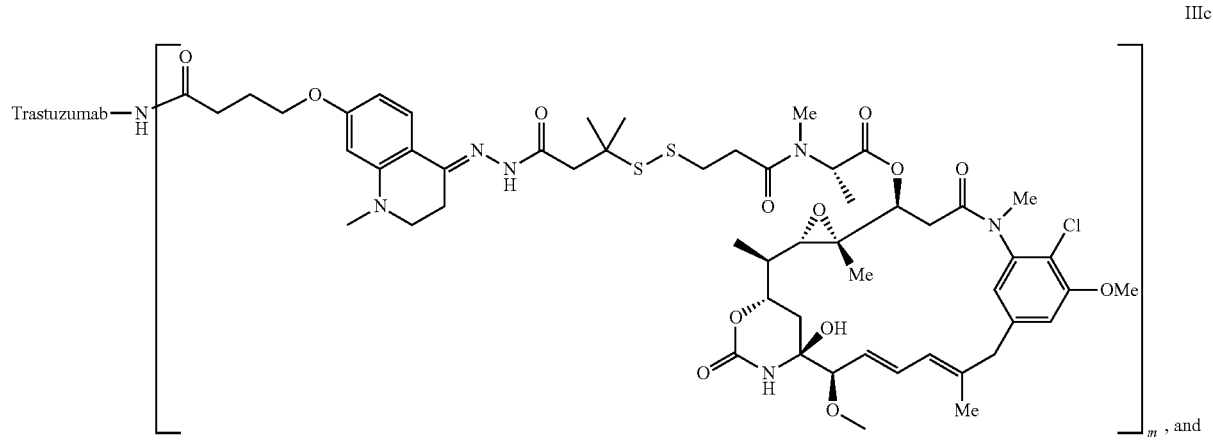

IIIc, and

-continued
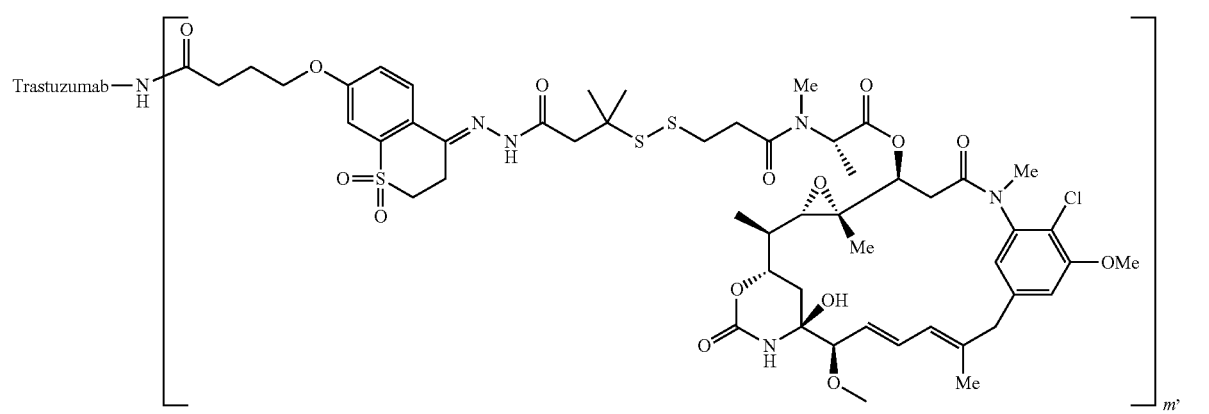
IIId
or pharmaceutically acceptable salt and/or solvate thereof.
In some embodiments, the compound of Formula III is selected from:
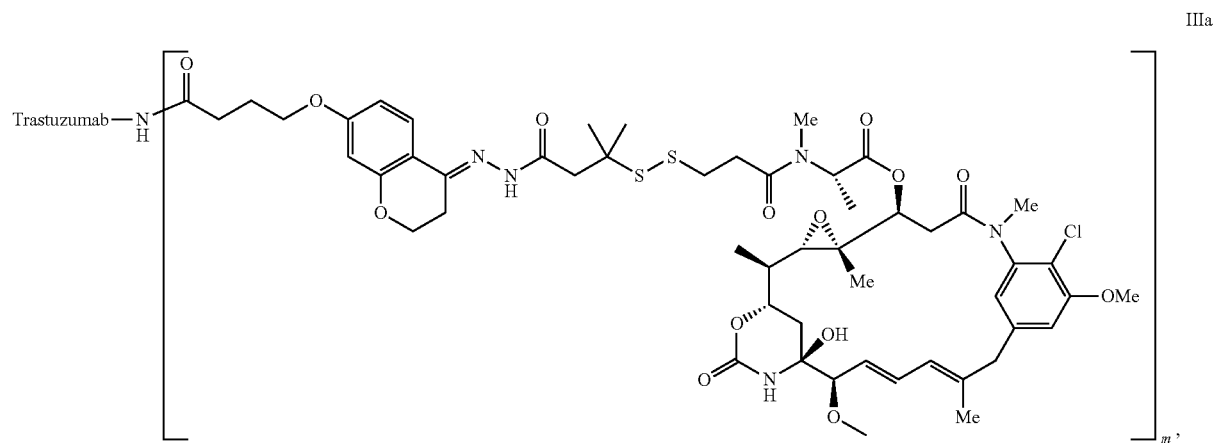
IIIa
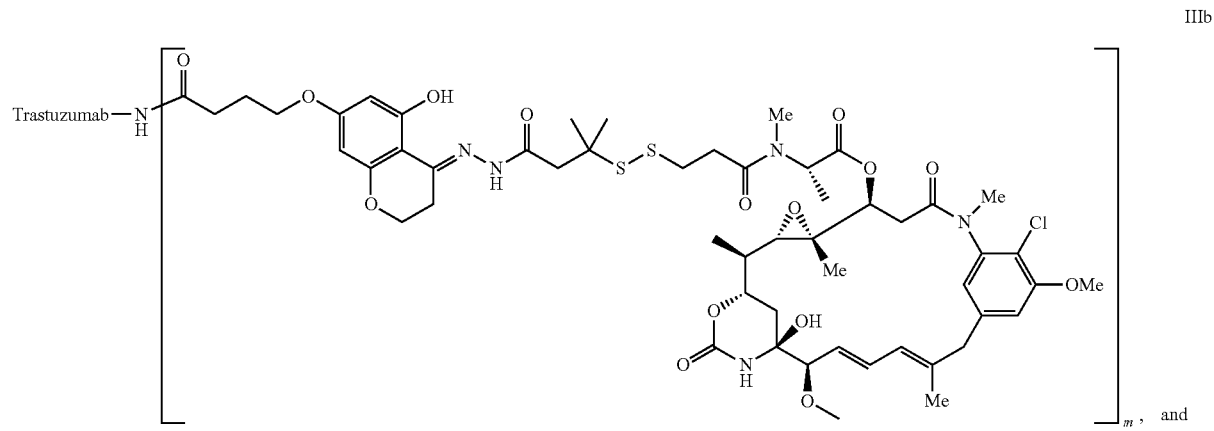
IIIb
and -continued

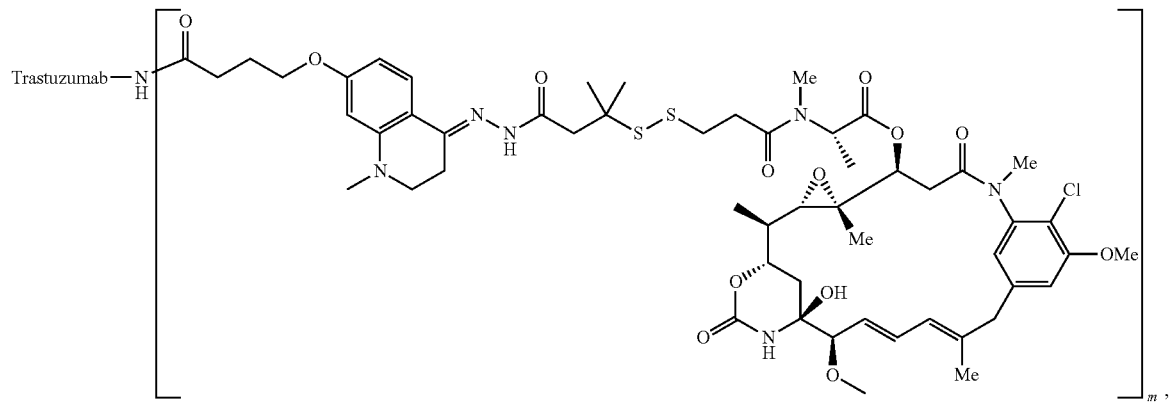

or pharmaceutically acceptable salt and/or solvate thereof.

IV. Methods of Preparing Compounds of the Application

Scheme (1) illustrates one embodiment of a route to compounds of the application in which a functionalized hydrazide is formed from commercially available compounds A', wherein $R^5$ is a reactive functional group or a protected form thereof and X and $L^2$ are as defined in Formula I to afford intermediates B'. The subsequent coupling of B' with aromatic compounds C', wherein $R^1$-$R^4$, $L^1$ and n are as defined in Formula I and in which $R^1$ may be in protected form, provides compounds of the application.

Scheme (1)

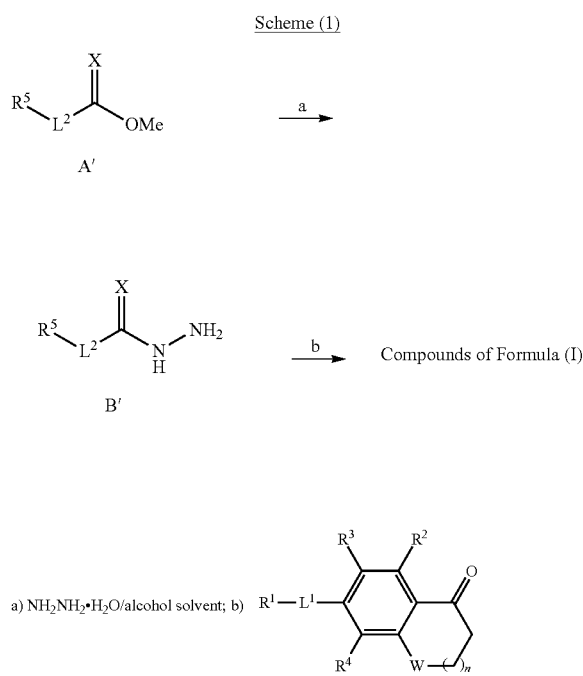

Compounds of Formula C'

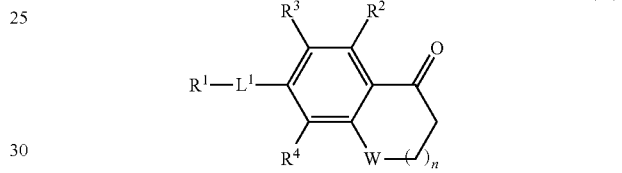

are either commercially available or are synthesized from commercially available compounds using methods known in the art, for example starting from compounds of Formula D':

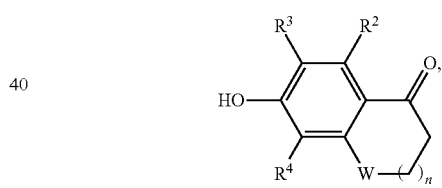

wherein $R^2$-$R^4$ are as defined in Formula (I).

In some embodiments, the reactive functional groups $R^1$ and $R^5$ of the compounds of Formula (I) are subsequently conjugated to a complementary reactive functional group of compounds to be linked, for example, a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex or solid support, to produce the compounds of Formula (II) or (III) of the present application.

Accordingly, in another aspect, the present application includes a method of synthesizing one or more compounds of Formula (II) or (III) as defined above, or a pharmaceutically acceptable salt and/or solvate thereof, wherein the method comprises reacting one or more compounds of Formula (I) as defined above with a first compound to be linked, for example, selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex or solid support, and then a second, different compound to be linked, for example, selected from a fluorescent dye, ligand, drug, small molecule, antibody, lipid, carbohydrate, nucleic acid, peptide, radiolabel, spin label, redox molecule, isotope label, PET label, nanoparticle, polymer, macrocycle, metal complex and solid support.

To attach different entities on each side of the hydrazine linkers of the application it is desirable that each of the reactive functional groups in $R^1$ and $R^5$ have different reactivities so that one of $R^1$ and $R^5$ can be functionalized by reaction with a complementary functional group in the presence of the other of $R^1$ and $R^5$, and without the other of $R^1$ and $R^5$ participating in the reaction. In some embodiments, one of $R^1$ and $R^5$ is masked or in protected form (i.e. comprises a protecting group) to prevent it from reacting while the other of $R^1$ and $R^5$ is being functionalized and the masking or protecting group is removed after the first reaction and functionalization is complete.

For preparing ADC compounds of Formula (III) of the application, in some embodiments, a compound of Formula (I)-drug conjugate or a compound of Formula (IV) is first prepared. Methods for conjugating a Formula (I)-drug conjugate or a compound of Formula (IV) to an antibody and purifying the ADCs are known to those skilled in the art.

Accordingly, in another aspect the present application includes a method of preparing an ADC of Formula (III) comprising:
(a) reacting a compound of Formula (I) with a drug to provide a Formula (I)-drug conjugate;
(b) reacting the Formula (I)-drug conjugate with an antibody to provide the ADC of Formula (III); and optionally
(c) purifying the ADC of Formula (III).

Accordingly, in another aspect, the present application includes a method of preparing an ADC of Formula (III) comprising:
(a) reacting a compound of Formula (IV) with an antibody to provide the ADC of Formula (III); and optionally
(b) purifying the ADC of Formula (III).

The present application also includes a use of a compound of Formula (I) or (IV) to prepare an ADC of Formula (III).

In some embodiments, the resulting ADC of Formula (III) products are isolated or purified using known methods, such as for example, lyophilization, chromatography, precipitation, filtration, microfluidic and/or liquid chromatography separation methods.

In some embodiments, the drug is a drug for targeting cancer. In some embodiments, the drug is selected from a protein kinase inhibitor, proteasome inhibitor, topoisomerase inhibitor, aromatase inhibitor, anthracycline, tubulin inhibitor and an alkylating agent. In some embodiments, the drug is tubulin inhibitor. In some embodiments, the drug is a macrolide. In some embodiments, the drug is a maytansinoid. In some embodiments, the one or more drug moieties is DM1. In some embodiments the drug is a DNA binding agent selected from the pyrrolobenzodiazepine family.

In some embodiments, the drug is an anticancer drug. In some embodiments, the anticancer drug is a thiol-containing anticancer drug or a calicheamicin derivative. In some embodiments, the thiol containing anticancer drug is a maytansinoid, such as DM1. In some embodiments the drug is a DNA binding agent is selected from the pyrrolobenzodiazepine family. In some embodiments, the anticancer drug is a tubulin polymerization inhibitor. In some embodiments, the drug is MMAE.

V. Compositions of the Application

The compounds of the application are suitably formulated in a conventional manner into compositions using one or more carriers. Accordingly, the present application also includes a composition comprising one or more compounds of the application and a carrier. The compounds of Formula (II) and/or (III), or pharmaceutically acceptable salts and/or solvates thereof, are suitably formulated into pharmaceutical compositions for administration to subjects in a biologically compatible form suitable for administration in vivo. Accordingly, the present application further includes a pharmaceutical composition comprising one or more compounds of Formula (II) and/or (III), or pharmaceutically acceptable salts and/or solvates thereof, and a pharmaceutically acceptable carrier. In embodiments of the application the pharmaceutical compositions are used in the treatment and/or diagnosis of any of the diseases, disorders or conditions described herein.

The compounds of Formula (II) and/or (III), or pharmaceutically acceptable salts and/or solvates thereof, are administered to a subject in a variety of forms depending on the selected route of administration, as will be understood by those skilled in the art. For example, compounds Formula (II) and/or (III), or pharmaceutically acceptable salts and/or solvates thereof, are administered by oral, inhalation, parenteral, buccal, sublingual, nasal, rectal, vaginal, patch, pump, topical or transdermal administration and the pharmaceutical compositions formulated accordingly. In some embodiments, administration is by means of a pump for periodic or continuous delivery. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

Parenteral administration includes systemic delivery routes other than the gastrointestinal (GI) tract, and includes, for example intravenous, intra-arterial, intraperitoneal, subcutaneous, intramuscular, transepithelial, nasal, intrapulmonary (for example, by use of an aerosol), intrathecal, rectal and topical (including the use of a patch or other transdermal delivery device) modes of administration. Parenteral administration may be by continuous infusion over a selected period of time.

In some embodiments, compounds of Formula (II) and/or (III), or pharmaceutically acceptable salts and/or solvates thereof, are orally administered, for example, with an inert diluent or with an assimilable edible carrier, or are enclosed in hard or soft shell gelatin capsules, or are compressed into tablets, or are incorporated directly with the food of the diet. In some embodiments, the compounds are incorporated with excipient and used in the form of ingestible tablets, buccal tablets, troches, capsules, caplets, pellets, granules, lozenges, chewing gum, powders, syrups, elixirs, wafers, aqueous solutions and suspensions, and the like. In the case of tablets, carriers that are used include lactose, corn starch, sodium citrate and salts of phosphoric acid. Pharmaceutically acceptable excipients include binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). In embodiments, the tablets are coated by methods well known in the art. In the case of tablets, capsules, caplets, pellets or granules for oral administration, pH sensitive enteric coatings, such as Eudragits™ designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions are formulated, for example as liposomes or those wherein the active compounds are protected with differentially degradable coatings, such as by microencapsulation, multiple coatings, etc. Liposome delivery systems include, for example, small unilamellar vesicles, large unilamellar vesicles and multilamellar vesicles. In some embodiments, liposomes are formed from a variety of phospholipids, such as cholesterol, stearylamine or phosphatidylcholines. For oral administration in a capsule form, useful carriers or diluents include lactose and dried corn starch.

In some embodiments, liquid preparations for oral administration take the form of, for example, solutions, syrups or suspensions, or they are suitably presented as a dry product for constitution with water or other suitable vehicle before use. When aqueous suspensions and/or emulsions are administered orally, the compounds of Formula (II) and/or (III), or pharmaceutically acceptable salts and/or solvates thereof, are suitably suspended or dissolved in an oily phase that is combined with emulsifying and/or suspending agents. If desired, certain sweetening and/or flavoring and/or coloring agents are added. Such liquid preparations for oral administration are prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid). Useful diluents include lactose and high molecular weight polyethylene glycols.

It is also possible to freeze-dry the compounds of Formula (II) and/or (III), or pharmaceutically acceptable salts and/or solvates thereof, and use the lyophilizates obtained, for example, for the preparation of products for injection.

In some embodiments, the compounds of Formula (II) and/or (III), or pharmaceutically acceptable salts and/or solvates thereof, are administered parenterally. For example, solutions of compounds of Formula (II) and/or (III), or pharmaceutically acceptable salts and/or solvates thereof, are prepared in water suitably mixed with a surfactant such as hydroxypropylcellulose. In some embodiments, dispersions are prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. For parenteral administration, sterile solutions of the compounds of Formula (II) and/or (III), or pharmaceutically acceptable salts and/or solvates thereof, are usually prepared, and the pHs of the solutions are suitably adjusted and buffered. For intravenous use, the total concentration of solutes should be controlled to render the preparation isotonic. For ocular administration, ointments or droppable liquids are delivered, for example, by ocular delivery systems known to the art such as applicators or eye droppers. In some embodiment, such compositions include mucomimetics such as hyaluronic acid, chondroitin sulfate, hydroxypropyl methylcellulose or polyvinyl alcohol, preservatives such as sorbic acid, EDTA or benzyl chromium chloride, and the usual quantities of diluents or carriers. For pulmonary administration, diluents or carriers will be selected to be appropriate to allow the formation of an aerosol.

In some embodiments, compounds of Formula (II) and/or (III), or pharmaceutically acceptable salts and/or solvates thereof, are formulated for parenteral administration by injection, including using conventional catheterization techniques or infusion. Formulations for injection are, for example, presented in unit dosage form, e.g., in ampoules or in multi-dose containers, with an added preservative. In some embodiments, the compositions take such forms as sterile suspensions, solutions or emulsions in oily or aqueous vehicles, and contain formulating agents such as suspending, stabilizing and/or dispersing agents. In all cases, the form must be sterile and must be fluid to the extent that easy syringability exists. Alternatively, the compounds of the application are suitably in a sterile powder form for reconstitution with a suitable vehicle, e.g., sterile pyrogen-free water, before use.

In some embodiments, compositions for nasal administration are conveniently formulated as aerosols, drops, gels and powders. For intranasal administration or administration by inhalation, the compounds of Formula (II) and/or (III), or pharmaceutically acceptable salts and/or solvates thereof, are conveniently delivered in the form of a solution, dry powder formulation or suspension from a pump spray container that is squeezed or pumped by the patient or as an aerosol spray presentation from a pressurized container or a nebulizer. Aerosol formulations typically comprise a solution or fine suspension of the active substance in a physiologically acceptable aqueous or non-aqueous solvent and are usually presented in single or multidose quantities in sterile form in a sealed container, which, for example, take the form of a cartridge or refill for use with an atomising device. Alternatively, the sealed container is a unitary dispensing device such as a single dose nasal inhaler or an aerosol dispenser fitted with a metering valve, which is intended for disposal after use. Where the dosage form comprises an aerosol dispenser, it will contain a propellant, which is, for example, a compressed gas such as compressed air or an organic propellant such as fluorochlorohydrocarbon. Suitable propellants include but are not limited to dichlorodifluoromethane, trichlorofluoromethane, dichlorotetrafluoroethane, heptafluoroalkanes, carbon dioxide or another suitable gas. In the case of a pressurized aerosol, the dosage unit is suitably determined by providing a valve to deliver a metered amount. In some embodiments, the pressurized container or nebulizer contains a solution or suspension of the active compound. Capsules and cartridges (made, for example, from gelatin) for use in an inhaler or insufflator are, for example, formulated containing a powder mix of compounds of Formula (II) and/or (III), or pharmaceutically acceptable salts and/or solvates thereof, and a suitable powder base such as lactose or starch. The aerosol dosage forms can also take the form of a pump-atomizer.

Compositions suitable for buccal or sublingual administration include tablets, lozenges, and pastilles, wherein compounds of Formula (II) and/or (III), or pharmaceutically acceptable salts and/or solvates thereof, are formulated with a carrier such as sugar, acacia, tragacanth, or gelatin and glycerine. Compositions for rectal administration are conveniently in the form of suppositories containing a conventional suppository base such as cocoa butter.

Suppository forms of the compounds of Formula (II) and/or (III), or pharmaceutically acceptable salts and/or solvates thereof, are useful for vaginal, urethral and rectal administrations. Such suppositories will generally be constructed of a mixture of substances that is solid at room temperature but melts at body temperature. The substances commonly used to create such vehicles include but are not limited to theobroma oil (also known as cocoa butter), glycerinated gelatin, other glycerides, hydrogenated vegetable oils, mixtures of polyethylene glycols of various molecular weights and fatty acid esters of polyethylene glycol. See, for example: *Remington's Pharmaceutical Sciences,* 16th Ed., Mack Publishing, Easton, PA, 1980, pp. 1530-1533 for further discussion of suppository dosage forms.

In some embodiments compounds of Formula (II) and/or (III), or pharmaceutically acceptable salts and/or solvates thereof, are coupled with soluble polymers as targetable drug carriers. Such polymers include, for example, polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, in some embodiments, compounds of Formula (II) and/or (III), or pharmaceutically acceptable salts and/or solvates thereof, are coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The compounds of Formula (II) and/or (III), or pharmaceutically acceptable salts and/or solvates thereof, are suitably used on their own but will generally be administered in the form of a pharmaceutical composition in which the one or more compounds of Formula (II) and/or (III), or pharmaceutically acceptable salts and/or solvates thereof, (the active ingredient) are in association with a pharmaceutically acceptable carrier. Depending on the mode of administration, the pharmaceutical composition will comprise from about 0.05 wt % to about 99 wt % or about 0.10 wt % to about 70 wt %, of the active ingredient, and from about 1 wt % to about 99.95 wt % or about 30 wt % to about 99.90 wt % of a pharmaceutically acceptable carrier, all percentages by weight being based on the total composition.

The compounds of Formula (II) and/or (III), or pharmaceutically acceptable salts and/or solvates thereof, are either used alone or in combination with other known agents useful for treatment and/or imaging. When used in combination with other agents useful in treatment and/or imaging, it is an embodiment that compounds of Formula (II) and/or (III), or pharmaceutically acceptable salts and/or solvates thereof, are administered contemporaneously with those agents. As used herein, "contemporaneous administration" of two substances to a subject means providing each of the two substances so that they are both active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion. In an embodiment, compounds of Formula (II) and/or (III), or pharmaceutically acceptable salts and/or solvates thereof, are administered with another therapeutic agent simultaneously or sequentially in separate unit dosage forms or together in a single unit dosage form. Accordingly, the present application provides a single unit dosage form comprising one or more compounds of Formula (II) and/or (III), or pharmaceutically acceptable salts and/or solvates thereof, an additional therapeutic agent, and a pharmaceutically acceptable carrier.

In some embodiments, the additional therapeutic agent is a chemotherapeutic agent. In some embodiments, the chemotherapeutic agent is selected from the classes of alkylating agents, anthracyclines, cytoskeletal disruptors, epothilones, histone deacetylase inhibitors, topoisomerase inhibitors, kinase inhibitors, nucleotide analogs, peptide antibiotics, platinum-based agents, retinoids, Vinca alkaloids, epigenetic modifiers and immuno-modulators.

VI. Methods and Uses of the Application

Compounds of Formula (II) and/or (III), or pharmaceutically acceptable salts and/or solvates thereof, comprise a wide variety of active compounds which have possibilities of treating and/or diagnosing a variety of diseases, disorders or conditions.

Accordingly, the present application includes a method of treating and/or diagnosing one or more diseases, disorders or conditions by administering an effective amount of one or more compounds of Formula (II) and/or (III), or pharmaceutically acceptable salts and/or solvates thereof, to a subject in need thereof. In some embodiments, the disease, disorder or condition depends on the identity of the compounds being conjugated as would be understood by a person skilled in the art.

In some embodiments, the disease, disorder or condition is a neoplastic disorder. Accordingly, the present application also includes a method of treating and/or diagnosing a neoplastic disorder comprising administering a therapeutically effective amount of one or more compounds of Formula (II) and/or (III), or pharmaceutically acceptable salts and/or solvates thereof, to a subject in need thereof. The present application also includes a use of one or more compounds of Formula (II) and/or (III), or pharmaceutically acceptable salts and/or solvates thereof, for treatment of and/or diagnosing a neoplastic disorder as well as a use of one or more compounds of Formula (II) and/or (III), or pharmaceutically acceptable salts and/or solvates thereof, for the preparation of a medicament for treatment of and/or diagnosing a neoplastic disorder. The application further includes one or more compounds of Formula (II) and/or (III), or pharmaceutically acceptable salts and/or solvates thereof, for use in treating and/or diagnosing a neoplastic disorder. In an embodiment, the treatment is in an amount effective to ameliorate at least one symptom of the neoplastic disorder, for example, reduced cell proliferation or reduced tumor mass, among others, in a subject in need of such treatment.

In some embodiments, the present application includes a method of treating and/or diagnosing one or more diseases, disorders or conditions mediated by ErbB comprising administering a therapeutically effective amount of one or more compounds of Formula (II) and/or (III), or pharmaceutically acceptable salts and/or solvates thereof, to a subject in need thereof. The present application also includes a use of one or more compounds of Formula (II) and/or (III), or pharmaceutically acceptable salts and/or solvates thereof, for treatment of and/or diagnosing one or more diseases, disorders or conditions mediated by ErbB as well as a use of one or more compounds of Formula (II) and/or (III), or pharmaceutically acceptable salts and/or solvates thereof, for the preparation of a medicament for treatment of and/or diagnosing one or more diseases, disorders or conditions mediated by ErbB.

In some embodiments, the disease, disorder or condition is cancer. Accordingly, the present application also includes a method of treating and/or diagnosing cancer comprising administering a therapeutically effective amount of one or more compounds of Formula (II) and/or (III), or pharmaceutically acceptable salts and/or solvates thereof, to a subject in need thereof. The present application also includes a use of one or more compounds of Formula (II) and/or (III), or pharmaceutically acceptable salts and/or solvates thereof, for treatment of and/or diagnosing cancer as well as a use of one or more compounds of Formula (II) and/or (III), or pharmaceutically acceptable salts and/or solvates thereof, for the preparation of a medicament for treatment of and/or diagnosing cancer. The application further includes one or more compounds of Formula (II) and/or (III), or pharmaceutically acceptable salts and/or solvates thereof, for use in treating cancer. In an embodiment, the compound is administered for the prevention of cancer in a subject such as a mammal having a predisposition for cancer. In some embodiments, the cancer is an ErbB-expressing cancer. In some embodiments, the subject is human.

In some embodiments, the cancer is selected from, but not limited to: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood;

Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated in accordance with the methods described herein.

In some embodiments, the cancer is selected from ErbB-expressing cancer. In some embodiments, the cancer is selected from breast cancer, skin cancer, prostate cancer, head and neck cancer, colorectal cancer, pancreatic cancer, kidney cancer, lung cancer and brain cancer. In some embodiments of the present application, the cancer is selected from breast cancer, prostate cancer, head and neck cancer, colorectal cancer, pancreatic cancer, kidney cancer, lung cancer and brain cancer.

In a further embodiment, the one or more compounds of the application are administered in combination with one or more additional cancer treatments. In another embodiment, the additional cancer treatment is selected from radiotherapy, chemotherapy, targeted therapies such as antibody therapies and small molecule therapies such as tyrosine-kinase inhibitors, immunotherapy, hormonal therapy and anti-angiogenic therapies.

In some embodiments, when the methods and uses are related to diagnostics, one compound to be linked comprises a binding moiety and the other compound to be linked comprises a labelling agent.

EXAMPLES

The following non-limiting examples are illustrative of the present application:

A. General Methods

Exemplary compounds of the application were synthesized using the methods described herein, or other methods, which are known in the art. Unless otherwise noted, reagents and solvents were obtained from commercial suppliers (e.g. Aldrich, Alfa Aesar, Enamine, Combi-Blocks, Bepharm, J&W PharmLab).

The compounds and/or intermediates were characterized by high performance liquid chromatography (HPLC) using a Waters ACQUITY UPLC system with a SQ (single quadrupole) MS and a photodiode array (PDA) detector (Milford, MA). The analytical columns were reversed phase Acquity UPLC BEH C18 (2.1×50 mm, 1.7 μm). A gradient elution was used (flow 0.4 mL/min), typically starting with mobile phase 0.1% formic acid in water (solvent A) and 0.1% formic acid in acetonitrile (solvent B). A gradient starting at 95% solvent A going to 5% in 1.8 min., holding for 0.5 min., going back to 95% in 0.5 min. and equilibrating the column for 0.5 min. Compounds were detected by ultraviolet light (UV) absorption at either 220 or 254 nm. HPLC solvents were from Fisher Scientific (Pittsburgh, PA) or other common vendors.

In some instances, purity was assessed by thin layer chromatography (TLC) using glass or plastic backed silica gel plates, such as, for example, Baker-Flex Silica Gel IB2-F flexible sheets. TLC results were readily detected visually under ultraviolet light, or by employing well-known iodine vapor and other various staining techniques The compounds and/or intermediates were characterized by LCMS. General conditions are as follows. Low and High resolution Mass spectra were acquired on LC/MS systems using electrospray ionization methods from a range of instruments of the following configurations: Low resolution—Waters ACQUITY UPLC system with a SQ (single quadrupole) MS; Waters ACQUITY UPLC H-Class system with a 3100 (single quadrupole) MS. High resolution—Waters ACQUITY UPLC II system equipped with a Synapt Xevo QTof and Waters ACQUITY UPLC II system equipped with a Synapt G2S QTof mass spectrometer with an atmospheric pressure ionization source. [M+H] refers to the protonated molecular ion of the chemical species.

Nuclear magnetic resonance (NMR) analysis was performed on a Bruker 500 MHz NMR spectrometer using ICON-NMR, under TopSpin program control. Spectra were measured at 298K, unless indicated otherwise and were referenced relative to the solvent chemical shift.

B. Model Experiments

Towards the goal developing enhanced control of ADC linker stability, several model cyclic acyl hydrazones whose lability is modulated by different substitutions have been prepared. Exemplary acyl hydrazones containing a substituted phenyl group adjacent to the imine carbon have been synthesized. Starting with the acyl hydrazone structure (A) present in Mylotarg the adjacent steric and electronic environments were varied and their half-life tested in a simulated lysosomal environment (pH 4.5), as shown in Table 1. When the imine carbon is part of heterocyclic structure (as in B), about a 7-fold increase in half-life was observed compared to the corresponding acyclic structure A. The heterocyclic linkers also showed a half life on the order of twice that of the corresponding carbocyclic linkers (compare B with C and E with F). Incorporation of a fluoro group ortho to the acyl hydrazone (as in D) restored the half-life to a similar range of A half-life. On the other hand, incorporation of a fluoro group in the meta position (as in E) rendered the heterocyclic hydrazone more stable with a half-life of 139 min. These results suggest that the adjacent steric and electronic environment can affect the stability of acyl hydrazones. Analogues of the heterocyclic linker compounds in Table 1 have been incorporated into linkers, using a similar strategy as employed in the linker synthesis in Mylotarg, as described in greater detail herein below

TABLE 1

Effects of substituents on stability of acyl hydrazones

| Compound | Structure | Acidic (pH 4.5) Half life (min) |
|---|---|---|
| A | MeO-phenyl-C(CH₃)=N-NH-C(O)-CH₃ | 15 |

TABLE 1-continued

Effects of substituents on stability of acyl hydrazones

| Compound | Structure | Acidic (pH 4.5) Half life (min) |
|---|---|---|
| B | MeO-chromanone acyl hydrazone (7-MeO) | 102 |
| C | MeO-tetrahydronaphthalenone acyl hydrazone (6-MeO) | 41 |
| D | 5-F chromanone acyl hydrazone | 24 |
| E | 6-F chromanone hydrazide | 139 |
| F | 7-F tetrahydronaphthalenone hydrazide | 88 |

In addition, for an ADO to have a better therapeutic window, ideally it should be stable in plasma and having the payload released only upon entry to the target cells. This targeted cytotoxicity would be, mostly, confined to the diseased cells of interest. Starting with the acyl hydrazone structure (A) present in Mylotarg, the adjacent steric and electronic environments were varied and their stability was tested in plasma. Upon a 6 day incubation in human plasma, the amount of remaining parent acyl hydrazone was measured as shown in Table 2. Reference compound (A) showed a moderate stability with 37% remaining. When a fluoro group is introduced in the ortho position and a tetrahydro dihydropyran ring is bearing the imine carbon (as in D), there was only a marginal improvement in stability with 42% remaining. Removing the fluoro group and incorporating a methoxy group in the para position of this ring system (as in B) gave a compound with a very good plasma stability with 77% remaining after 6 days.

TABLE 2

Effects of sterics and electronics on stability of acyl hydrazones after 6 days incubation in human plasma

| Compound | Structure | % remaining after 6 days |
|---|---|---|
| A | MeO-phenyl methyl ketone acyl hydrazone | 37 |
| B | MeO-chromanone acyl hydrazone (7-MeO) | 77 |
| D | 5-F chromanone acyl hydrazone | 42 |

These results suggest that the adjacent steric and electronic environments can affect the stability of acyl hydrazones. Analogues of the compounds in Tables 1 & 2 have been incorporated into linkers, using a similar strategy as employed in the linker synthesis in Mylotarg, as described in greater detail herein below.

C. Synthesis of Compounds of the Application

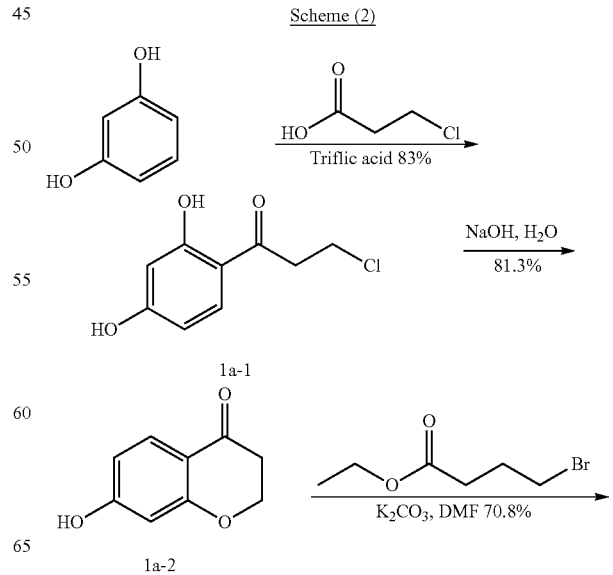

Scheme (2)

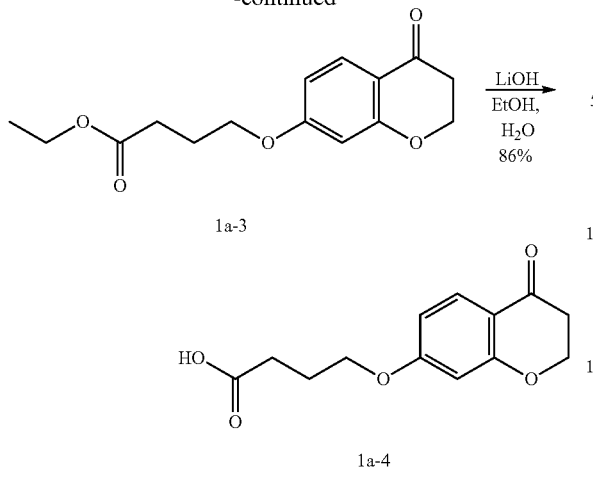

1a-3

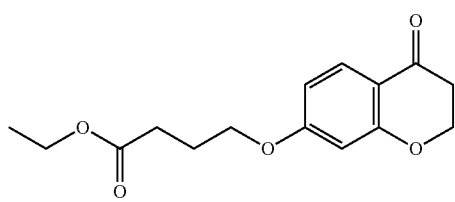

1a-4

Compounds 1a-1 and 1a-2 were prepared according the procedures described in reference 50.

Ethyl 4-((4-oxochroman-7-yl)oxy)butanoate (1a-3)

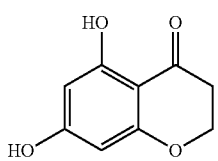

1a-3

To a solution of compound 1a-2 (5 g, 30.47 mmol) in DMF (50 ml) was added K$_2$CO$_3$ (6.31 g, 45.71 mmol) and ethyl 4-bromobutanoate (8.86 g, 45.71 mmol). The resulting reaction mixture was heated at 80° C. for 3 h. The reaction mixture was poured into ice/water upon which a solid precipitated out. It was filtered and dried under vacuum to give the title compound 1a-3 as an off-white solid (6 g, 70.8% yield). LCMS [M+H]$^+$ 279.

4-((4-Oxochroman-7-yl)oxy)butanoic acid (1a-4)

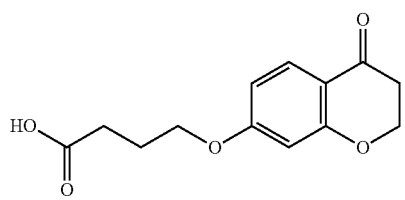

1a-4

To a solution of compound 1a-3 (4 g, 14.38 mmol) in EtOH/H$_2$O (40/20 ml) was added LiOH (0.68 g, 28.77 mmol) then the mixture was stirred at room temperature for 4 h. The reaction mixture was cooled to 0° C., acidified with AcOH then extracted with EtOAc. The combined organic layers were dried over Na$_2$SO$_4$ and concentrated under reduced pressure to give the crude product. This material was washed with diethyl ether to give the title compound 1a-4 as an off-white solid (3.1 g, 86% yield). LCMS [M+H]$^+$ 251.

Scheme (3)

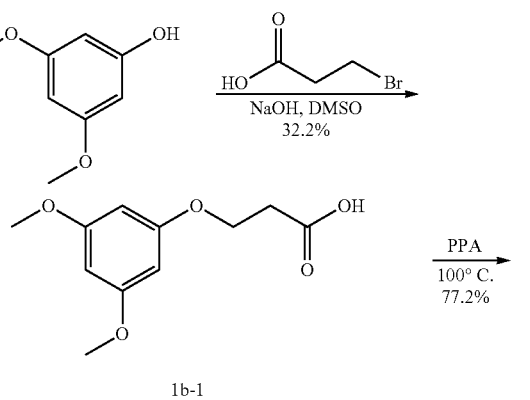

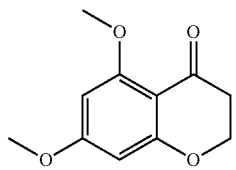

1b-1

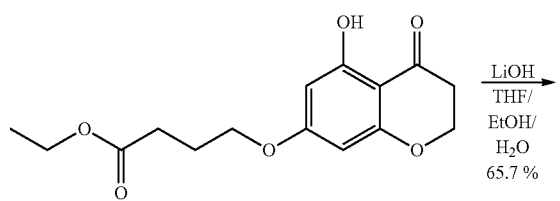

1b-2

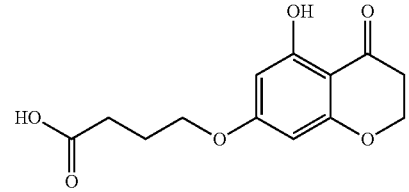

1b-3

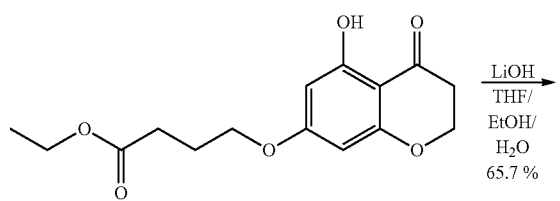

1b-4

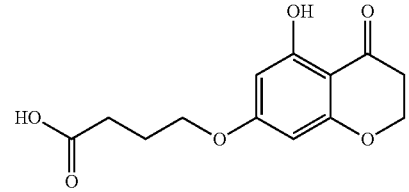

1b-5

3-(3,5-Dimethoxyphenoxy)propanoic acid (1b-1)

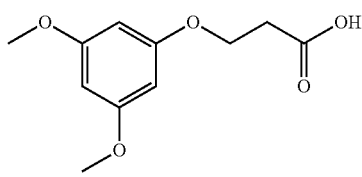

To a stirred solution of 3,5-dimethoxyphenol (11.4 g, 77.02 mmol) in DMSO (60 ml) was added NaOH powder (13.5 g, 88.82 mmol) followed by a solution of 3-bromopropanoic acid (11.84 g, 296 mmol) in DMSO (40 ml). The mixture was stirred at rt for 48 h under argon atmosphere. The reaction mixture was diluted with water (50 ml), cooled to 0° C. then acidified to pH=1 by 2N HCl. The precipitate that has formed was collected and dried to give the title compound 1b-1 as an off-white solid (5.6 g, 32.2% yield). LCMS [M+H]$^+$ 227.

5,7-Dimethoxychroman-4-one (1b-2)

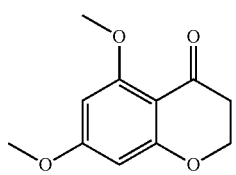

A stirred solution of 3-(3,5-dimethoxyphenoxy)propanoic acid 1b-1 (2.8 g, 12.44) in PPA (30 g) was heated at 100° C. for 2 h. The reaction mixture was cooled to rt, poured into ice-cold water then extracted with EtOAc (2×500 ml). The combined organic layers were washed with a saturated Na$_2$CO$_3$ solution (500 ml), brine (200 ml) then dried over sodium sulfate. It was concentrated down to give the title compound 1b-2 as an off-white solid (2.0 g, 77.2% yield). LCMS [M+H]$^+$ 209.

5,7-Dihydroxychroman-4-one (1b-3)

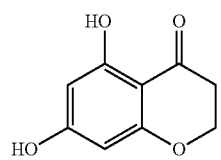

A stirred solution of 5,7-dimethoxychroman-4-one 1b-2 (1.9 g, 9.13 mmol) in 48% aq. HBr (65 ml) was heated at 100° C. for 16 h. The reaction mixture was poured into water (100 ml) and extracted with EtOAc (2×200 ml). The combined organic layers were concentrated down to give the title compound 1b-3 as a brown solid (0.75 g, 45.6% yield). LCMS [M+H]$^+$ 181.

Ethyl 4-((5-hydroxy-4-oxochroman-7-yl)oxy)butanoate (1b-4)

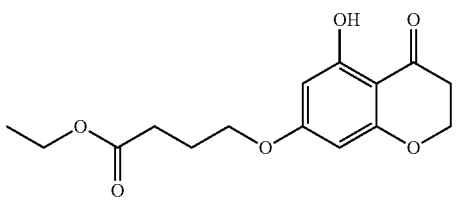

A stirred solution of 5,7-dihydroxychroman-4-one 1b-3 (1.3 g, 7.22 mmol) in DMF (20 ml) was cooled to 0° C. then potassium carbonate (2.0 g, 14.44 mmol) was added. Ethyl 4-bromobutanoate (1.2 ml, 8.66 mmol) was added to the reaction mixture which was stirred at rt for 16 h. It was diluted with water (200 ml), acidified with 2N HCl then extracted with EtOAc (2×500 ml). The combined organic layers were dried over Na$_2$SO$_4$ and concentrated under reduced pressure. The crude product was purified by column chromatography (silica gel 100-200 mesh) using 0-40% EtOAc in petroleum ether to give the title compound 1b-4 as an off-white solid (1.4 g, 66% yield). LCMS [M+H]$^+$ 295.

4-((5-Hydroxy-4-oxochroman-7-yl)oxy)butanoic acid (1b-5)

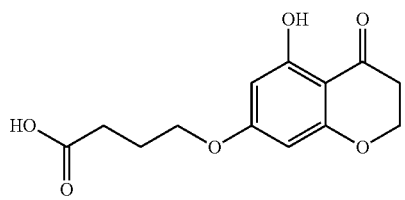

To a stirred solution of ethyl 4-((5-hydroxy-4-oxochroman-7-yl)oxy)butanoate 1b-4 (2.35 g, 7.98 mmol) in THF/EtOH/H$_2$O (20/10/20 ml) was added lithium hydroxide monohydrate (475 mg, 8.27 mmol) then the resulting mixture was stirred at rt for 16 h. The volatiles were evaporated under reduced pressure. The residue was acidified with 2N HCl (10 ml). The solid that has precipitated was filtered and washed with n-pentane (10 ml) to give the title compound 1b-5 as an off-white solid (1.4 g, 65.7% yield). $^1$H NMR (400 MHz, DMSO-d6) β=12.18 (br s, 1H), 12.18 (s, 1H), 6.04 (s, 2H), 4.46 (t, J=6.4 Hz, 2H), 4.03 (t, J=6.4 Hz, 2H), 2.79 (t, J=6.4 Hz 2H), 2.34 (t, J=7.0 Hz, 2H), 1.95-1.85 (m, 2H); LCMS [M+H]$^+$ 267.

Scheme (4)

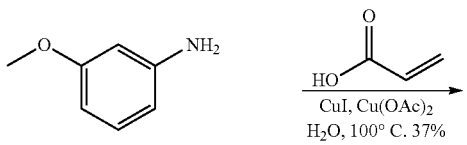

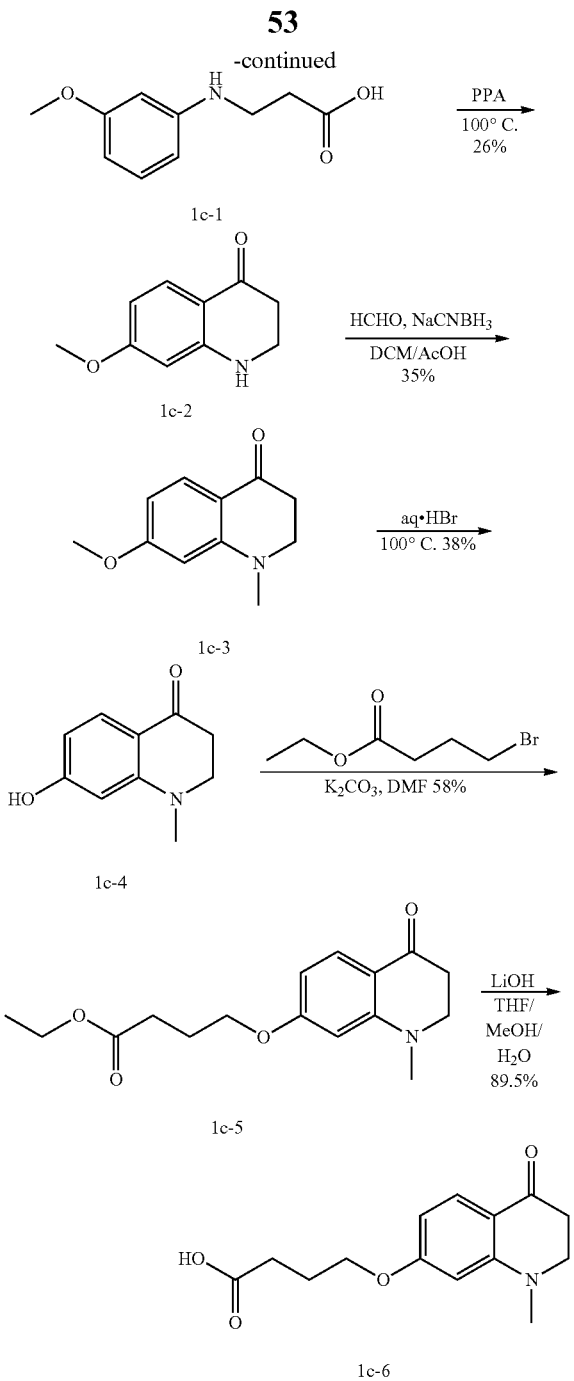

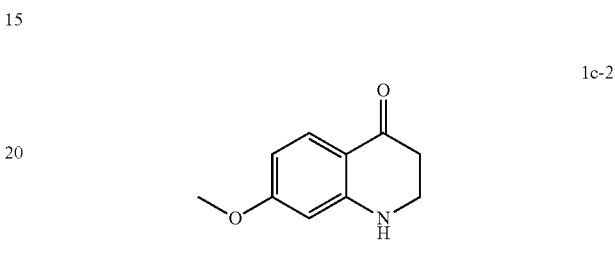

3-((3-Methoxyphenyl)amino)propanoic acid (1c-1)

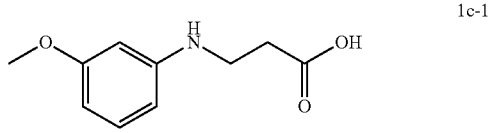

To a stirred solution of acrylic acid (5 g, 69.4 mmol) in water (10 ml) was added copper (I) iodide (0.025 g, 0.13 mmol), copper (II) acetate (0.025 g, 0.14 mmol) followed by 3-methoxyaniline (15.5 ml, 138.4 mmol). The resulting mixture was heated at 120° C. for 16 h. It was basified with a 2N NaOH solution and extracted with EtOAc. The aqueous layer was acidified with 2N HCl and extracted with ethyl acetate (2×100 ml). The combined organics layers were dried over Na$_2$SO$_4$ and concentrated under reduced pressure. The crude product was purified by column chromatography (silica 100-200 mesh) using 0-50% EtOAc in petroleum ether to give the title compound 1c-1 as a brown liquid (10 g, 37% yield). LCMS [M+H]$^+$ 196.

7-Methoxy-2,3-dihydroquinolin-4(1H)-one (1c-2)

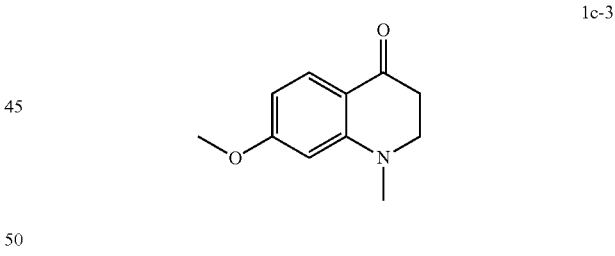

A stirred solution of 3-((3-methoxyphenyl)amino)propanoic acid 1c-1 (2.3 g, 12.99 mmol) in PPA (7 g) was heated at 100° C. for 1 h. The reaction mixture was cooled to rt, poured into ice cold water then extracted with EtOAc (2×50 ml). The combined organic layers were washed with a saturated sodium carbonate solution (50 ml), brine (20 ml) then dried over sodium sulfate. It was concentrated under reduced pressure to give the title compound 1c-2 as a pale yellow solid (0.6 g, 26% yield). LCMS [M+H]$^+$ 178.

7-Methoxy-1-methyl-2,3-dihydroquinolin-4(1H)-one (1c-3)

To a stirred solution of 7-methoxy-2,3-dihydroquinolin-4(1H)-one 1c-2 (6 g, 33.8 mmol) in DCM/AcOH (2/1, 20 ml) was added 37% HCHO (5.1 ml, 50.7 mmol). It was stirred at rt for 2 h and cooled to 0° C. NaCNBH$_3$ (4.247 g, 67.6 mmol) was added then the mixture was stirred at rt for 16 h. The reaction mixture was concentrated under reduced pressure, basified with a 2N NaHCO$_3$ solution and extracted with DCM (2×100 ml). The combined organic layers were dried over Na$_2$SO$_4$ and concentrated under reduced pressure. The crude product was purified by column chromatography (silica 100-200 mesh) using 0-50% EtOAc in petroleum ether to give the title compound 1c-3 as a brown solid (2.3 g, 35% yield). LCMS [M+H]$^+$ 192.

7-Hydroxy-1-methyl-2,3-dihydroquinolin-4(1H)-one (1c-4)

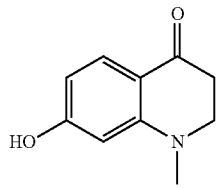

A stirred solution of 7-methoxy-1-methyl-2,3-dihydroquinolin-4(1H)-one 1c-3 (2 g, 10.4 mmol) in 48% Aq HBr (30V) was heated at 100° C. for 6 h. The reaction mixture was cooled to rt, poured into ice cold water then extracted with EtOAc (2×50 ml). The combined organic layers were dried over sodium sulfate and concentrated down to give the title compound 1c-4 as a pale yellow solid (0.7 g, 38.8% yield). LCMS [M+H]$^+$ 178.

Ethyl 4-((1-methyl-4-oxo-1,2,3,4-tetrahydroquinolin-7-yl)oxy)butanoate (1c-5)

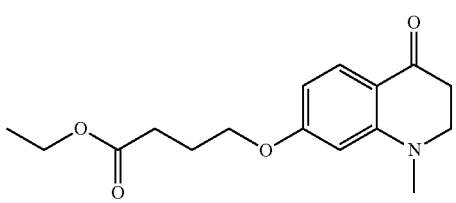

A stirred solution of 7-hydroxy-1-methyl-2,3-dihydroquinolin-4(1H)-one 1c-4 (2.3 g, 12.42 mmol) in DMF (17.6 ml) was cooled to 0° C. then potassium carbonate (2.57 g, 18.63 mmol) was added followed by ethyl 4-bromobutanoate (2.13 ml, 14.91 mmol). After stirring at rt for 3 h, the reaction mixture was diluted with water (200 ml) and extracted with EtOAc (2×100 ml). The combined organic layers were dried over Na$_2$SO$_4$ and concentrated under reduced pressure. The crude product was purified by column chromatography (silica gel 100-200 mesh) using 0-40% EtOAc in petroleum ether to give the title compound 1c-5 as a pale yellow solid (2.1 g, 58% yield). LCMS [M+H]$^+$ 292.

4-((1-Methyl-4-oxo-1,2,3,4-tetrahydroquinolin-7-yl)oxy)butanoic acid (1c-6)

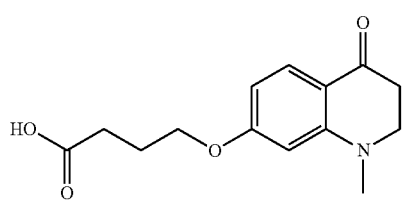

To a stirred solution of ethyl 4-((1-methyl-4-oxo-1,2,3,4-tetrahydroquinolin-7-yl)oxy)butanoate 1c-5 (2.1 g, 7.215 mmol) in THF/MeOH/H$_2$O (30/10/20 ml) was added lithium hydroxide monohydrate (0.680 g, 14.430 mmol) then it was stirred at rt for an additional 16 h. The reaction mixture was concentrated under reduced pressure. The resulting residue was acidified with 2N HCl (20 ml). The solid that has precipitated was filtered and washed with diethyl ether (50 ml) to give the title compound 1c-6 as a pale yellow solid (1.7 g, 89.5% yield). $^1$H NMR (400 MHz, DMSO-d6) β=12.1 (s, 1H), 7.62 (d, J=8.8 Hz, 1H), 6.31 (dd, J=2.4 Hz, J=8.8 Hz, 1H), 6.23 (d, J=2.0 Hz, 1H), 4.05 (t, J=6.2 Hz, 2H), 3.41 (t, J=7 Hz, 2H), 2.93 (s, 3H), 2.54 (t, J=7 Hz, 2H), 2.37 (t, J=7.2 Hz, 2H), 1.93 (t, J=7 Hz, 2H); LCMS [M+H]$^+$ 264.

Scheme (5)

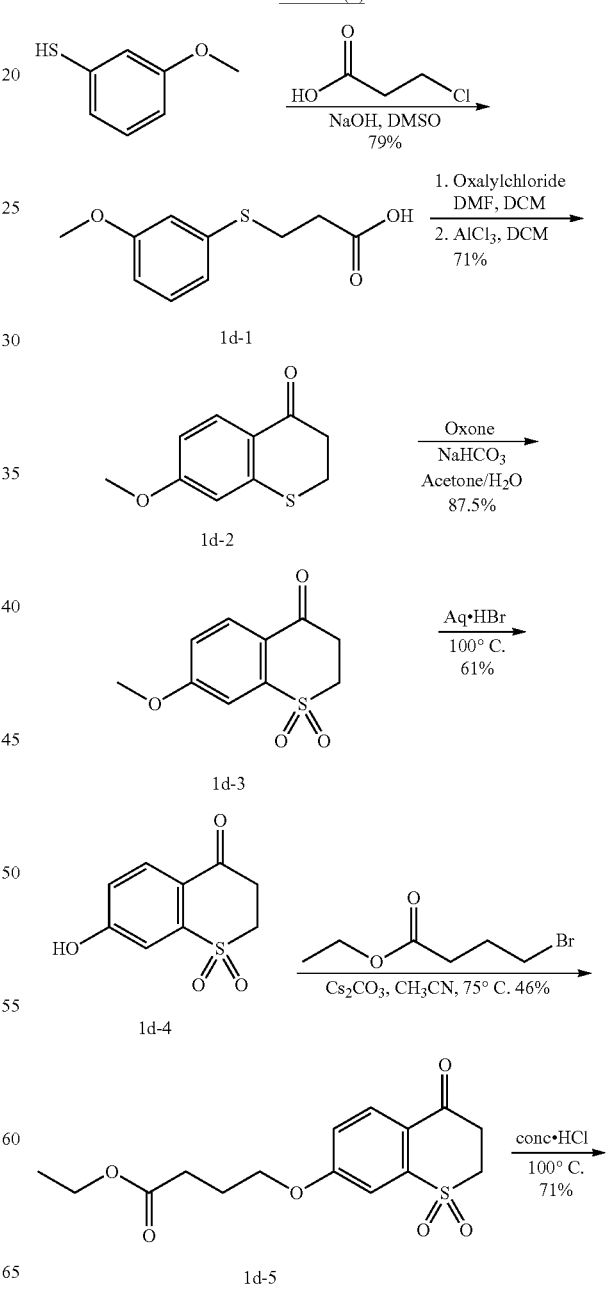

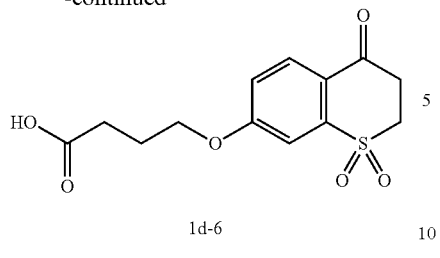

1d-6

3-((3-Methoxyphenyl)thio)propanoic acid (1d-1)

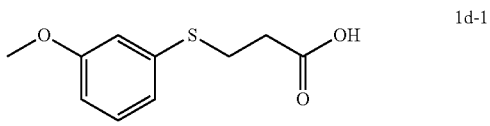

1d-1

To a stirred solution of 3-methoxybenzenethiol (10 g, 71.42 mmol) in DMSO (130 ml), was added NaOH powder (14.2 g, 357.1 mmol) followed by a solution of 3-chloropropanoic acid (8.1 g, 75 mmol) in DMSO (30 ml). The mixture was stirred at rt for 48 h under argon atmosphere. The reaction mixture was diluted with water (500 ml) and extracted with EtOAc (2×500 ml). The separated organic layers were dried over sodium sulfate and concentrated down to give the title compound 1d-1 as a brown gummy liquid (12 g, 79% yield). LCMS [M+H]$^+$ 213.

7-Methoxythiochroman-4-one (1d-2)

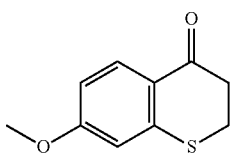

1d-2

To a stirred solution of 3-((3-methoxyphenyl)thio)propanoic acid 1d-1 (12 g, 58.9 mmol) in DCM (120 ml) were added oxalylchloride (8 ml, 55 mmol) and a catalytic amount of DMF (0.5 ml). The reaction mixture was stirred for 30 min and concentrated to dryness. The residue was dissolved in DCM (30 ml) and was added dropwise to a suspension of aluminum chloride (7.5 g, 56.5 mmol) in DCM (300 ml). The reaction mixture was stirred for 30 min upon which TLC analysis indicated formation of a less polar product. The reaction mixture was poured into ice cold water and extracted with DCM (2×500 ml). The combined organic layers were washed with brine (200 ml), dried over sodium sulfate and concentrated down. The crude product was purified by column chromatography (silica gel 100-200 mesh) using 0-15% EtOAc in petroleum ether to give the title compound 1d-2 as an off-white solid (8.1 g, 71% yield). LCMS [M+H]$^+$ 195.

7-Methoxythiochroman-4-one 1,1-dioxide (1d-3)

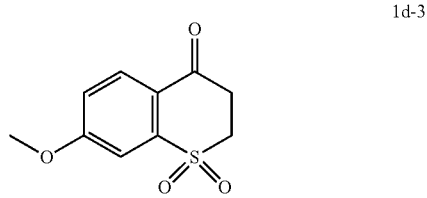

1d-3

To a stirred solution of 7-methoxythiochroman-4-one 1d-2 (7.5 g, 35.37 mmol) in acetone/water (80/80 ml) was added oxone (43.57 g, 141.57 mmol). The solution was cooled to 0° C. then solid sodium bicarbonate (17.82 g, 212.22 mmol) was added portion wise. It was allowed to warm to rt then stirred for an additional 3 h. The reaction mixture was diluted with water (500 ml) and extracted with EtOAc (2×500 ml). The combined organic layers were concentrated down. The resulting crude product was washed with n-pentane and dried under vacuum to give the title compound 1d-3 as an off-white solid (7.0 g, 87.5% yield). LCMS [M+H]$^+$ 227.

7-Hydroxythiochroman-4-one 1,1-dioxide (1d-4)

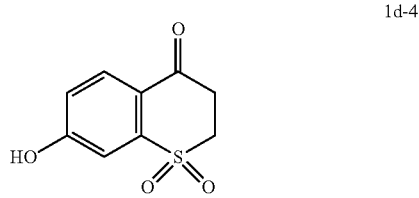 [SMILES: O=C1CCS(=O)(=O)c2cc(O)ccc21]

1d-4

A stirred solution of 7-methoxythiochroman-4-one 1,1-dioxide 1d-3 (7.0 g, 30.97 mmol) in 48% aq.HBr (200 ml) was heated at 100° C. for 48 h. The reaction mixture was cooled down and poured into water (500 ml). The aqueous layer was extracted with EtOAc (2×500 ml). The combined organic layers were concentrated down. The crude product was purified by column chromatography (silica gel 100-200 mesh) using 0-50% EtOAc in petroleum ether to give the title compound 1d-4 as a pale brown solid (4.0 g, 61% yield). LCMS [M+H]$^+$ 213.

Ethyl 4-((1,1-dioxido-4-oxothiochroman-7-yl)oxy)butanoate (1d-5)

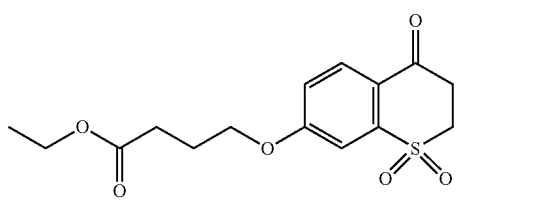

1d-5

A stirred solution of 7-hydroxythiochroman-4-one 1,1-dioxide 1d-4 (1.2 g, 5.66 mmol) in AcCN (20 ml) was cooled to 0° C. then cesium carbonate (2.9 g, 9.0 mmol) was added followed by ethyl 4-bromobutanoate (1.6 ml, 11.32 mmol). The resulting mixture was heated at 75° C. for 3 h. It was cooled to rt and diluted with water (200 ml). It was acidified with 2N HCl (10 ml) and extracted with EtOAc (2×500 ml). The combined organic layers were dried over Na$_2$SO$_4$ and concentrated under reduced pressure. The crude product was purified by column chromatography (silica gel 100-200 mesh) using 0-40% EtOAc in petroleum ether to give the title compound 1d-5 as an off-white solid (0.85 g, 46% yield). LCMS [M+H]$^+$ 327.

4-((1,1-Dioxido-4-oxothiochroman-7-yl)oxy)butanoic acid (1d-6)

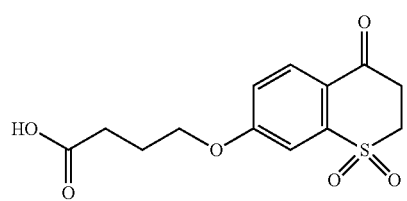

1d-6

A stirred solution of ethyl 4-((1,1-dioxido-4-oxothiochroman-7-yl)oxy)butanoate 1d-5 (0.85 g, 2.60 mmol) in conc.HCl (15 ml) was heated at 100° C. for 1 h upon which TLC analysis indicated the formation of a more polar compound. The reaction mixture was cooled to rt, diluted with water (200 ml) then extracted with EtOAc (2×500 ml). The combined organic layers were dried over Na$_2$SO$_4$ and concentrated under reduced pressure. The resulting crude solid was washed with diethyl ether then dried under vacuum to give the title compound 1d-6 as a pale pink solid (0.550 g, 71% yield). $^1$H NMR (400 MHz, DMSO-d6) β=12.20 (br s, 1H), 7.98 (d, J=8.8 Hz, 1H), 7.40-7.30 (m, 2H), 4.20 (t, J=6.4 Hz, 2H), 4.00 (t, J=6.2 Hz, 2H), 3.18 (t, J=6.2 Hz, 2H), 2.40 (t, J=7.4 Hz, 2H), 2.52 (t, J=7.2 Hz, 2H), 2.03-1.92 (m, 2H); LCMS [M+H]$^+$ 299.

Scheme (6)

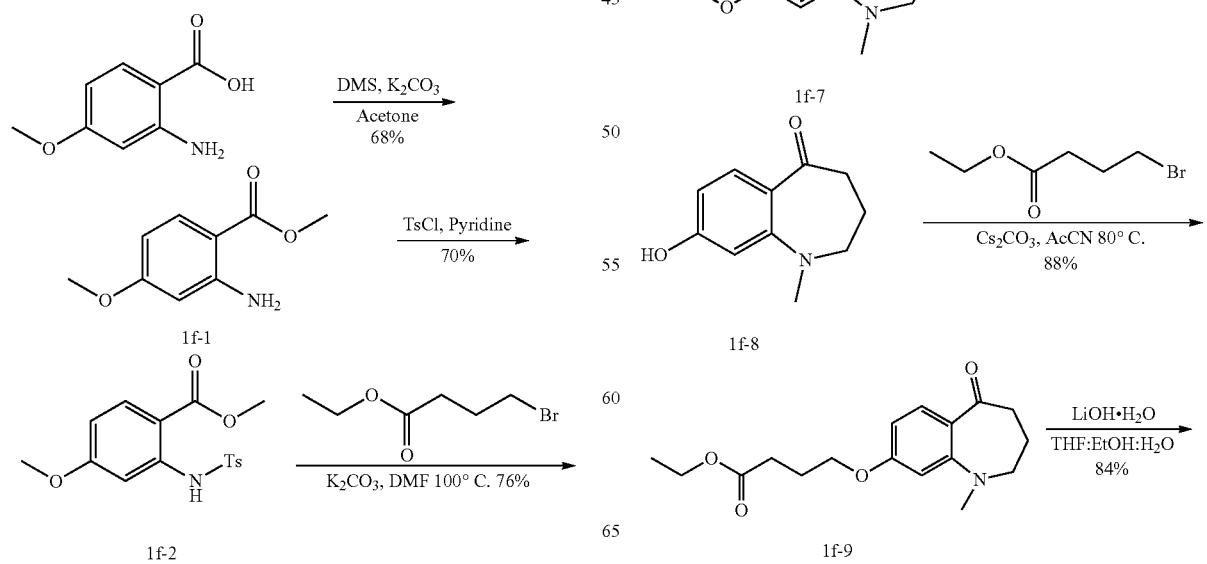

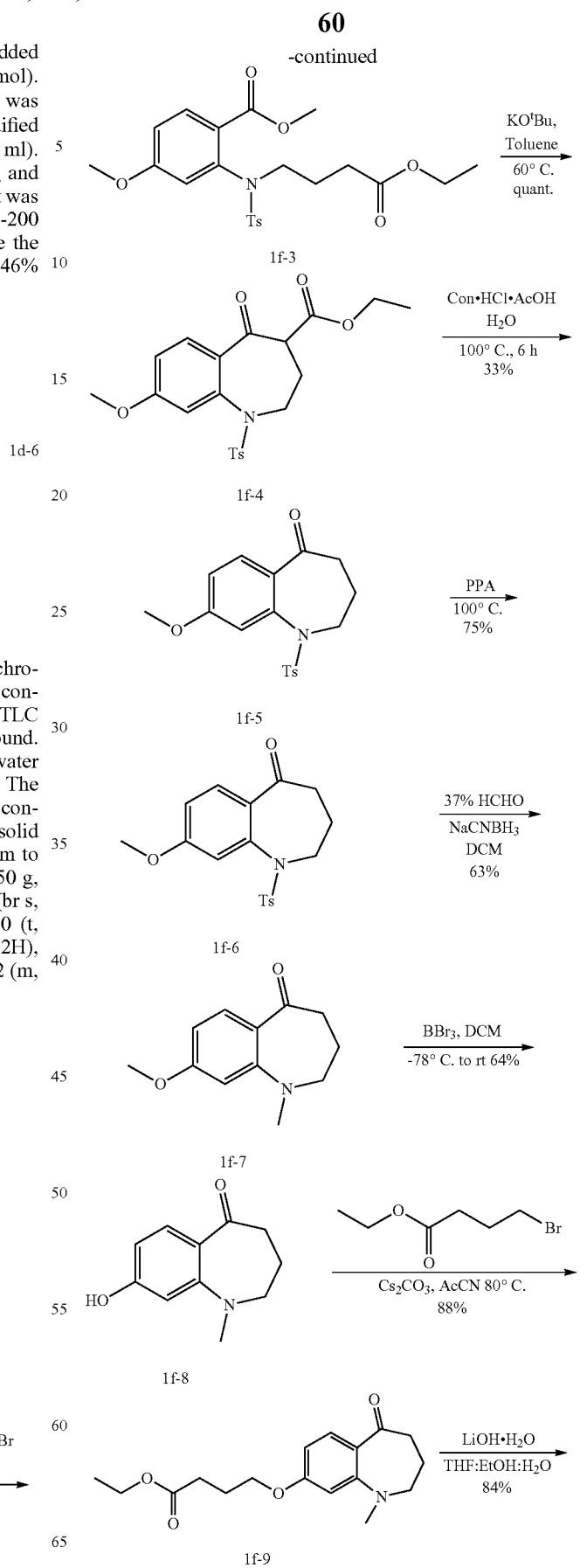

-continued

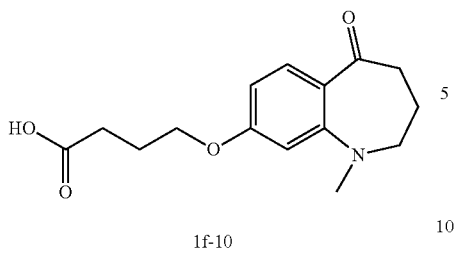

1f-10

Methyl 2-amino-4-methoxybenzoate (1f-1)

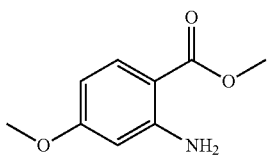

1f-1

To a suspension of compound 2-amino-4-methoxybenzoic acid (10 g, 59.8 mmol) in acetone (110 ml) was added $K_2CO_3$ (12.3 g, 89.7 mmol) followed by dimethyl sulfide (7.1 ml, 71.7 mmol) under argon atmosphere. The reaction mixture was stirred at room temperature for 3 h. It was diluted with $H_2O$ then extracted with ethyl acetate (2×200 ml). The combined organic layer was dried over $Na_2SO_4$ then concentrated under reduced pressure. The crude compound was purified by column chromatography using silica gel (100-200 mesh), (eluent 0-30% EtOAc in petroleum ether) to afford the title compound 1f-1 as a pale brown solid (7 g, 68% yield). LCMS $[M+H]^+$ 182.

Methyl 4-methoxy-2-((4-methylphenyl)sulfonamido)benzoate (1f-2)

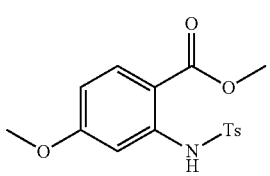

1f-2

To a stirred solution of compound if-1 (7 g, 38.6 mmol) in pyridine (80 ml) was slowly added TsCl (8.8 g, 46.6 mmol) at rt. This solution was further stirred for 16 h. The reaction mixture was poured into cold water upon which a solid was formed. The precipitate was filtered off and washed with n-pentane (50 ml) to afford the title compound if-2 as an off-white solid (10.8 g, 70% yield). LCMS $[M+H]^+$ 336.

Methyl 2-((N-(4-ethoxy-4-oxobutyl)-4-methylphenyl)sulfonamido)-4-methoxybenzoate (1f-3)

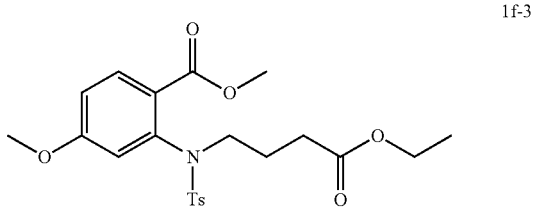 [SMILES: CCOC(=O)CCCN(c1cc(OC)ccc1C(=O)OC)S(=O)(=O)c1ccc(C)cc1]

1f-3

To a stirred solution of compound if-2 (10.8 g, 32.2 mmol) in DMF (100 ml) was slowly added $K_2CO_3$ (12.5 g, 87 mmol) followed by ethyl 4-bromobutanoate (5 ml, 35.5 mmol). The mixture was heated at 100° C. overnight. It was cooled down, diluted with cold water then extracted with ethyl acetate (2×200 ml). The combined organic layer was dried over with $Na_2SO_4$ and concentrated under reduced pressure. The crude compound was purified by column chromatography using silica gel (100-200 mesh), (eluent: 0-30% EtOAc in petroleum ether) to afford the title compound if-3 as an off-white solid (7 g, 68% yield). LCMS $[M+H]^+$ 450.

Ethyl 8-methoxy-5-oxo-1-tosyl-2,3,4,5-tetrahydro-1H-benzo[b]azepine-4-carboxylate (1f-4)

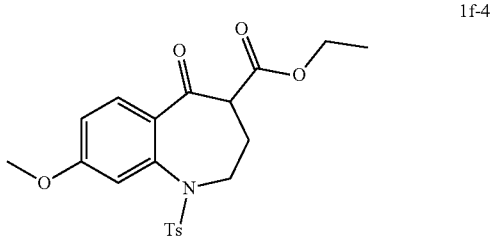 [SMILES: CCOC(=O)C1CCN(S(=O)(=O)c2ccc(C)cc2)c2cc(OC)ccc2C1=O]

1f-4

To a stirred solution of KOtBu (10.2 g, 45.6 mmol) in anhydrous toluene (200 ml) at 70° C., was added compound if-3 (10.25 g, 22.8 mmol) portion wise. After the addition was complete, the reaction mixture was heated under reflux for 2 h then cooled tort. It was diluted with cold water and extracted with ethyl acetate (2×200 ml). The combined organic layer was dried over with $Na_2SO_4$ and concentrated under reduced pressure to afford the title compound if-4 as a pale brown gummy liquid (8.3 g, quant). LCMS $[M+H]^+$ 418.

8-Methoxy-1-tosyl-1,2,3,4-tetrahydro-5H-benzo[b]azepin-5-one (1f-5)

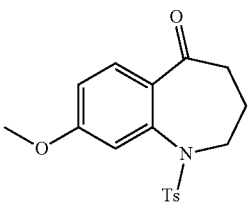

1f-5

To a stirred solution of compound if-4 (8.3 g, 20.1 mmol) in AcOH (35 ml) were added conc.HCl (15 ml) and water (10 ml). This mixture was heated to 100° C. for 6 h then cooled to rt. It was diluted with cold water and extracted with ethyl acetate (2×200 ml). The combined organic layer was dried over with Na$_2$SO$_4$ and concentrated under reduced pressure. The crude compound was purified by column chromatography using (silica gel 230-400 mesh, eluent: 0-30% EtOAc in petroleum ether) to afford the title compound if-5 as a pale yellow gummy liquid (2.6 g, 33% yield). LCMS [M+H]$^+$ 346.

8-Methoxy-1,2,3,4-tetrahydro-5H-benzo[b]azepin-5-one (1f-6)

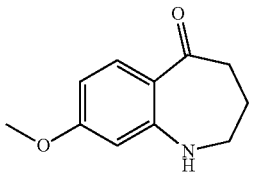

1f-6

A solution of compound if-5 (2.6 g, 6.2 mmol) in PPA (26 g) was stirred at 100° C. for 2 h before being cooled to rt. The reaction mixture was diluted with cold water and extracted with ethyl acetate (2×100 ml). The combined organic layer was dried over with Na$_2$SO$_4$ and concentrated under reduced pressure. The crude product was washed with diethyl ether (15 ml) to afford the title compound if-6 as a pale green solid (900 mg, 75% yield). LCMS [M+H]$^+$ 192.

8-Methoxy-1-methyl-1,2,3,4-tetrahydro-5H-benzo[b]azepin-5-one (1f-7)

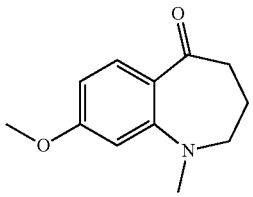

1f-7

To a suspension of compound if-6 (1.1 g, 5.7 mmol) in DCM:AcOH (10 ml: 2 ml) was added HCHO (37%, 1.8 mL, 23 mmol) at rt under argon atmosphere. The reaction mixture was stirred at rt for 2 h upon which it was cooled to 0° C. NaCNBH$_3$ (1.45 g, 23 mmol) was added portion wise, then the solution was slowly warmed to rt and stirred for 16 h. The solvents were removed under reduced pressure then the concentrate was basified with a saturated NaHCO$_3$ solution. This solution was extracted with ethyl acetate (2×50 ml). The combined organic layer was dried over Na$_2$SO$_4$ and concentrated under reduced pressure. The crude compound was purified by column chromatography using silica gel (100-200 mesh), (eluent: 0-20% EtOAc in petroleum ether) to afford the title compound if-7 as a pale brown gummy liquid (750 mg, 63% yield). LCMS [M+H]$^+$ 206.

8-Hydroxy-1-methyl-1,2,3,4-tetrahydro-5H-benzo[b]azepin-5-one (1f-8)

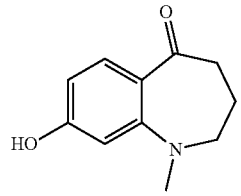

1f-8

A suspension of compound if-7 (700 mg, 3.4 mmol) in dry DCM (10 ml) was cooled to −78° C. then BBr$_3$ (17 ml, 17 mmol) was added. It was slowly warmed to rt then was stirred for 6 h. The reaction mixture was basified with a saturated NaHCO$_3$ solution and extracted with DCM (2×50 ml). The combined organic layer was dried over Na$_2$SO$_4$ and concentrated under reduced pressure. The crude product was washed with diethyl ether (10 ml) to afford the title compound if-8 as a pale green solid (420 mg, 64% yield). LCMS [M+H]$^+$ 192.

Ethyl 4-((1-methyl-5-oxo-2,3,4,5-tetrahydro-1H-benzo[b]azepin-8-yl)oxy)butanoate (1f-9)

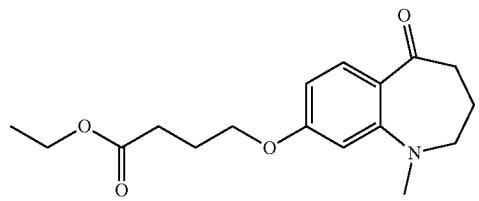

1f-9

To a stirred solution of compound if-8 (360 mg, 1.9 mmol) in AcCN (6 ml) was slowly added Cs$_2$CO$_3$ (920 mg, 2.8 mmol) followed by ethyl 4-bromobutanoate (0.32 ml, 2.25 mmol). The mixture was heated at 80° C. for 16 h then cooled to rt. It was diluted with cold water and extracted with ethyl acetate (2×20 ml). The combined organic layer was dried over Na$_2$SO$_4$ and concentrated under reduced pressure. The crude product was purified by column chromatography using silica gel (100-200 mesh), (eluent: 0-30% EtOAc in petroleum ether) to afford the title compound if-9 as a pale brown gummy liquid (450 mg, 88% yield). LCMS [M+H]$^+$ 306.

4-((1-Methyl-5-oxo-2,3,4,5-tetrahydro-1H-benzo[b]azepin-8-yl)oxy)butanoic acid (1f-10)

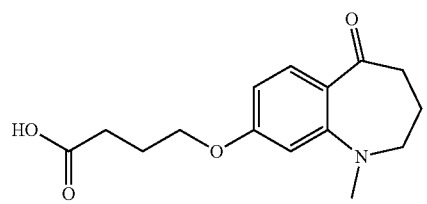

1f-10

To a stirred solution of compound if-9 (500 mg, 1.6 mmol) in THF:MeOH:H$_2$O (8 ml: 5 ml: 2 ml) was added LiOH.H$_2$O (125 mg, 3.3 mmol) then the resulting mixture was stirred at rt for 16 h. The volatiles were removed under reduced pressure. The concentrate was acidified with a solution of HCl (2N, 3 ml) then extracted with EtOAc (2×50 ml). The combined organic layer was dried over Na$_2$SO$_4$ and concentrated under reduced pressure. The residue was triturated with diethyl ether (5 ml), filtered then dried to afford the title compound if-10 as a pale green solid (380 g, 84% yield). $^1$H NMR (400 MHz, DMSO-d6) δ=12.20 (s, 1H), 7.52 (d, J=8.8 Hz, 1H), 6.41-6.35 (m, 2H), 4.03 (t, J=6.4 Hz, 2H), 3.15 (t, J=6.4 Hz, 2H), 3.05 (s, 3H), 2.57 (t, J=6.8 Hz, 2H), 2.37 (t, J=7.2 Hz, 2H), 2.15-2.04 (m, 2H), 1.98-1.87 (m, 2H); LCMS [M+H]$^+$ 278.

The synthesis of 3-mercapto-3-methylbutanehydrazide (1-3) is described in Scheme (7) using protocols similar to ones described previously[49].

Scheme (7)

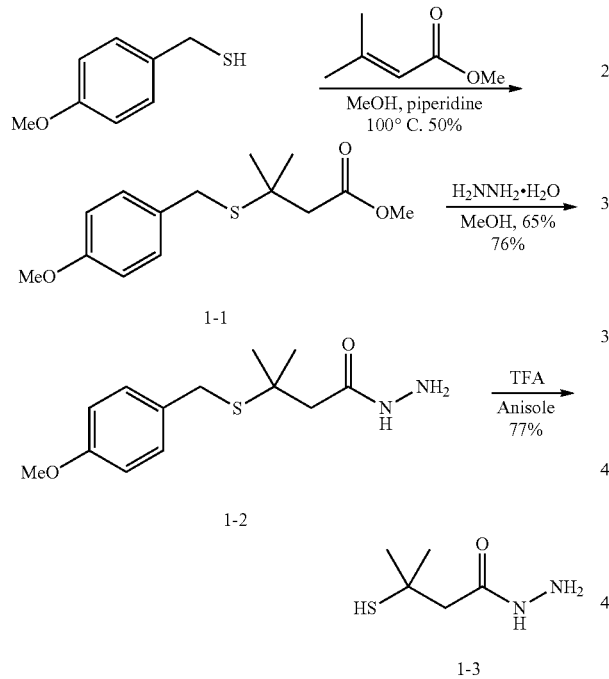

Methyl 3-((4-methoxybenzyl)thio)-3-methylbutanoate (1-1)

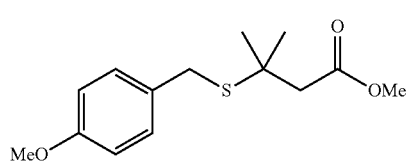 [SMILES: COC(=O)CC(C)(C)SCc1ccc(OC)cc1]

To a solution of methyl 3-methylbut-2-enoate (1.48 g, 13.0 mmol) in methanol (50 ml) was added 4-methoxy-α-toluenethiol (1 g, 6.5 mmol) and piperidine (55 mg, 0.65 mmol). The reaction was heated to reflux at 100° C. for 70 hours, after which it was concentrated under reduced pressure. The crude mixture was purified using Biotage™ (50 g silica column; eluent: EtOAc/Hexanes 0-10% then 10%). The fractions containing the product were collected and concentrated under reduced pressure to yield the title compound 1-1 as a clear oil (0.96 g, 50% yield). $^1$H NMR (500 MHz, DMSO-d6) δ=7.22 (d, J=8.7 Hz, 2H), 6.85 (d, J=8.7 Hz, 2H), 3.75 (s, 2H), 3.72 (s, 3H), 3.60 (s, 3H), 2.62 (s, 2H), 1.37 (s, 6H); LCMS [M+Na]$^+$291.

3-((4-Methoxybenzyl)thio)-3-methylbutanehydrazide (1-2)

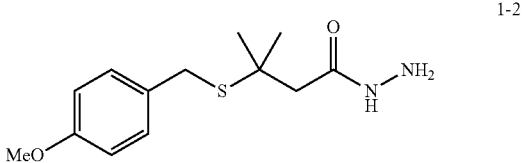 [SMILES: COc1ccc(CSC(C)(C)CC(=O)NN)cc1]

To a solution of compound 1-1 (1.76 g, 6.6 mmol) in methanol (4.5 ml) was added hydrazine monohydrate (1.64 g, 32.8 mmol). The reaction was heated to 65° C. for 20 hours, after which it was concentrated under reduced pressure. The crude residue was purified using Biotage™ (25 g silica column; eluent: EtOAc/hexanes; 10-100% then 100%). The fractions containing the product were concentrated under reduced pressure to yield compound 1-2 as a white powder (1.4 g, 76% yield). $^1$H NMR (500 MHz, DMSO-d$_6$) δ=9.02 (s, 1H), 7.23 (d, J=8.7 Hz, 2H), 6.85 (d, J=8.7 Hz, 2H), 4.20 (d, J=4.1 Hz, 2H), 3.74 (s, 2H), 3.72 (s, 3H), 2.34 (s, 2H), 1.36 (s, 6H); LCMS [M+H]$^+$ 269.

3-Mercapto-3-methylbutanehydrazide (1-3)

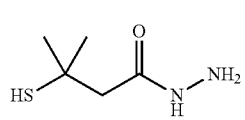

To a 100 ml round bottom flask was added a solution of compound 1-2 (250 mg, 0.93 mmol) in trifluoroacetic acid (8 ml). The reaction was cooled to 0° C. in an ice bath, after which anisole (0.15 ml, 1.40 mmol) was added. The reaction was then warmed to room temperature and allowed to stir for 24 h, after which it was concentrated via steady stream of nitrogen. The crude residue was purified by anion exchange chromatography using a PoraPak Rxn CX™ 20 cc (2 g) cartridge. The column was first flushed with MeOH then the crude reaction mixture was loaded onto the resin using ethyl acetate. 50 ml of MeOH was flushed through the column, followed by 50 ml of a 95% MeOH/5% NH$_4$OH (28% in water) mixture. The fractions containing the product were concentrated under reduced pressure, then dried via a steady stream of nitrogen to yield the title compound 1-3 as an oil that solidified upon standing (113 mg, 77% yield). $^1$H NMR (500 MHz, DMSO-d$_6$) δ=9.00 (s, 1H), 4.21 (s, 2H), 3.04 (s, 1H), 2.34 (s, 2H), 1.40 (s, 6H); LCMS [M+H]$^+$ 149.

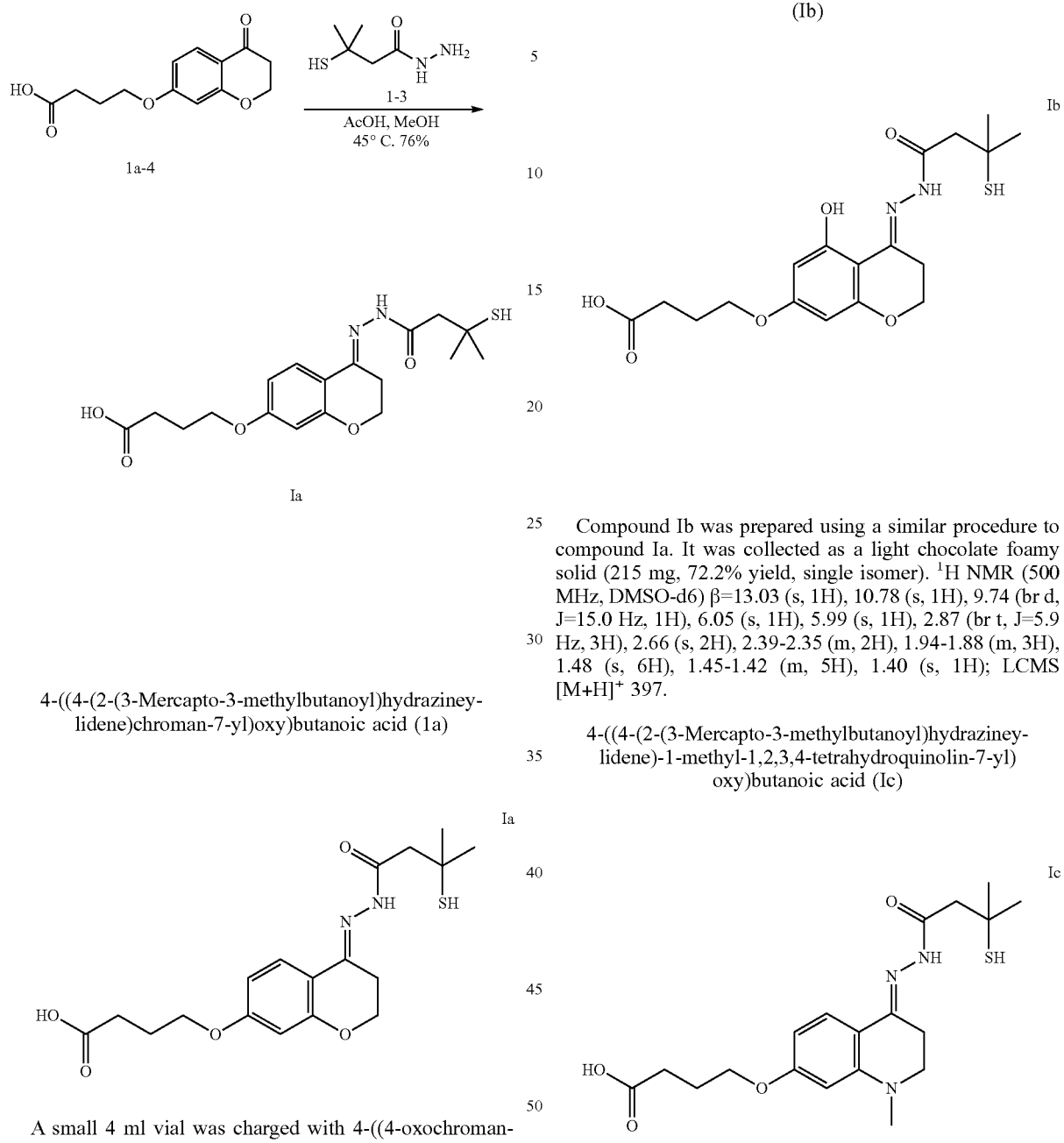

4-((4-(2-(3-Mercapto-3-methylbutanoyl)hydraziney-lidene)chroman-7-yl)oxy)butanoic acid (Ia)

A small 4 ml vial was charged with 4-((4-oxochroman-7-yl)oxy)butanoic acid 1a-4 (300 mg, 1.2 mmol) and 3-mercapto-3-methylbutanehydrazide 1-3 (195 mg, 1.319 mmol) then methanol (10 ml). The mixture was heated at 45° C. overnight after which LCMS showed that only a small amount of starting material was remaining. The reaction was stopped. The mixture was loaded onto celite and dried. The crude reaction mixture was purified by chromatography using Isco (12 g silica column: eluent MeOH/DCM 0, 0-5% then 5%) to give the compound Ia as an off-white powder (346 mg, 76% yield, 2 isomers). $^1$H NMR (500 MHz, DMSO-d6) β=12.89-11.40 (m, 1H), 10.44 (s, 1H), 10.27 (s, 1H), 7.83 (br dd, J=5.2, 8.4 Hz, 1H), 6.61 (br t, J=7.8 Hz, 1H), 6.47-6.40 (m, 1H), 4.29-4.17 (m, 2H), 3.99 (br s, 2H), 3.07-3.01 (m, 1H), 2.78 (br d, J=5.7 Hz, 2H), 2.63 (s, 1H), 2.42-2.30 (m, 2H), 1.93 (br t, J=6.6 Hz, 2H), 1.49 (s, 3H), 1.47 (s, 3H); LCMS [M+H]$^+$ 381.

4-((5-Hydroxy-4-(2-(3-mercapto-3-methylbutanoyl)hydrazineylidene)chroman-7-yl)oxy)butanoic acid (Ib)

Compound Ib was prepared using a similar procedure to compound Ia. It was collected as a light chocolate foamy solid (215 mg, 72.2% yield, single isomer). $^1$H NMR (500 MHz, DMSO-d6) β=13.03 (s, 1H), 10.78 (s, 1H), 9.74 (br d, J=15.0 Hz, 1H), 6.05 (s, 1H), 5.99 (s, 1H), 2.87 (br t, J=5.9 Hz, 3H), 2.66 (s, 2H), 2.39-2.35 (m, 2H), 1.94-1.88 (m, 3H), 1.48 (s, 6H), 1.45-1.42 (m, 5H), 1.40 (s, 1H); LCMS [M+H]$^+$ 397.

4-((4-(2-(3-Mercapto-3-methylbutanoyl)hydrazineylidene)-1-methyl-1,2,3,4-tetrahydroquinolin-7-yl)oxy)butanoic acid (Ic)

Compound Ic was prepared using a similar procedure to compound Ia. It was collected as a very light yellow powder (181 mg, 60.6% yield, 2 isomers). $^1$H NMR (500 MHz, DMSO-d$_6$) β=12.15 (br d, J=2.7 Hz, 1H), 10.23 (s, 1H), 10.10 (s, 1H), 7.83 (br dd, J=8.9, 13.8 Hz, 1H), 6.39-6.32 (m, 1H), 6.23 (s, 1H), 4.00 (br s, 2H), 3.21-3.07 (m, 2H), 3.05-3.00 (m, 1H), 2.86 (s, 2H), 2.84 (s, 1H), 2.69 (br d, J=4.2 Hz, 2H), 2.60 (s, 1H), 2.38 (br t, J=7.0 Hz, 2H), 1.98-1.89 (m, 2H), 1.48 (s, 3H), 1.46 (s, 3H); LCMS [M+H]$^+$ 394.

4-((4-(2-(3-Mercapto-3-methylbutanoyl)hydraziney-lidene)-1,1 dioxidothiochroman-7-yl)oxy)butanoic acid (Id)

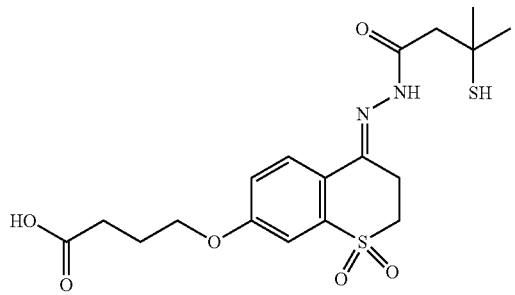

Compound Id was prepared using a similar procedure to compound Ia. It was collected as an off-white powder (53 mg, 18.3% yield, 2 isomers). $^1$H NMR (DMSO-d$_6$, 500 MHz) β=12.0-12.4 (m, 1H), 10.78 (s, 1H), 10.53 (s, 1H), 8.11 (br t, 1H, J=9.1 Hz), 7.3-7.3 (m, 1H), 7.2-7.3 (m, 1H), 4.13 (br t, 2H, J=6.3 Hz), 3.75 (br t, 1H, J=6.0 Hz), 3.69 (br t, 1H, J=5.9 Hz), 3.2-3.2 (m, 2H), 3.09 (s, 1H), 2.70 (s, 1H), 2.41 (br t, 2H, J=7.0 Hz), 1.97 (br t, 2H, J=6.7 Hz), 1.50 (s, 3H), 1.48 (s, 3H); LCMS [M+H]$^+$ 429.

4-((5-(2-(3-Mercapto-3-methylbutanoyl)hydraziney-lidene)-1-methyl-2,3,4,5-tetrahydro-1H-benzo[b]azepin-8-yl)oxy)butanoic acid (If)

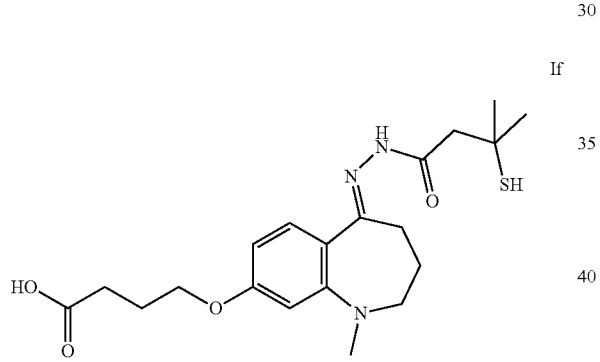

Compound If was prepared using a similar procedure to compound Ia. It was collected as a yellow powder (230.8 mg, 69.8% yield, 2 isomers). $^1$H NMR (DMSO-d6, 500 MHz) δ 10.37 (s, 1H), 10.13 (s, 1H), 7.3-7.4 (m, 1H), 6.42 (dt, 1H, J=2.0, 8.7 Hz), 6.34 (s, 1H), 3.98 (br t, 2H, J=6.3 Hz), 3.0-3.1 (m, 5H), 2.86 (s, 2H), 2.85 (s, 1H), 2.6-2.7 (m, 3H), 2.4-2.4 (m, 2H), 2.34 (s, 1H), 1.8-2.0 (m, 5H), 1.47 (s, 3H), 1.46 (s, 3H), 1.40 (s, 3H); LCMS [M+H]$^+$ 408.

Synthesis of Linker-DM1 Constructs

The representative linkers are conjugated to DM1 via a disulfide bond formation reaction according to the synthetic procedures described in schemes (9) and (10). DM1 was reacted with 2,2'-dithiobis(5-nitropyridine) to form the DM1-thio(5-nitropyridine) compound 2-1. This intermediate was then reacted with thiol of linkers (for example: Ia-1) to form the disulfide bond between the linker and DM1 which gave the final DM1 constructs (IVa, IVb, IVc, IVd, IVe and IVf) that are ready for antibody conjugation.

Activation of DM1

Scheme (9)

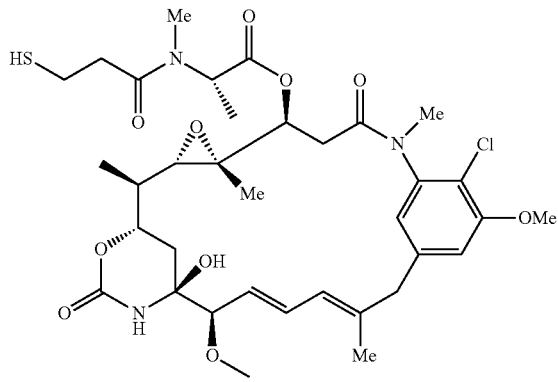

DM1

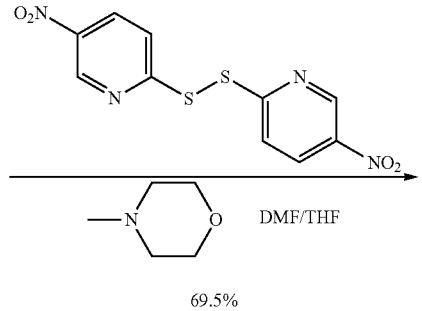

69.5%

-continued

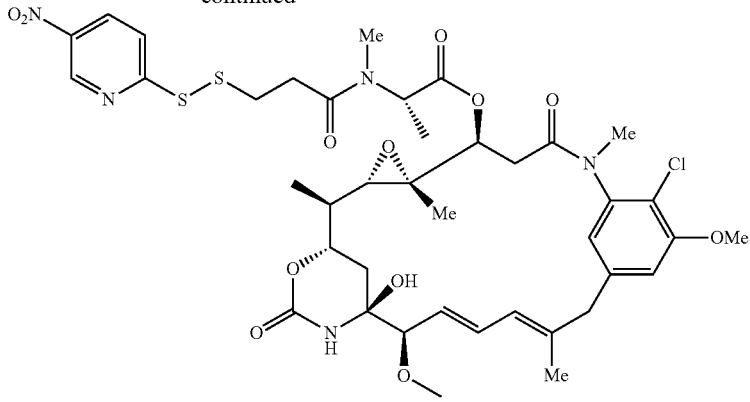

4-1

DM1-thio(5-nitropyridine) (4-1)

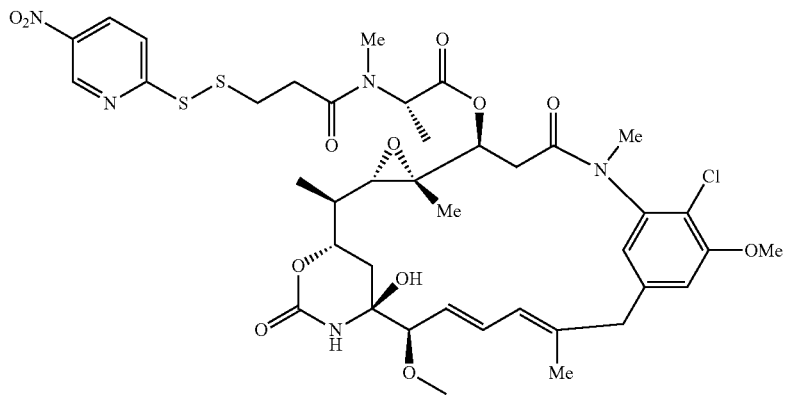

4-1

To a solution of 1,2-bis(5-nitropyridin-2-yl)disulfane (147 mg, 0.474 mmol) in THF (15 ml) was added 4-methylmorpholine (0.033 ml, 0.296 mmol). The mixture was stirred at room temperature upon which it was added to a solution of DM1 (175 mg, 0.237 mmol) in DMF (7.50 ml). The reaction mixture was stirred at room temperature for 90 min. LCMS showed that the reaction went to almost completion. Most of the THF was evaporated under reduced pressure. The resulting crude concentrate was diluted with EtOAc. The organic layer was washed with water (×3) then with brine. It was dried over $Na_2SO_4$ then concentrated. The crude product was purified by Isco (12 g silica column: eluent 0-100% then 100% EtOAc/Hexanes) to afford the title compound 4-1 as a light yellow powder (147 mg, 69.5% yield). $^1$H NMR (500 MHz, DMSO-d6) β=9.11-9.09 (m, 1H), 8.45 (dd, J=2.4, 8.9 Hz, 1H), 7.88 (d, J=8.9 Hz, 1H), 7.00 (s, 1H), 6.88 (s, 1H), 6.58-6.49 (m, 2H), 6.37-6.35 (m, 1H), 5.93 (s, 1H), 5.57 (br dd, J=9.2, 13.7 Hz, 1H), 5.30 (q, J=6.7 Hz, 1H), 4.52 (br dd, J=2.0, 12.0 Hz, 1H), 4.09-4.00 (m, 2H), 3.87 (s, 3H), 3.48 (br d, J=8.9 Hz, 1H), 3.25 (s, 3H), 3.19-3.13 (m, 1H), 3.08 (s, 3H), 3.08-3.03 (m, 1H), 3.02-2.89 (m, 2H), 2.78 (br d, J=9.5 Hz, 1H), 2.70 (s, 3H), 2.46-2.39 (m, 1H), 2.03-1.97 (m, 2H), 1.54 (s, 3H), 1.49-1.41 (m, 2H), 1.24 (br d, J=13.0 Hz, 1H), 1.17 (br d, J=6.8 Hz, 3H), 1.12 (br d, J=6.2 Hz, 3H), 0.75 (s, 3H); LCMS [M+H]$^+$ 893.

Scheme (10)
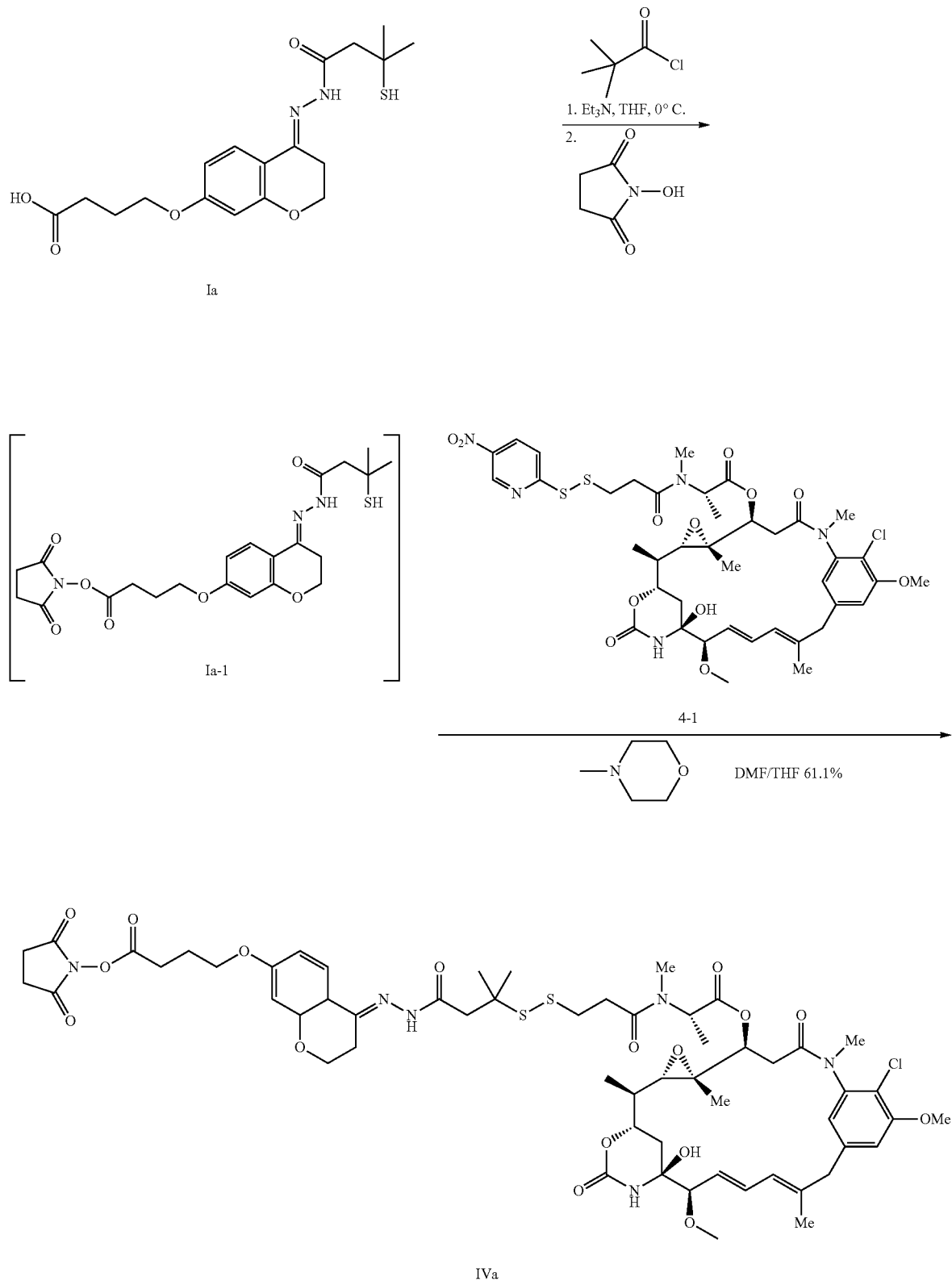

Heterocyclic Linker-DM1 Construct (IVa)

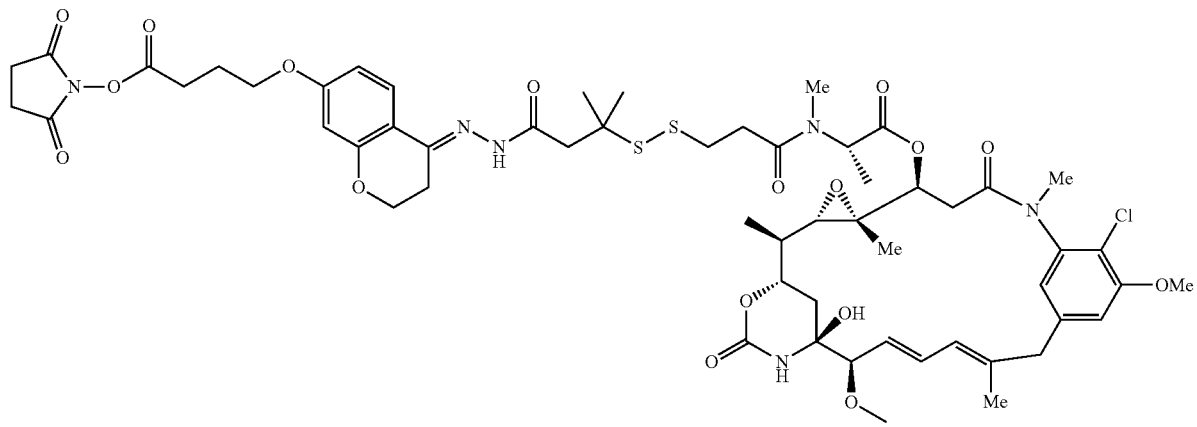

IVa

A 30 ml vial was charged with 4-((4-(2-(3-mercapto-3-methylbutanoyl)hydrazono)chroman-7-yl)oxy)butanoic acid Ia (30 mg, 0.079 mmol) then THF (3 ml) was added. The solution was stirred at 0° C. upon which triethylamine (0.022 ml, 0.158 mmol) followed by trimethylacetyl chloride (10.67 µl, 0.087 mmol) were added. After 30 min, N-hydroxysuccinimide (11.80 mg, 0.103 mmol) was added as a solid. The solution was stirred for 1 h upon which LCMS showed about (1:1) conversion. Triethylamine (0.022 ml, 0.158 mmol), trimethylacetyl chloride (10.67 µl, 0.087 mmol) and 6 mg of N-hydroxysuccinimide (6 mg) were added. After 1 h, there was still some starting material left. Additional triethylamine (0.020 ml), trimethylacetyl chloride (20 µl) and 6 mg of N-hydroxysuccinimide (11 mg) were added. The reaction mixture was stirred for 30 min upon which LCMS showed about 8% of starting material was left. The reaction was stopped. The $Et_3N.HCl$ salt was filtered through a frit. The frit was washed several times with THF. The filtrate was concentrated. The glassy residue was taken into hexanes. It was sonicated then vortexed. The hexanes was pipetted out. This process was repeated twice. The residue was dried under high vacuum to afford intermediate Ia-1 as a white semi-solid (56 mg crude). DM1-thio(5-nitropyridine) 4-1 (20 mg, 0.022 mmol) was dissolved in DMF (1.5 ml) then a solution of intermediate Ia-1 (42.8 mg, 0.090 mmol, crude) in THF (1.5 ml) was added. 4-Methylmorpholine (0.045 ml, 0.022 mmol, as a 0.5 M solution in of DMF) was added. The mixture was stirred at room temperature. After about 1 hour, LCMS showed that the reaction was complete. The crude mixture was separated between water and EtOAc and shaken. The organic layer was washed with water (×3) then brine. It was dried over $Na_2SO_4$ and concentrated. The crude product was purified by chromatography over Isco (4 g silica column; eluent: EtOAc/Hexanes; 0-100% then 100%). The product was taken into acetonitrile frozen then lyophilized to give the title compound IVa as a white fluffy powder (17.5 mg, 61.1% yield, 2 isomers). $^1$H NMR (500 MHz, DMSO-d6) β=10.47-10.29 (m, 1H), 10.21 (s, 1H), 7.82-7.71 (m, 1H), 7.11-7.03 (m, 1H), 6.81 (br d, J=6.1 Hz, 1H), 6.61-6.51 (m, 2H), 6.50-6.44 (m, 2H), 6.39 (br s, 1H), 5.85 (br d, J=4.9 Hz, 1H), 5.68 (s, 1H), 5.46 (td, J=7.9, 15.5 Hz, 1H), 5.24 (br d, J=6.1 Hz, 1H), 4.44 (br d, J=10.9 Hz, 1H), 4.19-4.10 (m, 2H), 3.99 (br d, J=6.8 Hz, 3H), 3.84 (br d, J=7.5 Hz, 3H), 3.45-3.35 (m, 2H), 3.17 (br d, J=7.6 Hz, 3H), 3.08 (br d, J=11.7 Hz, 3H), 2.90 (br s, 1H), 2.81-2.74 (m, 8H), 2.73-2.68 (m, 3H), 2.64 (br d, J=10.6 Hz, 3H), 2.04-1.94 (m, 3H), 1.50 (br d, J=12.0 Hz, 3H), 1.38 (br d, J=7.3 Hz, 3H), 1.15 (br s, 6H), 1.10 (br s, 3H), 1.05 (br d, J=5.9 Hz, 3H), 0.71 (br s, 3H); LCMS [M+H]$^+$ 1214.

Heterocyclic Linker-DM1 Construct (IVb)

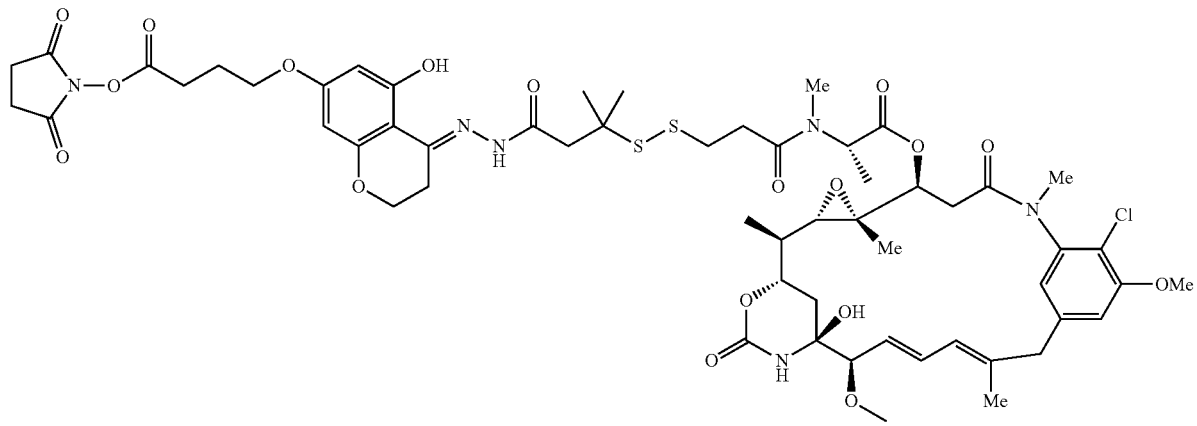

IVb

Heterocyclic linker-DM1 construct IVb was prepared according to a similar procedure to heterocyclic linker-DM1 IVa. It was collected as an off-white fluffy powder (15 mg, 49.0% yield, single isomer). $^1$H NMR (DMSO-d6, 500 MHz) δ=12.94 (br s, 1H), 10.72 (br s, 1H), 7.08 (s, 1H), 6.8-6.9 (m, 1H), 6.5-6.6 (m, 1H), 6.47 (s, 2H), 5.99 (br s, 1H), 5.94 (br s, 1H), 5.86 (s, 1H), 5.47 (br dd, 1H, J=8.9, 14.9 Hz), 5.25 (q, 1H, J=6.5 Hz), 4.45 (br d, 1H, J=13.0 Hz), 4.17 (br s, 3H), 4.0-4.0 (m, 1H), 3.96 (br t, 2H, J=6.2 Hz), 3.84 (s, 3H), 3.4-3.5 (m, 3H), 3.18 (s, 4H), 3.09 (s, 4H), 2.79 (br s, 4H), 2.75 (br s, 7H), 2.65 (s, 3H), 1.98 (br d, 4H, J=7.1 Hz), 1.52 (s, 3H), 1.3-1.4 (m, 5H), 1.16 (s, 6H), 1.10 (br d, 3H, J=6.5 Hz), 1.05 (br d, 3H, J=6.1 Hz), 0.72 (s, 3H); LCMS [M+H]$^+$ 1230.

Heterocyclic Linker-DM1 Construct (IVc)

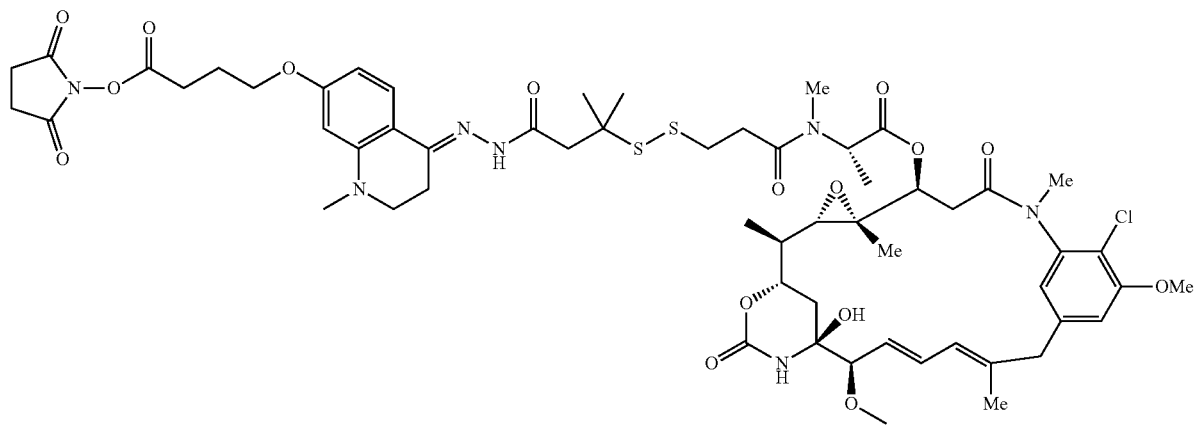

IVc

Heterocyclic linker-DM1 construct IVc was prepared according to a similar procedure to heterocyclic linker-DM1 IVa. It was collected as a light yellow fluffy powder (19 mg, 76% yield, 2 isomers). $^1$H NMR (500 MHz, DMSO-d6) β=10.18 (s, 1H), 10.05 (s, 1H), 7.78 (dd, J=8.7, 18.8 Hz, 1H), 7.11-7.00 (m, 1H), 6.86-6.78 (m, 1H), 6.59-6.43 (m, 3H), 6.31 (br dd, J=8.8, 15.8 Hz, 1H), 6.18 (br s, 1H), 5.86 (br d, J=4.3 Hz, 1H), 5.68 (br s, 1H), 5.46 (td, J=7.6, 15.0 Hz, 1H), 5.24 (br dd, J=3.2, 6.4 Hz, 1H), 4.44 (br d, J=9.9 Hz, 1H), 4.03-3.96 (m, 4H), 3.84 (br d, J=7.3 Hz, 3H), 3.44-3.36 (m, 2H), 3.17 (br d, J=6.6 Hz, 4H), 3.12-3.04 (m, 7H), 2.81-2.72 (m, 17H), 2.68-2.56 (m, 8H), 2.04-1.94 (m, 5H), 1.50 (br d, J=11.6 Hz, 3H), 1.43-1.33 (m, 5H), 1.22 (br d, J=5.6 Hz, 1H), 1.15 (br s, 6H), 1.14 (br s, 3H), 1.10 (br t, J=5.5 Hz, 3H), 1.05 (br d, J=5.9 Hz, 3H), 0.71 (br d, J=2.3 Hz, 3H); LCMS [M+H]$^+$ 1227.

Heterocyclic Linker-DM1 Construct (IVd)

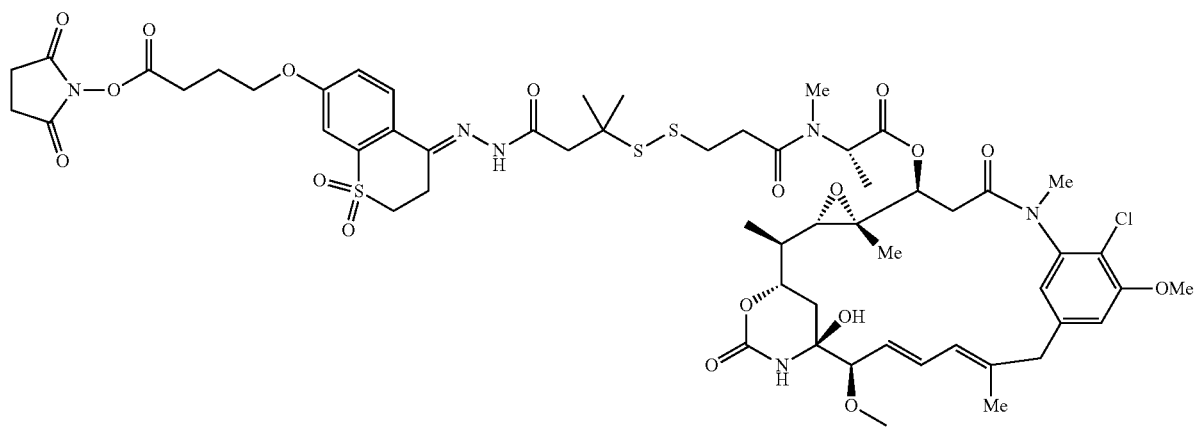

Heterocyclic linker-DM1 construct IVd was prepared according to a similar procedure to heterocyclic linker-DM1 IVa. It was collected as a white fluffy powder (17.3 mg, 58.0% yield, 2 isomers). $^1$H NMR (DMSO-d6, 500 MHz) δ 10.74 (s, 1H), 10.46 (s, 1H), 8.05 (dd, 1H, J=9.0, 19.1 Hz), 7.2-7.3 (m, 1H), 7.22 (br s, 1H), 7.0-7.1 (m, 1H), 6.81 (br d, 1H, J=5.6 Hz), 6.4-6.6 (m, 3H), 5.85 (br d, 1H, J=10.8 Hz), 5.45 (dt, 1H, J=9.1, 15.1 Hz), 5.24 (quin, 1H, J=6.5 Hz), 4.4-4.5 (m, 1H), 4.31 (br t, 1H, J=5.6 Hz), 4.12 (br d, 2H, J=2.3 Hz), 4.00 (br t, 1H, J=11.1 Hz), 3.83 (br d, 3H, J=6.6 Hz), 3.67 (br t, 1H, J=6.1 Hz), 3.63 (br t, 1H, J=6.3 Hz), 3.41 (br t, 1H, J=9.3 Hz), 3.17 (br d, 3H, J=9.4 Hz), 3.12 (br s, 1H), 3.08 (br d, 3H, J=9.0 Hz), 2.9-3.0 (m, 2H), 2.8-2.8 (m, 3H), 2.75 (br s, 4H), 2.64 (br d, 3H, J=10.3 Hz), 2.04 (quin, 2H, J=6.7 Hz), 1.9-2.0 (m, 1H), 1.52 (s, 1H), 1.48 (s, 2H), 1.3-1.4 (m, 3H), 1.16 (br s, 6H), 1.13 (s, 1H), 1.1-1.1 (m, 3H), 1.05 (br d, 3H, J=5.9 Hz), 0.71 (br d, 3H, J=5.6 Hz); LCMS [M+H]$^+$ 1261.

Acyclic Linker-DM1 Construct (IVe)

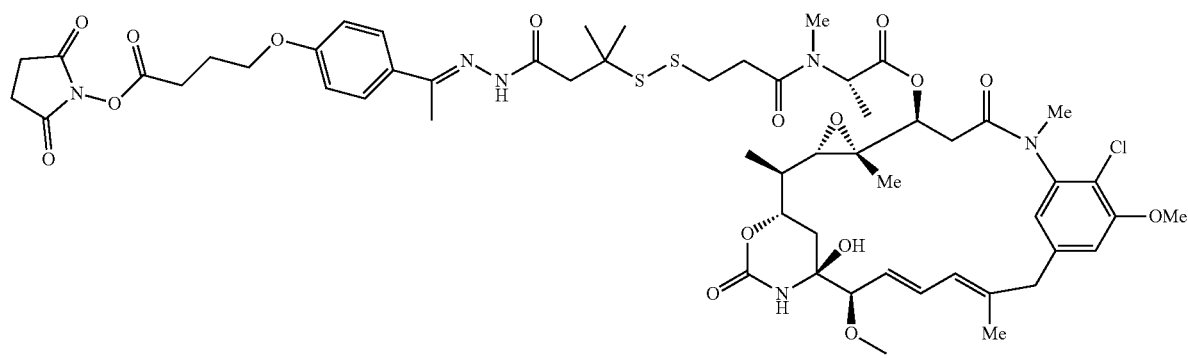

Acyclic linker-DM1 construct IVe was prepared according to a similar procedure to heterocyclic linker-DM1 IVa. It was collected as a white fluffy powder (16.92 mg, 85% yield, 2 isomers). $^1$H NMR (500 MHz, DMSO-d6) δ=10.39 (s, 1H), 10.23 (s, 1H), 7.78-7.71 (m, 2H), 7.18-7.11 (m, 1H), 7.03-6.95 (m, 2H), 6.89 (br d, J=6.1 Hz, 1H), 6.67-6.58 (m, 1H), 6.57-6.48 (m, 2H), 5.93 (br d, J=6.2 Hz, 1H), 5.76 (br s, 1H), 5.59-5.45 (m, 1H), 5.32 (br t, J=6.5 Hz, 1H), 4.56-4.48 (m, 1H), 4.12-4.03 (m, 4H), 3.91 (br d, J=5.6 Hz, 3H), 3.52-3.47 (m, 2H), 3.25 (br d, J=8.2 Hz, 3H), 3.17 (s, 1H), 3.13 (s, 2H), 2.96 (br d, J=13.3 Hz, 2H), 2.89-2.85 (m, 4H), 2.83 (br s, 4H), 2.71 (br d, J=18.0 Hz, 3H), 2.21 (br d, J=5.5 Hz, 3H), 2.13-2.02 (m, 4H), 1.58 (br d, J=14.4 Hz, 3H), 1.45 (br d, J=11.7 Hz, 4H), 1.24 (br s, 3H), 1.22 (br s, 3H), 1.17 (br t, J=6.4 Hz, 3H), 1.13 (br d, J=5.3 Hz, 3H), 0.79 (br d, J=4.3 Hz, 3H); LCMS [M+H]$^+$ 1186.

Heterocyclic Linker-DM1 Construct (IV)

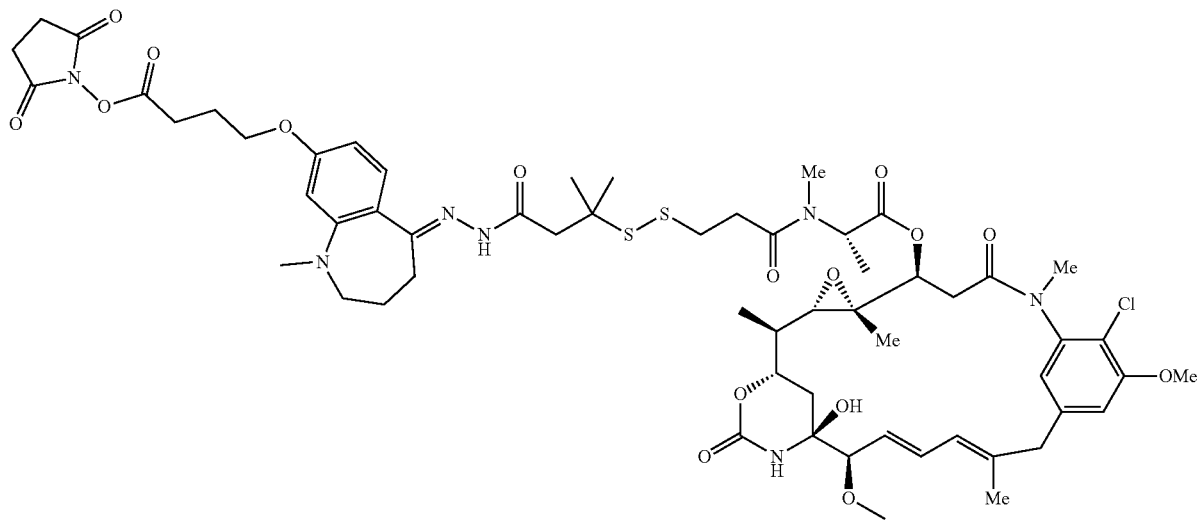

IVf

Heterocyclic linker-DM1 construct IVf was prepared according to a similar procedure to heterocyclic linker-DM1 IVa. It was collected as an off-white fluffy powder (13.5 mg, 58.3% yield, 2 isomers). $^1$H NMR (DMSO-d6, 500 MHz) β 10.39 (s, 1H), 10.13 (s, 1H), 7.3-7.4 (m, 1H), 7.1-7.2 (m, 1H), 6.88 (br d, 1H, J=5.0 Hz), 6.6-6.7 (m, 1H), 6.5-6.6 (m, 2H), 6.4-6.5 (m, 1H), 6.37 (s, 1H), 5.92 (d, 1H, J=5.4 Hz), 5.53 (td, 1H, J=9.0, 14.9 Hz), 5.31 (quin, 1H, J=7.0 Hz), 4.51 (ddd, 1H, J=2.6, 6.1, 11.9 Hz), 4.0-4.1 (m, 3H), 3.91 (d, 3H, J=6.6 Hz), 3.5-3.5 (m, 2H), 3.25 (d, 3H, J=5.0 Hz), 3.15 (s, 1H), 3.13 (s, 1H), 3.0-3.0 (m, 2H), 2.86 (br d, 5H, J=4.5 Hz), 2.82 (br s, 4H), 2.7-2.7 (m, 2H), 2.67 (s, 2H), 2.0-2.1 (m, 3H), 1.87 (td, 2H, J=5.8, 11.5 Hz), 1.58 (br d, 3H, J=11.7 Hz), 1.4-1.5 (m, 4H), 1.2-1.3 (m, 9H), 1.17 (br dd, 4H, J=7.1, 8.2 Hz), 1.1-1.1 (m, 3H), 0.78 (d, 3H, J=3.8 Hz), LCMS [M+H]$^+$ 1241.

Synthesis of Linker-MonoMethyl Auristatin E (MMAE) Constructs

The representative linkers are conjugated to MMAE via a disulfide bond formation reaction according to the synthetic procedures described in schemes (11) and (12). MMAE intermediate 4-5 was prepared in 3 steps from commercially available (tert-butoxycarbonyl)-L-valyl-L-alanine. It was reacted with 2,2'-dithiobis(5-nitropyridine) to form the MMAE-thio(5-nitropyridine) intermediate 4-6. This intermediate was then reacted with thiol of linkers (for example: Ia-1) to form the disulfide bond between the linker and MMAE intermediate which gave the final linker MMAE constructs (IVg, IVh, IVi) that are ready for antibody conjugation.

Scheme (11)
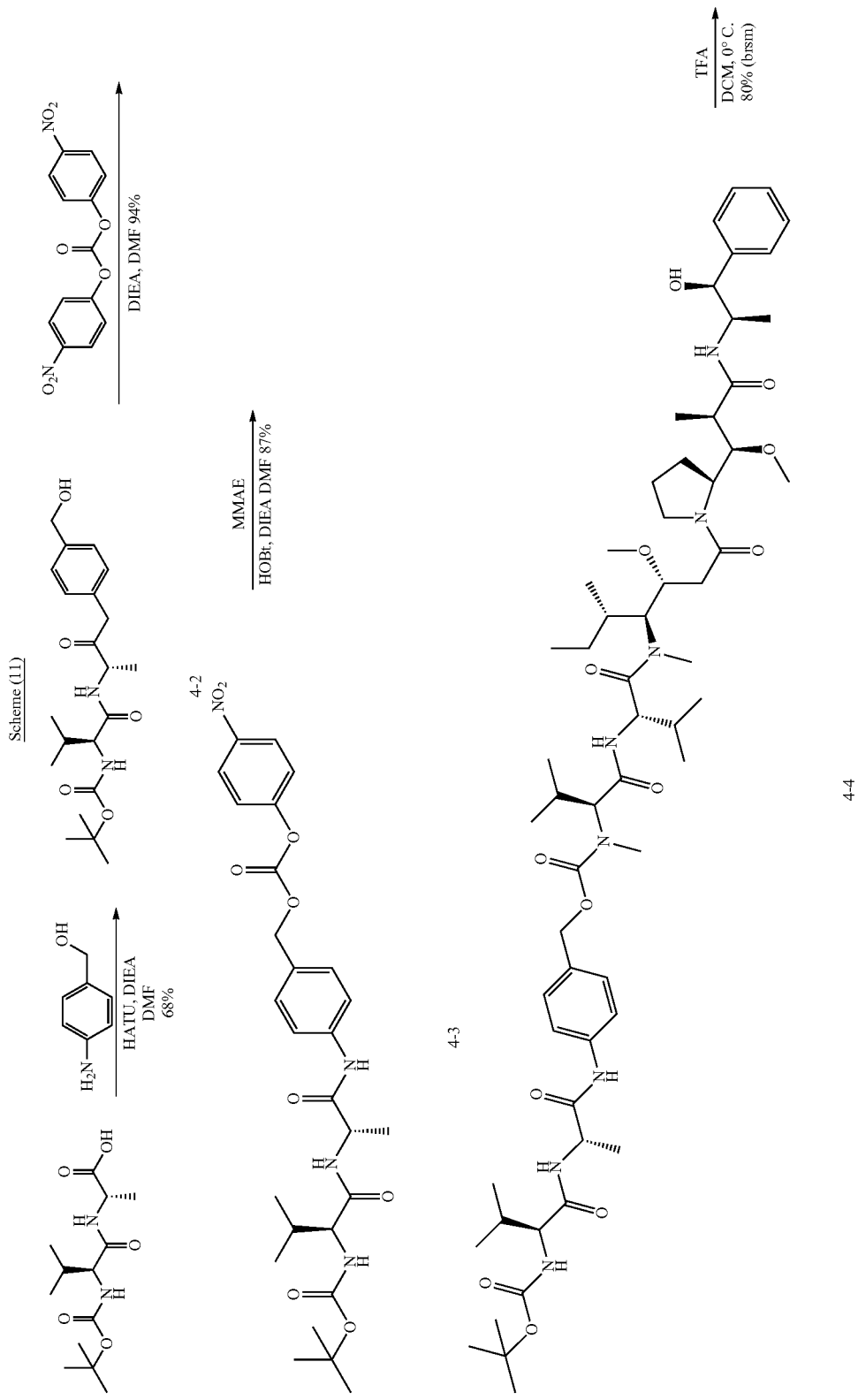

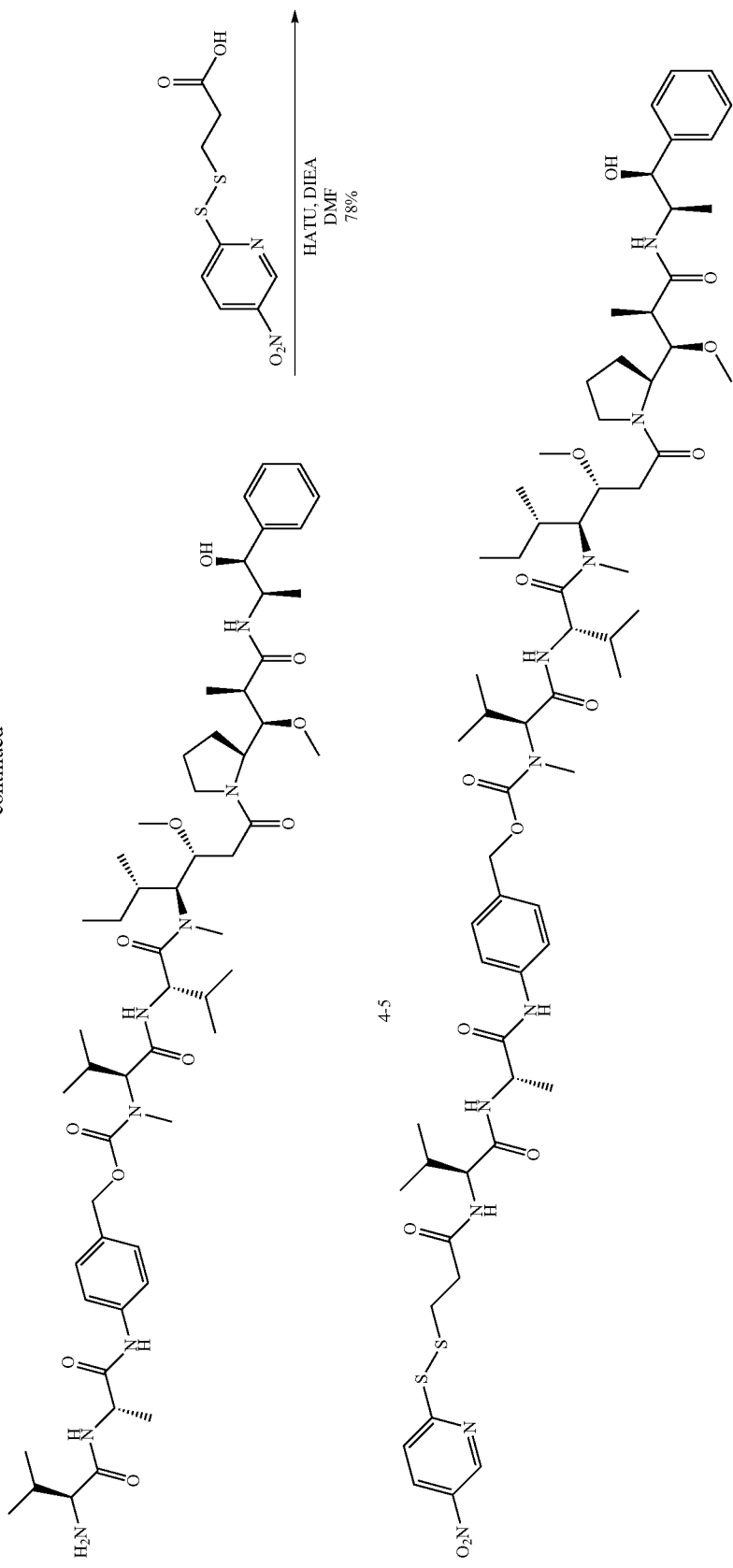

tert-Butyl((S)-1-(((S)-1-((4-(hydroxymethyl)phenyl)amino)-1-oxopropan-2-yl)amino)-3-methyl-1-oxobutan-2-yl)carbamate (4-2)

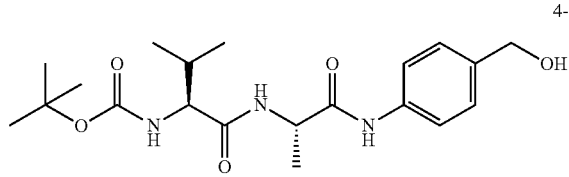

A solution (tert-butoxycarbonyl)-L-valyl-L-alanine (285 mg, 0.988 mmol) and 4-aminobenzyl alcohol (183 mg, 1.483 mmol) in THF (5 ml) was treated with EEDQ (367 mg, 1.483 mmol). The solution was stirred at room temperature. After 1 h no product was observed. DMF (5 ml) and HATU (564 mg, 1.483 mmol) were added. After 5 min, N,N-diisopropylethylamine (0.689 ml, 3.95 mmol) was added after which LCMS showed completion. The mixture was stirred for an additional 1 h. The volatile solvents were removed under reduced pressure. The crude was diluted with EtOAc. The organic layer was washed with water (×3). A small amount of brine was added to break any suspension that has formed. It was then washed with brine and dried over Na$_2$SO$_4$. The organic layer was concentrated down, loaded on celite and dried. It was purified over Isco (12 g silica column, eluent EtOAc/Hexanes: 0-70% then 70%) to afford the title compound 4-2 as an off-white solid (265 mg, 68% yield). $^1$H NMR (DMSO-d6, 500 MHz) δ 9.93 (br s, 1H), 8.05 (br d, 1H, J=6.7 Hz), 7.53 (br d, 2H, J=8.2 Hz), 7.24 (br d, 2H, J=8.1 Hz), 6.74 (br d, 1H, J=8.7 Hz), 5.10 (t, 1H, J=5.6 Hz), 4.43 (br d, 2H, J=5.3 Hz), 3.84 (br t, 1H, J=7.5 Hz); 1.9-2.0 (m, 1H), 1.39 (s, 9H), 1.30 (br d, 3H, J=6.8 Hz), 0.87 (br d, 3H, J=6.5 Hz), 0.82 (br d, 3H, J=6.4 Hz); LCMS [M+H]$^+$ 394.

tert-Butyl((S)-3-methyl-1-(((S)-1-((4-(((((4 nitrophenoxy)carbonyl)oxy)methyl)phenyl)amino)-1-oxopropan-2-yl)amino)-1-oxobutan-2-yl)carbamate (4-3)

To a 100 ml RB flask containing tert-butyl ((S)-1-(((S)-1-((4-(hydroxymethyl)phenyl)amino)-1-oxopropan-2-yl)amino)-3-methyl-1-oxobutan-2-yl)carbamate 4-2 (263 mg, 0.668 mmol) was added bis(4-nitrophenyl) carbonate (244 mg, 0.802 mmol) then DMF (3 ml). N,N-Diisopropylethylamine (0.466 ml, 2.67 mmol) was added to this stirring mixture. After 2 h at rt, LCMS showed almost completion. The solvent was evaporated under high vacuum. The crude was purified over Isco (12 g silica column, eluent: EtOAc/Hexanes; 0%, 0-50% then 50%) to give the title compound 4-3 as an off-white waxy solid (352 mg, 94% yield). $^1$H NMR (DMSO-d6, 500 MHz) δ 10.10 (br s, 1H), 8.32 (br d, 2H, J=8.9 Hz), 8.10 (br d, 1H, J=6.7 Hz), 7.64 (br d, 2H, J=8.2 Hz), 7.58 (br d, 2H, J=8.9 Hz), 7.42 (br d, 2H, J=8.3 Hz), 6.73 (br d, 1H, J=8.7 Hz), 5.25 (s, 2H), 4.44 (br t, 1H, J=6.7 Hz), 3.85 (br t, 1H, J=7.5 Hz), 2.90 (s, 1H), 2.74 (s, 1H), 1.9-2.0 (m, 1H), 1.39 (s, 9H), 1.32 (br d, 3H, J=7.0 Hz), 0.88 (br d, 3H, J=6.7 Hz), 0.83 (br d, 3H, J=6.5 Hz), LCMS [M+H]$^+$ 559.

MMAE Intermediate (4-4)

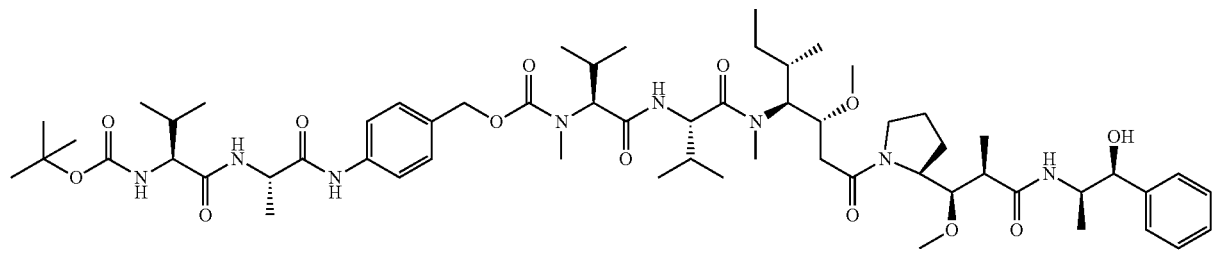

To a 100 ml RB flask containing tert-butyl((S)-3-methyl-1-(((S)-1-((4-(((((4nitrophenoxy)carbonyl)oxy)methyl)phenyl)amino)-1-oxopropan-2-yl)amino)-1-oxobutan-2-yl)carbamate 4-3 (349 mg, 0.625 mmol), was added monomethyl auristatin E (MMAE) (359 mg, 0.500 mmol) and 1-hydroxybenzotriazole (HOBt) (41.5 mg, 0.307 mmol). DMF (10 ml) was added then the mixture was stirred at rt. N,N-Diisopropylethylamine (0.216 ml, 1.240 mmol) was slowly added via a syringe. After about 24 h at rt, LCMS showed almost completion. The solvent was evaporated under high vacuum. The crude was purified by Isco (12 g column, eluent: EtOAc/Hexanes: 0-100% then 100%) to give the title compound 4-4 as a white foamy solid (493 mg, 87% yield). LCMS [M+H]$^+$ 1138.

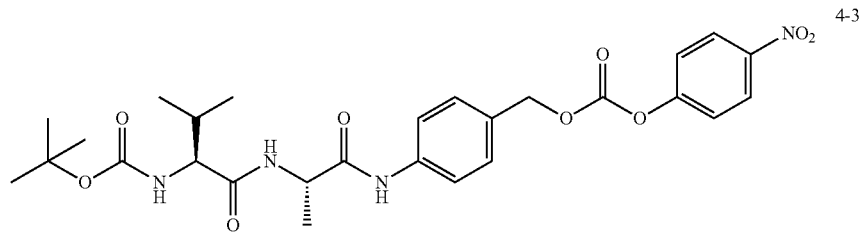 [SMILES: CC(C)[C@H](NC(=O)OC(C)(C)C)C(=O)N[C@@H](C)C(=O)Nc1ccc(COC(=O)Oc2ccc([N+](=O)[O-])cc2)cc1]

MMAE Intermediate (4-5)

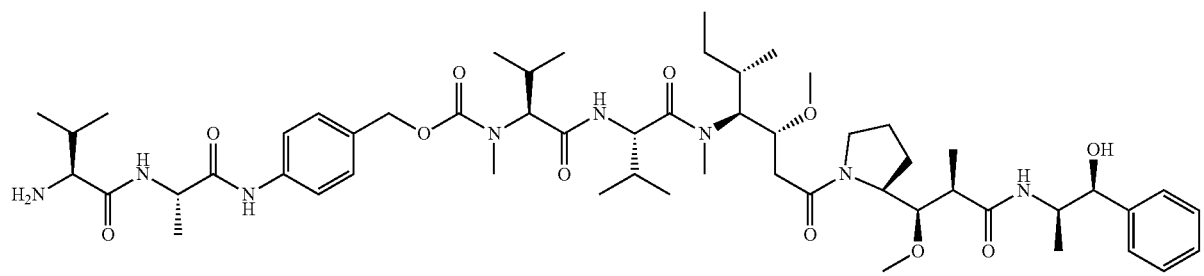

4-5

To a 100 ml RB flask containing MMAE intermediate 4-4 (477 mg, 0.419 mmol) was added dichloromethane (20 ml). The mixture was cooled to 0° C. with an ice bath upon which trifluoroacetic acid (4 ml) was added dropwise via a syringe. After 15 min, 2 ml of TFA were added. The mixture was stirred for another 15 min then the solvents were evaporated off. The crude was dissolved in MeOH, loaded on celite and dried. It was purified over Isco (13 g C18 column, eluent: $CH_3CN/H_2O$: 10-100% then 100%). The title compound 4-5 was collected as an off-white solid (307 mg, 80% yield brsm). LCMS $[M+H]^+$ 1038.

MMAE Intermediate (4-6)

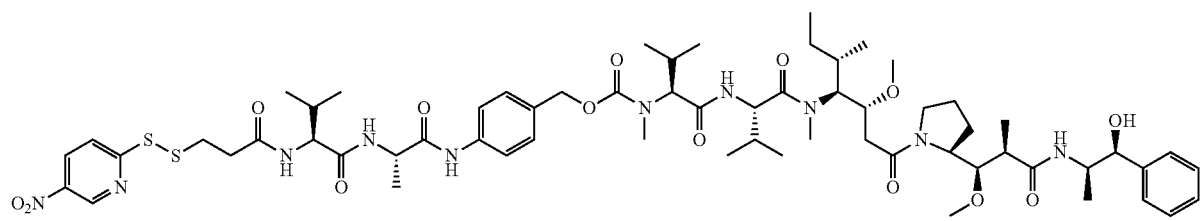

4-6

To a 100 ml RB flask containing MMAE intermediate 4-5 (305 mg, 0.265 mmol), HATU (151 mg, 0.397 mmol) and 3-((5-nitropyridin-2-yl)disulfanyl)propanoic acid (68.9 mg, 0.265 mmol), was added DMF (6 ml). The mixture was stirred for 5 min at rt upon which N,N-diisopropylethylamine (0.231 ml, 1.325 mmol) was added via a syringe. After 30 min at rt, LCMS showed completion. Some celite was added then it was dried for a short time under reduced pressure. The crude was purified over Isco (13 g C18 cartridge, eluent: $CH_3CN$/water: 10-30%, 30-100% then 100%) to afford the title compound 4-6 as a light orange solid (265 mg, 78% yield). LCMS $[M+H]^+$ 1280.

Final Linker-MMAE Constructs

Scheme (12)
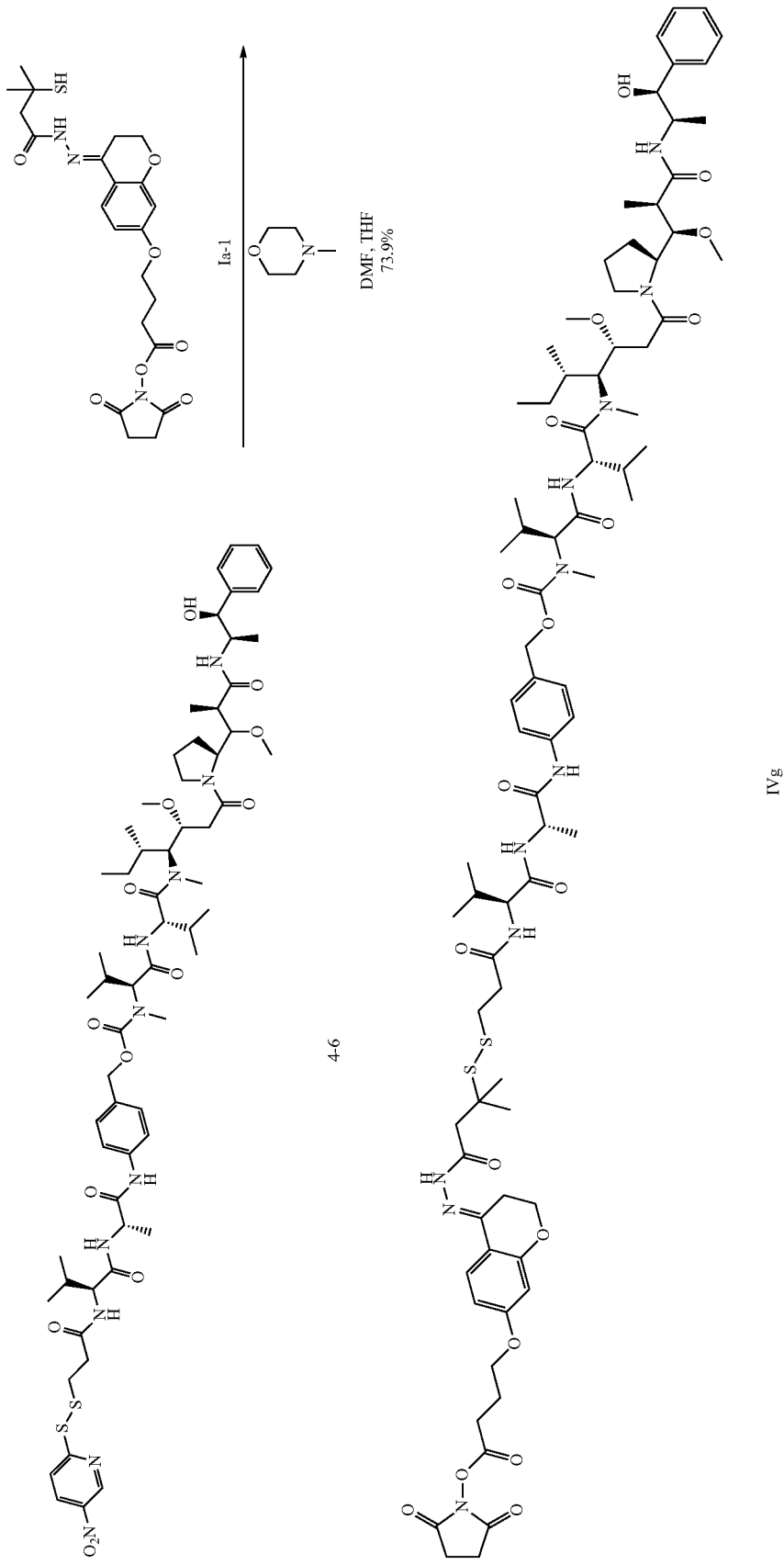

Linker-MMAE Construct (IVg)

IVg

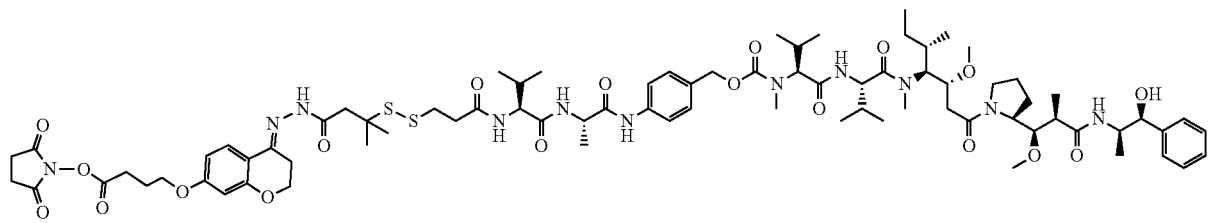

MMAE intermediate 4-6 (15 mg, 0.012 mmol) was dissolved in DMF (1 ml) then 2,5-dioxopyrrolidin-1-yl-4-((4-(2-(3-mercapto-3-methylbutanoyl)hydrazono) chroman-7-yl)oxy)butanoate Ia-1 (25 mg, 0.05 mmol, crude) in THF (1.5 ml) was added. 4-Methylmorpholine (0.028 ml, 0.014 mmol) as a (0.5 M) solution in DMF was added. The mixture was stirred at room temperature for 20 min upon which LCMS showed completion. The crude mixture was separated between water and EtOAc and shaken. The organic layer was washed with water (×3) then brine. It was dried over $Na_2SO_4$ and concentrated down. The crude was purified over Isco (4 g silica column; eluent: EtOAc/Hexanes; 0-100% then 100% EtOAc followed by acetone/EtOAc 0-60% then 60%). The title compound IVg was taken into acetonitrile frozen then lyophilized. It was collected as a white fluffy powder (14.6 mg, 73.9% yield). $[M+H]^+$ 1601.

Linker-MMAE Construct (IVh)

IVh

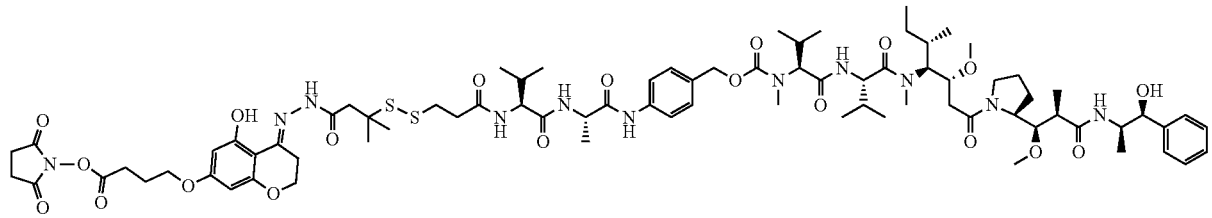

Linker-MMAE construct IVh was prepared according to a similar procedure to linker-MMAE construct IVg. It was collected as a white fluffy powder (4.6 mg, 21.9% yield). LCMS $[M+H]^+$ 1617. A lesser pure fraction of the product was also collected during the purification step (13.6 mg).

Linker-MMAE Construct (IVI)

IVi

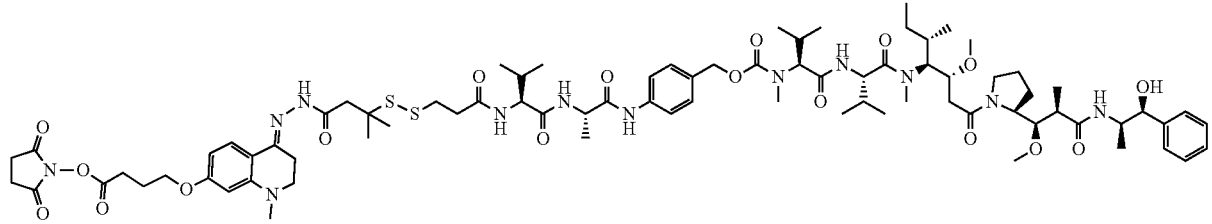

Linker-MMAE construct IVi was prepared according to a similar procedure to linker-MMAE construct IVg. It was collected as a white fluffy powder (11 mg, 55.2% yield). LCMS $[M+H]^+$ 1614.

Another representative linker is conjugated to MMAE via a disulfide bond formation reaction according to the synthetic procedures described in scheme (13). MMAE intermediate 4-8 was prepared in 2 steps from commercially available (9H-fluoren-9-yl)methyl ((S)-3-methyl-1-(((S)-1-((4-(((((4-nitrophenoxy)carbonyl)oxy)methyl)phenyl) amino)-1-oxo-5-ureidopentan-2-yl)amino)-1-oxobutan-2-yl)carbamate (Fmoc-Val-Cit-PAB-pnp). It was reacted with 2,2'-dithiobis(5-nitropyridine) to form the MMAE-thio(5-nitropyridine) intermediate 4-9. This intermediate was then reacted with thiol of linker Ib-1 to form the disulfide bond between the linker and MMAE intermediate which gave the final linker MMAE construct (IVj) that is ready for antibody conjugation.

Scheme (13)
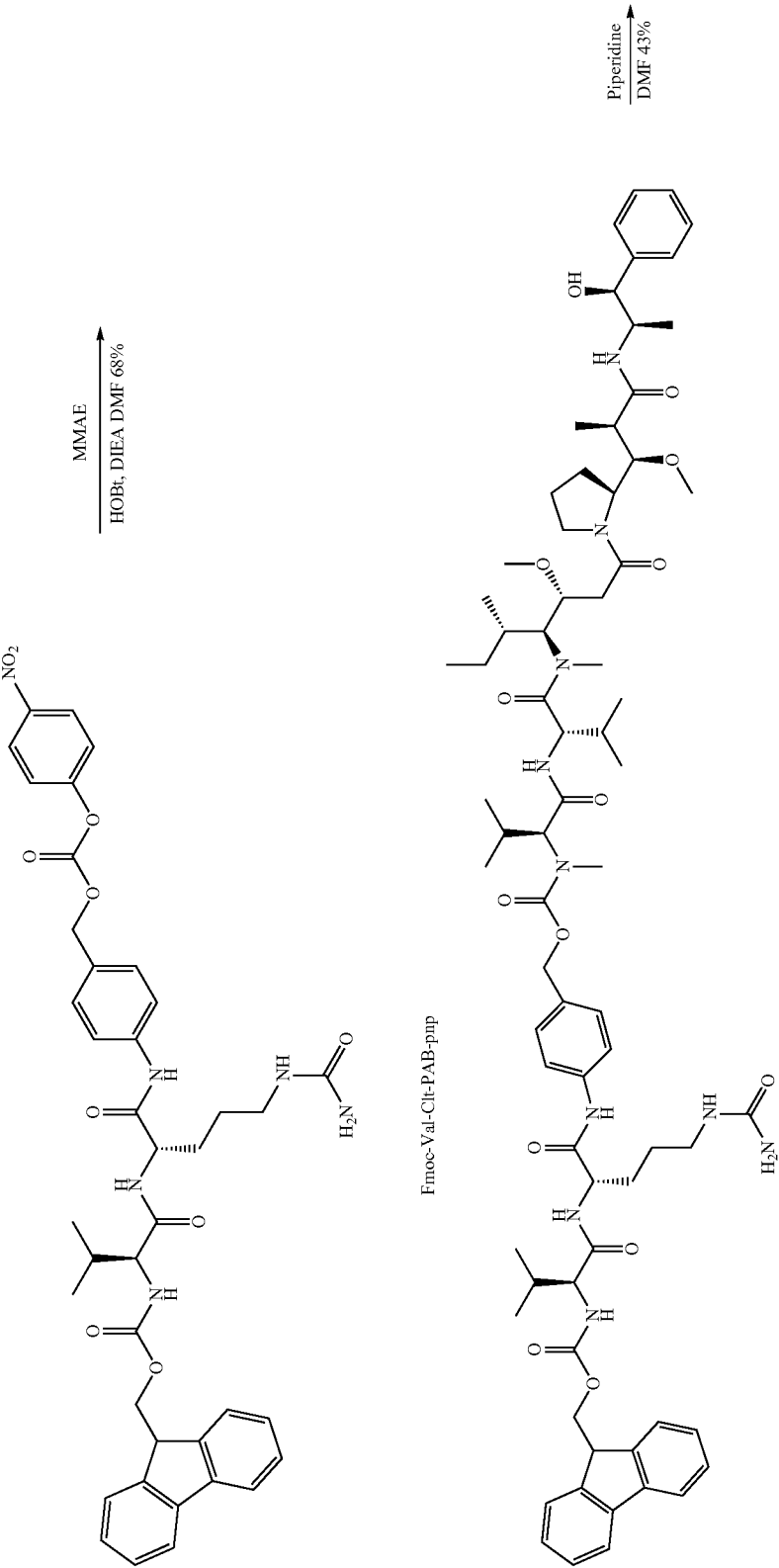

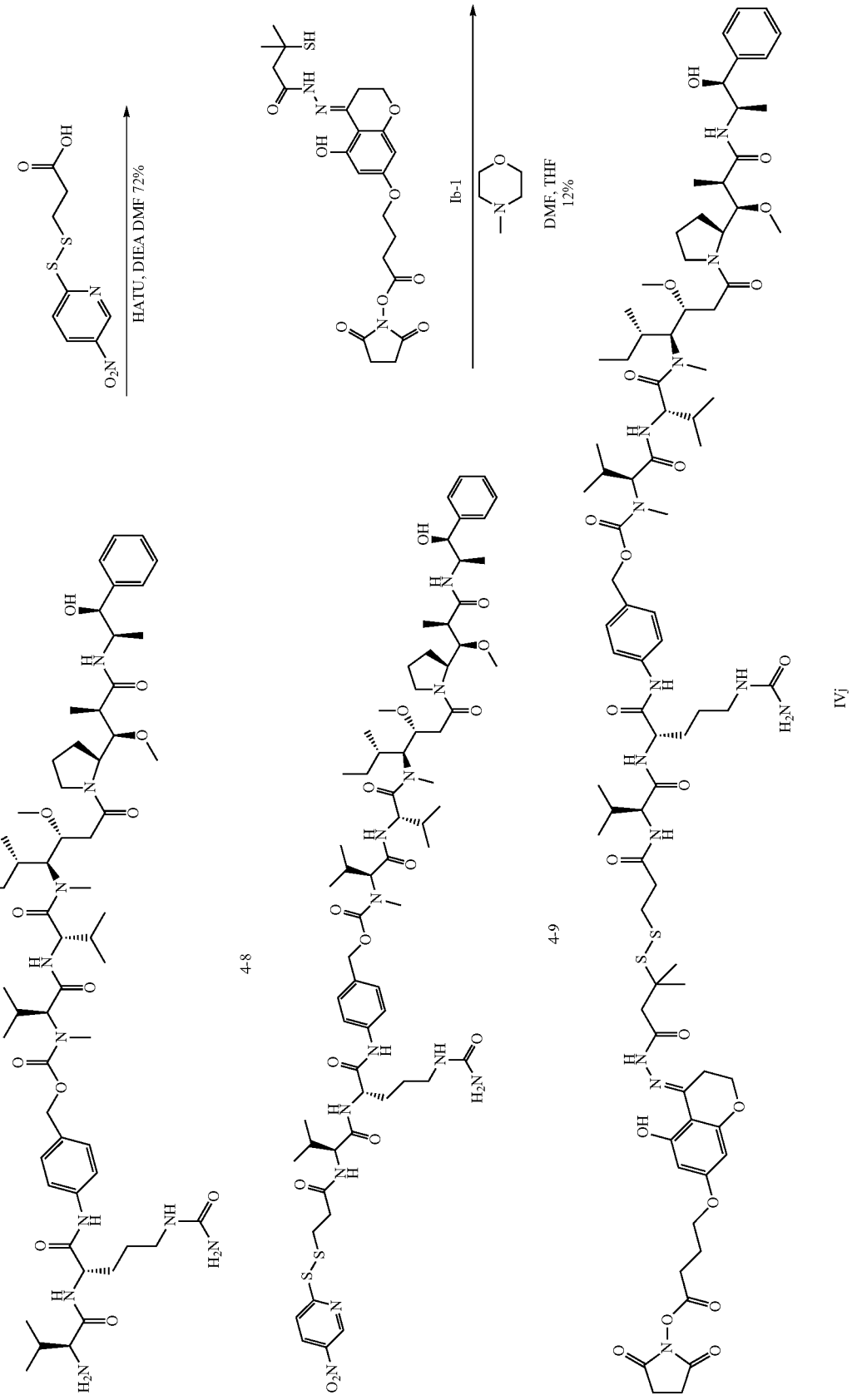

MMAE Intermediate (4-7)

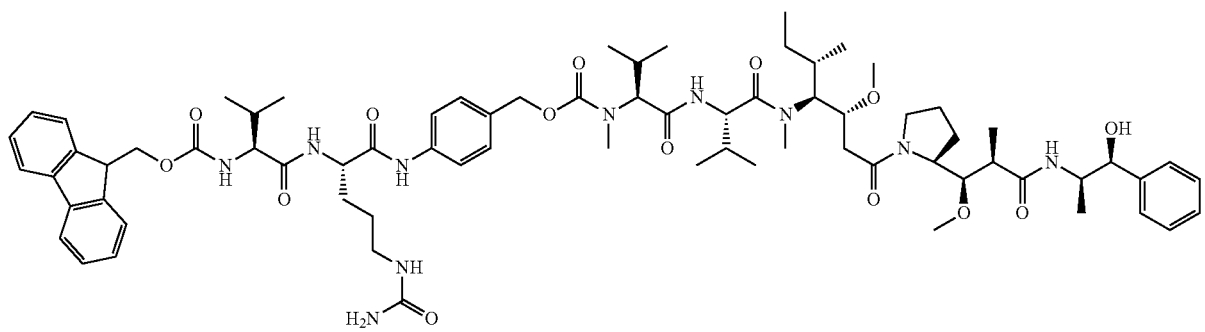

4-7

A 100 ml RB flask was charged with monomethyl auristatin E (MMAE) (200 mg, 0.279 mmol), 1-hydroxybenzotriazole (23.34 mg, 0.173 mmol) and Fmoc-Val-Cit-PAB-pnp (269 mg, 0.351 mmol). N,N-Dimethylformamide (8 ml) was added then the mixture was stirred at rt upon which N,N-diisopropylethylamine (0.121 ml, 0.696 mmol) was slowly added via a syringe. After 1 day at rt, LCMS showed almost completion. The solvent was evaporated under high vacuum. The crude was dissolved in DMF, loaded on celite and dried. It was purified by Isco (12 g column, eluent: EtOAc/Hexanes: 0-100% then 100% then DCM/MeOH: 0-20% then 20%) to give the title compound 4-7 as an off-white solid (256 mg, 68% yield). LCMS $[M+H]^+$ 1346.

MMAE Intermediate (4-8)

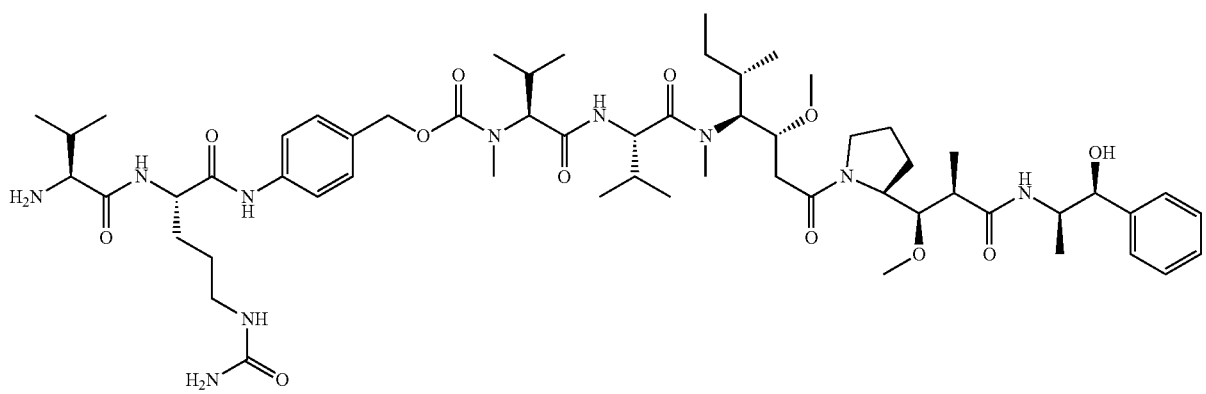

4-8

MMAE intermediate 4-7 (256 mg, 0.190 mmol) was dissolved in N,N-dimethylformamide (4 ml) then piperidine (1.997 mmol, 20% in DMF 1 ml) was added. The mixture was stirred at rt for 30 min upon which LCMS showed completion. Celite was added then it was dried. It was purified by Isco reverse phase (13 g C18 column: eluent $CH_3CN$/water: 10-100% then 100%) to give the title compound 4-8 as an off-white solid (92 mg, 43% yield). LCMS $[M+H]^+$ 1124.

MMAE Intermediate (4-9)

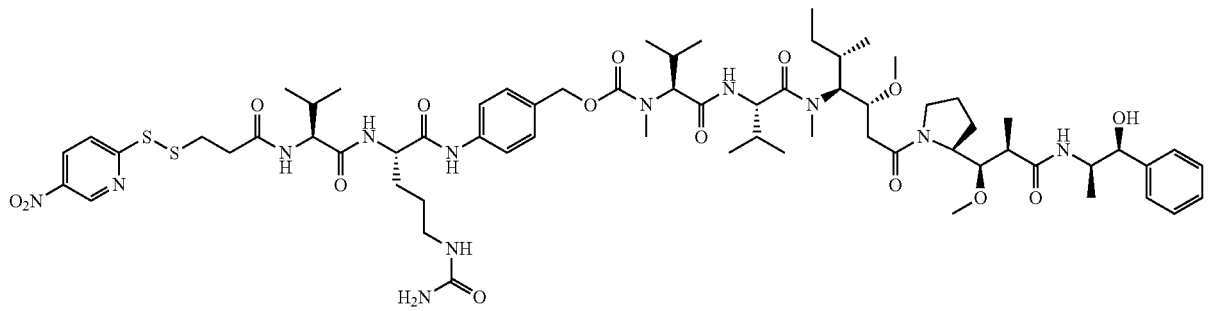

4-9

To a 100 ml RB flask containing MMAE intermediate 4-8 (91 mg, 0.081 mmol), HATU (46.2 mg, 0.122 mmol) and 3-((5-nitropyridin-2-yl)disulfanyl)propanoic acid (21.08 mg, 0.081 mmol) were added then this mixture was dissolved in N,N-dimethylformamide (3 ml). It was stirred for 5 min upon which N,N-diisopropylethylamine (0.056 ml, 0.324 mmol) was added. After stirring at room temperature for 30 min, LCMS showed completion. Some celite was added then it was dried for a short time under reduced pressure. It was purified over Isco (reverse phase: 13 g C18 cartridge; eluent CH$_3$CN/water: 10-100% then 100%). The right product was lyophilized from acetonitrile to afford the title compound 4-9 as a very light orange fluffy powder with a partial orange glassy solid (79.6 mg, 72.0% yield). LCMS [M+H]$^+$ 1366.

Linker-MMAE Construct (IVj)

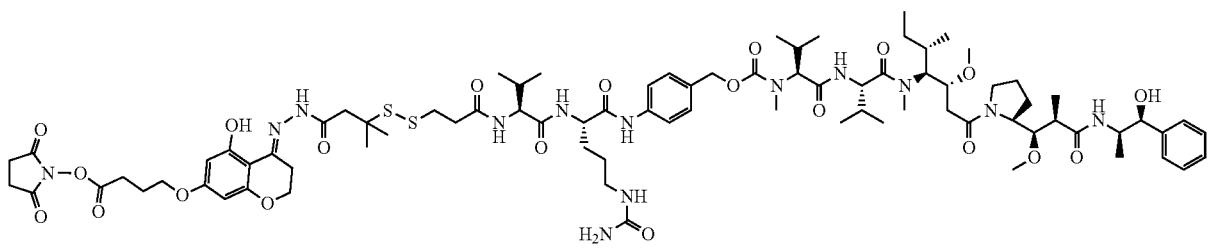

IVj

MMAE intermediate 4-9 (15.45 mg, 0.011 mmol) was dissolved in DMF (1 ml) then 2,5-dioxopyrrolidin-1-yl-4-((5-hydroxy-4-(2-(3-mercapto-3-methylbutanoyl) hydrazono)chroman-7-yl)oxy)butanoate Ib-1 (26.1 mg, 0.053 mmol) in 3 ml of THF was added (Ib-1 was prepared using a similar procedure to Ia-1 and was used as a crude intermediate in this reaction). The mixture was stirred at rt upon which 4-methylmorpholine (0.027 ml, 0.014 mmol) as a (0.5 M) solution in DMF was added. The mixture was stirred at room temperature for 15 min upon which LCMS showed completion. The crude mixture was separated between water and EtOAc and shaken. The organic layer was washed with water (×3) then brine. The crude was purified over Isco (4 g silica column; eluent: EtOAc/Hexanes; 0-100% then 100% EtOAc followed by acetone/EtOAc 0-60%, 60%, 60-100% then 100%). It was then purified by reverse phase chromatography using Isco (4.3 g C18 column: 10-100% then 100% CH$_3$CN/water). It was further purified by Isco normal phase (4 g gold silica column; eluent: acetone/EtOAc 0-60%, 60%, 60-100% then 100%). The title compound IVj was taken into acetonitrile frozen then lyophilized. It was collected as a white fluffy powder (2.47 mg, 12% yield). LCMS [M+H]$^+$ 1703.

Conjugation of DM1-Linker Constructs of Formula IV to Trastuzumab

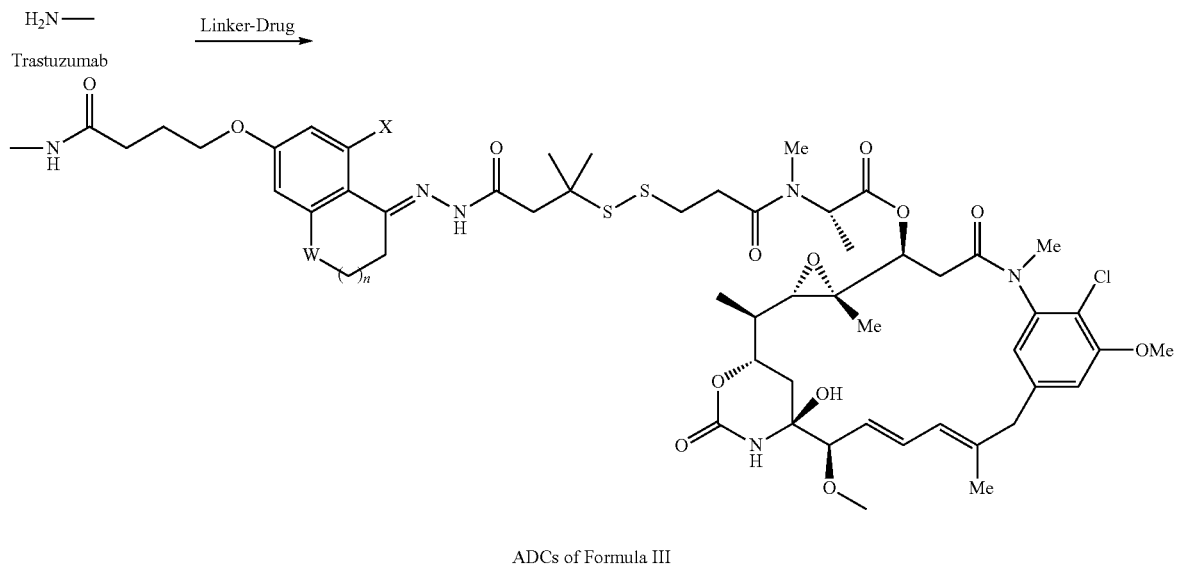

ADCs of Formula III

The goal of this procedure is chemically link the cytotoxin microtubule inhibitor DM1 to surface accessible lysine residues on the human IgG1 antibody Trastuzumab by reaction of DM1-linker constructs (IV) with the antibody.

Concentrated (10 mM) stock solutions of the linker with the attached DM1 payload of formula IV are prepared in dimethylacetamide (DMA) and stored at −20° C. just prior to use. Prior to conjugation the concentrated stock is brought up to the temperature of 25° C. and then used to prepare a working stock in DMA equivalent to 5 times the desired concentration to be used in the reaction. The reaction mixture consists of 13.3 M of Trastuzumab, 66.5 M Linker-DM1, 100 mM sodium phosphate, 20 mM NaCl, pH 7.4. Once mixed, the reaction is incubated at 32° C. for 2.5 hours.

The reaction is stopped by buffer exchanging the sample into 20 mM sodium phosphate, 0.02% w/v Polysorbate 20 pH 7.4. Trehalose is then added to 6% w/v prior to storage at −80° C. Buffer exchange can be accomplished via gravity/spin desalting columns or tangential flow filtration methods.
Analysis of Bioconjugates The absorbance of formulated bioconjugates is measured at 280 nm and one additional wavelength specific for the particular linker used. The extinction coefficient of this second wavelength is determined empirically for each combination of linker and payload used. The corresponding absorbance of the parental antibody is also measured at these two same wavelengths. The drug/antibody ratio is determined using the following equation. The second wavelength shown here is 252 nm, but this will depend on the particular linker-drug combination used;

$$DAR = \frac{\left(\frac{A_{252}}{A_{280} * \varepsilon_{Ab}^{280}}\right) - \varepsilon_{Ab}^{252}}{\varepsilon_{ADC}^{280} - \left(\frac{A_{252}}{A_{280} * \varepsilon_{ADC}^{280}}\right)}$$

ADC—refers to the free linker-drug prior to conjugation
Ab—refers to the antibody prior to conjugation.

For conjugation with Trastuzumab a ratio of 10/1 (linker-drug/antibody) was used. Representative results are shown in Table 3 below;

TABLE 3

Representative results of Trastuzumab ADCs of Formula III synthesis from linker-drug compounds of Formula IV

| ADCs Formula III | Linker-Drug Formula IV | # eq of IV | DAR ratio small scale | DAR ratio large scale | # eq of IV | DAR ratio |
|---|---|---|---|---|---|---|
| IIIa | IVa | 5 | 2.95 | 3.20 | 10 | 5.3 |
| IIIb | IVb | 5 | NA | NA | 10 | 3.3 |
| IIIc | IVc | 5 | 1.08 | 2.67 | 10 | 5.7 |
| IIIe | IVe | 5 | 1.32 | 1.8 | 10 | 1.4 |

In general, the conjugation reactions worked well with several drug linkers giving ADCs with yields >70%. The DAR ratio was dependent of amount of linker-drug (Formula IV) versus Trastuzumab. For example for 5 eq of IVa, the DAR ratios were 2.95 and 3.20 for the small and large conjugation reactions respectively whereas when 10 eq of IVa was used in this particular conjugation reaction, an ADC with a DAR ratio of 5.3 was obtained. Of note, for these conjugation conditions, the Mylotarg type linker-drug IVe gave an ADC with modest DAR ratios (ADC IIIe, DAR between 1.32 and 1.8).
Biological Testing of Antibody-Drug Conjugates The Cytotoxic Activity of Trastuzumab ADCs of Formula III was Tested Against SKOV3 Ovarian Cell Lines SKOV3 ovarian cells are incubated with the effectors for a period corresponding to 2 to 3 times their estimated doubling time and the amount of viable cells is determine by measuring ATP content in the wells. ATP has been widely accepted as a valid marker of viable cells. When cells lose membrane integrity, they lose the ability to synthesize ATP and endogenous ATPases rapidly deplete any remaining ATP from the cytoplasm. All ADCs are diluted in DPBS to 6× the highest concentration tested, followed by 10 3-fold serial dilutions in DPBS for a total of 11 concentration points. Each point is added to triplicate wells. DPBS is added in wells to measure the maximum growth. Cells are diluted at their appropriate seeding density (ranging from 150 to 1000 cells per well) in complete media supplemented with glutamine 2 mM, serum and antibiotic cocktail. They are distributed in white, opaque bottom, tissue-culture treated 384 well plates and incubated for 24 hrs at 37° C.+5% $CO_2$. After addition of ADCs, cells are incubated at 37° C.+5% $CO_2$ for the appropriate amount of time (3 to 5 days) prior to cell viability count. Total ATP is measured using CellTiter-Glo reagent from Promega as recommended by the supplier. The cells and the reagent are equilibrated at room temp. for 30 min before mixing. Cell lysates are then incubated for 30 min to 1 hr at room temp. protected from light. Signal output is measured on a luminescence plate reader (envision, Perkin Elmer) set at an integration time of 0.1 sec. Integration time is adjusted to minimise signal saturation at high ATP concentration.

Data Analysis

Each concentration point (S) is normalized to the negative control wells (NC) and expressed as % survival (NC-S/NC× 100). Potency ($IC_{50}$) and efficacy are calculated from a non-linear curve fit of the points versus log of the concentrations without constrain on the slope. Refined data are analysed using Prism software.

In this study a positive control ADC (Trastuzumab-SMCC-DM1) and a negative control ADC (Synagis-SMCC-DM1) were used. The cytotoxicity data against SKOV3 ovarian cancer lines is shown in Table 4 below.

TABLE 4

Cytotoxicity against SKOV3 Ovarian Cancer Cells

| ADC | $IC_{50}$ (nM) | DAR ratio |
|---|---|---|
| Synagis-SMCC-DM1 | 9.64 | 3.39 |
| Trastuzumab-SMCC-DM1 | 0.038 | 3.50 |
| IIIa | 0.054 | 6.59 |
| IIIc | 0.191 | 6.99 |
| IIIa | 0.599 | 3.20 |
| IIIc | 1.008 | 2.67 |

ADC IIIa showed very potent activity against SKOV3 ovarian cell lines ($IC_{50}$: 0.054 nM). ADC IIIc also showed very good potency with an $IC_{50}$ of 0.191 nM. ADCs IIIa and IIIc also showed potent cell growth inhibition even at a lower DAR with $IC_{50}$'s of 0.599 and 1.008 nM respectively. Both ADCs were significantly more active in this assay than the negative control Synagis-SMCC-DM1.

Serum Stability Study

To assess the stability of Trastuzmab ADCs in serum, representative examples (IIIa, IIIc and IIIe) were studied to measure the ratio of hydrazone cleavage product upon serum incubation. The goal was to compare the stability of ADCs IIIa and IIIc to the ADC containing Mylotarg linker IIIe. The hydrazone cleavage product is shown in Scheme (14).

Scheme 14

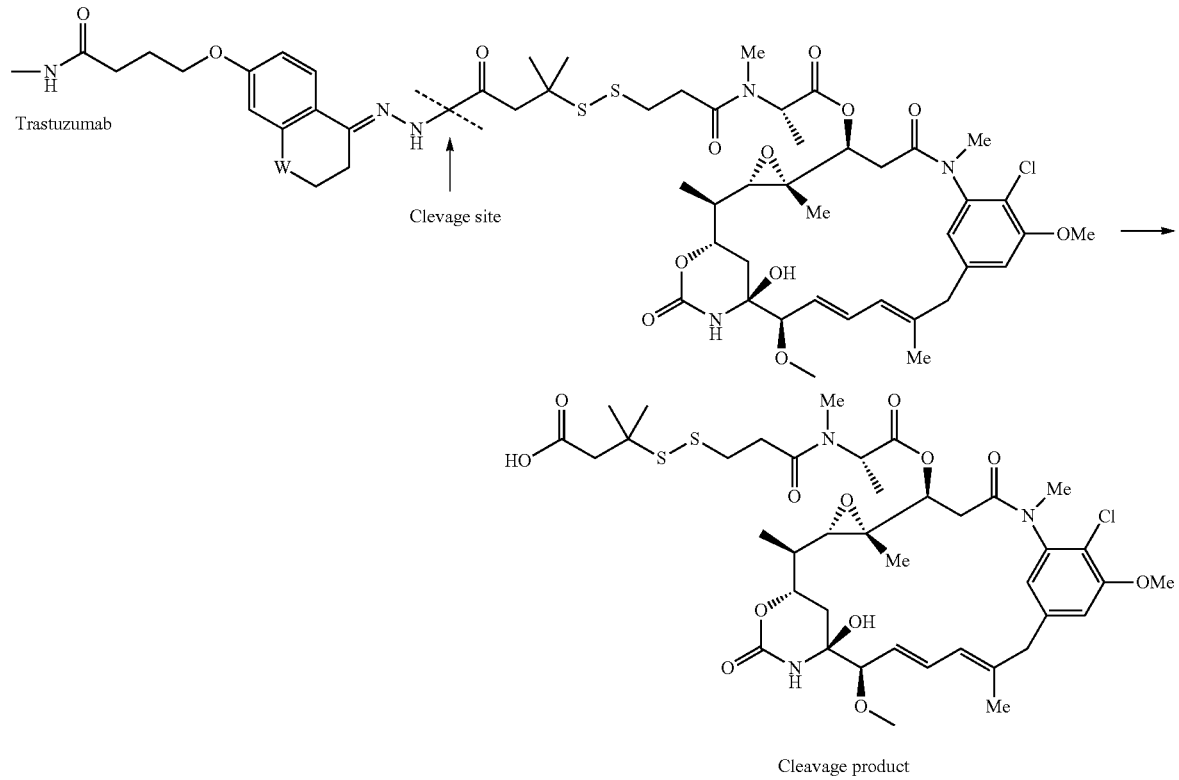

Cleavage product

Serum Incubation and LCMS Analysis

The selected ADCs (200 µL each of serum sample) were prepared in mouse serum as follows: 158.4 µL mouse serum and the following final concentration of the following reagents:

5 mM EDTA
10 mM Na Azide
500 µM of ADC

The ADCs used in this study had the following DAR ratios: IIIa: DAR 2.95, IIIc: DAR 1.08 & IIIe: DAR 1.32

The mixture was incubated in a 1.5 mL PP centrifuge tube with O-ring at 37° C. for 3 days. Aliquots of 45 µL were removed at 0, 24, 48 and 72 hours into cryovials and immediately frozen at −80° C.

The cleavage product was analyzed by LCMS. The method used for processing serum samples and subsequent analysis by LCMS were taken from Durbin et. al. "*High-Throughput, Multispecies, Parallelized Plasma Stability Assay for the Determination and Characterization of Antibody-Drug Conjugate Aggregation and Drug Release*". *ACS Omega*. 2017, 2(8), pp 4207-4215.

Figure 2:
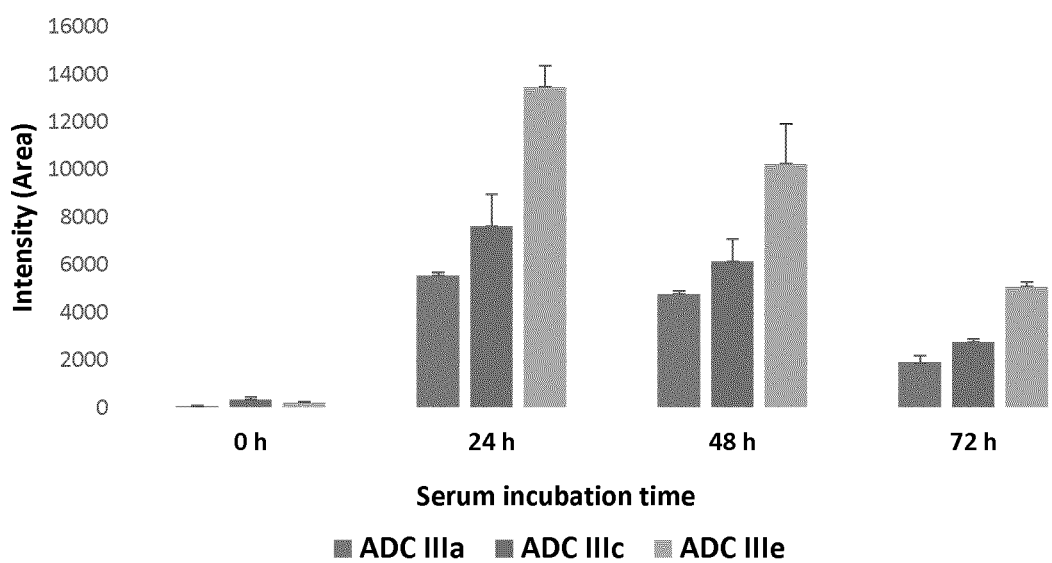
FIG. 2 is bar graph showing the stability of exemplary ADCs of Formula (IIIa) and (IIIc) (left and middle bars) and comparative ADC of Formula (IIIe) (right bar) in mouse serum.

ADCs IIIa and IIIc were more stable than the benchmark containing the Mylotarg linker IIIe at the different time points. There was very little free catabolite from the hydrazone cleavage site at time zero and levels increased to a maximum in this assay after 24 hours. After this point the values declined gradually for all ADCs investigated as seen in FIG. 2.

Hence, representative linkers of the current application have an improved plasma stability over the Mylotarg linker which should mitigate the toxicities associated with the premature release of payloads in the systemic circulation. Conjugates prepared using the linkers of the present application should therefore result in a better therapeutic window and thus benefit a larger patient population.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE APPLICATION (1) a. In American Cancer Society. "Chemotherapy side effects" 2017. Available at https://www.cancer.org/treatment/treatments-and-side-effects/treatment-types/chemotherapy/chemotherapy-side-effects.html (Accessed Sep. 14, 2017);
b. Beck, A.; Goetsch L.; Dumontet, C. and Corvaia, N. Strategies and challenges of next generation antibody-drug conjugates, *Nat. Rev. Drug. Discov.* 2017, 16, 315-337.
(2) Chabner, B. A.; Roberts, T. G., Jr. Timeline: Chemotherapy and the war on cancer, *Nat. Rev. Cancer* 2005, 5, 65-72.
(3) Allen, T. M. Ligand-targeted therapeutics in anticancer therapy, *Nat. Rev. Cancer* 2002, 2, 750-763.
(4) Helleday, T.; Petermann, E.; Lundin, C.; Hodgson, B.; Sharma, R. A. DNA repair pathways as targets for cancer therapy, *Nat. Rev. Cancer* 2008, 8, 193-204.
(5) Zhang, J.; Yang, P. L.; Gray, N. S. Targeting cancer with small molecule kinase inhibitors, *Nat. Rev. Cancer* 2009, 9, 28-39.
(6) Aggarwal, S. Targeted cancer therapies, *Nat. Rev. Drug. Discov.* 2010, 9, 427-428.
(7) Tennant, D. A.; Duran, R. V.; Gottlieb, E. Targeting metabolic transformation for cancer therapy, *Nat. Rev. Cancer* 2010, 10, 267-277.
(8) Imai, K.; Takaoka, A. Comparing antibody and small-molecule therapies for cancer, *Nat. Rev. Cancer* 2006, 6, 714-727.
(9) Weiner, L. M.; Surana, R.; Wang, S. Monoclonal antibodies: versatile platforms for cancer immunotherapy, *Nat. Rev. Immunol.* 2010, 10, 317-327.
(10) Reichert, J. M. Antibody-based therapeutics to watch in 2011, *MAbs* 2011, 3, 76-99.
(11) Murphy, K. P.; Travers, P.; Walport, M.; Janeway, C. *Janeway's Immunobiology*; Garland Science: New York, 2008.
(12) Trail, P. A.; Willner, D.; Lasch, S. J.; Henderson, A. J.; Hofstead, S.; Casazza, A. M.; Firestone, R. A.; Hellstrom, I.; Hellstrom, K. E. Cure of xenografted human carcinomas by BR96-doxorubicin immunoconjugates, *Science* 1993, 261, 212-215.
(13) Alley, S. C.; Okeley, N. M.; Senter, P. D. Antibody-drug conjugates: targeted drug delivery for cancer, *Curr. Opin. Chem. Biol.* 2010, 14, 529-537.
(14) Ducry, L.; Stump, B. Antibody-drug conjugates: linking cytotoxic payloads to monoclonal antibodies, *Bioconjug. Chem.* 2010, 21, 5-13.
(15) Casi, G.; Neri, D. Antibody-drug conjugates: basic concepts, examples and future perspectives, *J. Control. Release* 2012, 161, 422-428.
(16) Adair, J. R.; Howard, P. W.; Hartley, J. A.; Williams, D. G.; Chester, K. A. Antibody-drug conjugates—a perfect synergy, *Expert Opin. Biol. Ther.* 2012, 12, 1191-1206.
(17) Carter, P. J. Potent antibody therapeutics by design, *Nat. Rev. Immunol.* 2006, 6, 343-357.
(18) Teicher, B. A. Antibody-drug conjugate targets, *Curr. Cancer Drug Targets* 2009, 9, 982-1004.
(19) Doronina, S. O.; Toki, B. E.; Torgov, M. Y.; Mendelsohn, B. A.; Cerveny, C. G.; Chace, D. F.; DeBlanc, R. L.; Gearing, R. P.; Bovee, T. D.; Siegall, C. B.; Francisco, J. A.; Wahl, A. F.; Meyer, D. L.; Senter, P. D. Development of potent monoclonal antibody auristatin conjugates for cancer therapy, *Nat. Biotechnol.* 2003, 21, 778-784.
(20) Widdison, W. C.; Wilhelm, S. D.; Cavanagh, E. E.; Whiteman, K. R.; Leece, B. A.; Kovtun, Y.; Goldmacher, V. S.; Xie, H.; Steeves, R. M.; Lutz, R. J.; Zhao, R.; Wang, L.; Blattler, W. A.; Chari, R. V. Semisynthetic maytansine analogues for the targeted treatment of cancer, *J. Med. Chem.* 2006, 49, 4392-4408.
(21) Hartley, J. A. The development of pyrrolobenzodiazepines as antitumour agents, *Expert Opin. Investig. Drugs* 2011, 20, 733-744.
(22) Doronina, S. O.; Mendelsohn, B. A.; Bovee, T. D.; Cerveny, C. G.; Alley, S. C.; Meyer, D. L.; Oflazoglu, E.; Toki, B. E.; Sanderson, R. J.; Zabinski, R. F.; Wahl, A. F.; Senter, P. D. Enhanced activity of monomethylauristatin F through monoclonal antibody delivery: effects of linker technology on efficacy and toxicity, *Bioconjug. Chem.* 2006, 17, 114-124.

(23) Dosio, F.; Brusa, P.; Cattel, L. Immunotoxins and Anticancer Drug Conjugate Assemblies: The Role of the Linkage between Components, *Toxins (Basel)* 2011, 3, 848-883.

(24) Wu, A. M.; Senter, P. D. Arming antibodies: prospects and challenges for immunoconjugates, *Nat. Biotechnol.* 2005, 23, 1137-1146.

(25) Ansell, S. M. Brentuximab vedotin: delivering an antimitotic drug to activated lymphoma cells, *Expert Opin. Investig. Drugs* 2011, 20, 99-105.

(26) Katz, J.; Janik, J. E.; Younes, A. Brentuximab Vedotin (SGN-35), *Clin. Cancer Res.* 2011, 17, 6428-6436.

(27) Hamann, P. R.; Hinman, L. M.; Hollander, I.; Beyer, C. F.; Lindh, D.; Holcomb, R.; Hallett, W.; Tsou, H. R.; Upeslacis, J.; Shochat, D.; Mountain, A.; Flowers, D. A.; Bernstein, I. Gemtuzumab ozogamicin, a potent and selective anti-CD33 antibody-calicheamicin conjugate for treatment of acute myeloid leukemia, *Bioconjug. Chem.* 2002, 13, 47-58.

(28) Hutter, M. L.; Schlenk, R. F. Gemtuzumab ozogamicin in non-acute promyelocytic acute myeloid leukemia, *Expert Opin. Biol. Ther.* 2011, 11, 1369-1380.

(29) Remillard, S.; Rebhun, L. I.; Howie, G. A.; Kupchan, S. M. Antimitotic activity of the potent tumor inhibitor maytansine, *Science* 1975, 189, 1002-1005.

(30) Goldberg, R. M. Cetuximab, *Nat. Rev. Drug Discov.* 2005, Suppl, S10-11.

(31) Kabolizadeh, P.; Kubicek, G. J.; Heron, D. E.; Ferris, R. L.; Gibson, M. K. The role of cetuximab in the management of head and neck cancers, *Expert Opin. Biol. Ther.* 2012, 12, 517-528.

(32) Broadbridge, V. T.; Karapetis, C. S.; Price, T. J. Cetuximab in metastatic colorectal cancer, Expert Rev. *Anticancer Ther.* 2012, 12, 555-565.

(33) Arteaga, C. L. Overview of epidermal growth factor receptor biology and its role as a therapeutic target in human neoplasia, *Semin. Oncol.* 2002, 29, 3-9.

(34) Mendelsohn, J.; Baselga, J. Status of epidermal growth factor receptor antagonists in the biology and treatment of cancer, *J. Clin. Oncol.* 2003, 21, 2787-2799.

(35) Krause, D. S.; Van Etten, R. A. Tyrosine kinases as targets for cancer therapy, *N. Engl. J. Med.* 2005, 353, 172-187.

(36) Goldstein, N. I.; Prewett, M.; Zuklys, K.; Rockwell, P.; Mendelsohn, J. Biological efficacy of a chimeric antibody to the epidermal growth factor receptor in a human tumor xenograft model, *Clin. Cancer Res.* 1995, 1, 1311-1318.

(37) Hamann, P. R.; Hinman, L. M.; Beyer, C. F.; Lindh, D.; Upeslacis, J.; Flowers, D. A.; Bernstein, I. An anti-CD33 antibody-calicheamicin conjugate for treatment of acute myeloid leukemia. Choice of linker, *Bioconjug. Chem.* 2002, 13, 40-46.

(38) van Der Velden, V. H.; te Marvelde, J. G.; Hoogeveen, P. G.; Bernstein, I. D.; Houtsmuller, A. B.; Berger, M. S.; van Dongen, J. J. Targeting of the CD33-calicheamicin immunoconjugate Mylotarg (CMA-676) in acute myeloid leukemia: in vivo and in vitro saturation and internalization by leukemic and normal myeloid cells, *Blood* 2001, 97, 3197-3204.

(39) Ojima, I.; Geng, X.; Wu, X.; Qu, C.; Borella, C. P.; Xie, H.; Wilhelm, S. D.; Leece, B. A.; Bartle, L. M.; Goldmacher, V. S.; Chari, R. V. Tumor-specific novel taxoid-monoclonal antibody conjugates, *J. Med. Chem.* 2002, 45, 5620-5623.

(40) Erickson, H. K.; Park, P. U.; Widdison, W. C.; Kovtun, Y. V.; Garrett, L. M.; Hoffman, K.; Lutz, R. J.; Goldmacher, V. S.; Blattler, W. A. Antibody-maytansinoid conjugates are activated in targeted cancer cells by lysosomal degradation and linker-dependent intracellular processing, *Cancer Res.* 2006, 66, 4426-4433.

(41) Lewis Phillips, G. D.; Li, G.; Dugger, D. L.; Crocker, L. M.; Parsons, K. L.; Mai, E.; Blattler, W. A.; Lambert, J. M.; Chari, R. V.; Lutz, R. J.; Wong, W. L.; Jacobson, F. S.; Koeppen, H.; Schwall, R. H.; Kenkare-Mitra, S. R.; Spencer, S. D.; Sliwkowski, M. X. Targeting HER2-positive breast cancer with trastuzumab-DM1, an antibody-cytotoxic drug conjugate, *Cancer Res.* 2008, 68, 9280-9290.

(42) Kellogg, B. A.; Garrett, L.; Kovtun, Y.; Lai, K. C.; Leece, B.; Miller, M.; Payne, G.; Steeves, R.; Whiteman, K. R.; Widdison, W.; Xie, H.; Singh, R.; Chari, R. V.; Lambert, J. M.; Lutz, R. J. Disulfide-linked antibody-maytansinoid conjugates: optimization of in vivo activity by varying the steric hindrance at carbon atoms adjacent to the disulfide linkage, *Bioconjug. Chem.* 2011, 22, 717-727.

(43) Dubowchik, G. M.; Mosure, K.; Knipe, J. O.; Firestone, R. A. Cathepsin B-sensitive dipeptide prodrugs. 2. Models of anticancer drugs paclitaxel (Taxol), mitomycin C and doxorubicin, *Bioorg. Med. Chem. Lett.* 1998, 8, 3347-3352.

(44) Francisco, J. A.; Cerveny, C. G.; Meyer, D. L.; Mixan, B. J.; Klussman, K.; Chace, D. F.; Rejniak, S. X.; Gordon, K. A.; DeBlanc, R.; Toki, B. E.; Law, C. L.; Doronina, S. O.; Siegall, C. B.; Senter, P. D.; Wahl, A. F. cAC10-vcMMAE, an anti-CD30-monomethyl auristatin E conjugate with potent and selective antitumor activity, *Blood* 2003, 102, 1458-1465.

(45) Sanderson, R. J.; Hering, M. A.; James, S. F.; Sun, M. M.; Doronina, S. O.; Siadak, A. W.; Senter, P. D.; Wahl, A. F. In vivo drug-linker stability of an anti-CD30 dipeptide-linked auristatin immunoconjugate, Clin. *Cancer Res.* 2005, 11, 843-852.

(46) DiJoseph, J. F.; Dougher, M. M.; Evans, D. Y.; Zhou, B. B.; Damle, N. K. Preclinical anti-tumor activity of antibody-targeted chemotherapy with CMC-544 (inotuzumab ozogamicin), a CD22-specific immunoconjugate of calicheamicin, compared with non-targeted combination chemotherapy with CVP or CHOP, *Cancer Chemother. Pharmacol.* 2011, 67, 741-749.

(47) Toki, B. E.; Cerveny, C. G.; Wahl, A. F.; Senter, P. D. Protease-mediated fragmentation of p-amidobenzyl ethers: a new strategy for the activation of anticancer prodrugs, *J. Org. Chem.* 2002, 67, 1866-1872.

(48) Kovtun, Y. V.; Audette, C. A.; Ye, Y.; Xie, H.; Ruberti, M. F.; Phinney, S. J.; Leece, B. A.; Chittenden, T.; Blattler, W. A.; Goldmacher, V. S. Antibody-drug conjugates designed to eradicate tumors with homogeneous and heterogeneous expression of the target antigen, *Cancer Res.* 2006, 66, 3214-3221.

(49) a. Dugger, R. B.; LeTendre, L. J.; Patel, V. B.; Prashad, A. S. and Zhang, C. Intermediates and methods for synthesizing Calicheamicin derivatives. WO 2015/063680 A1.
  b. Moran, J. K. and G, J. Processes for the convergent synthesis of Calicheamicin derivatives. US 2009/0312530 A1.
  c. Chiarello, G. A. and Sahli, A. Improved processes for making hydrazides. WO 2008/147765 A1.

(50) Padiya, K. J.; Nair, P. S.; Pal, R. R.; Chaure, G. S.; Gudade, G. B.; Parkale, S. S.; Manojkumar, V. L.; Swapnil, R. B.; Smita, A. B.; Sachin, D. S.; Palle, V. P. and Kamboj, R. K. Spirocyclic compounds as voltage-gated sodium channel modulators. WO 2012/049555 A1

The invention claimed is:

1. A compound of Formula (I) or a pharmaceutically acceptable salt or solvate thereof:

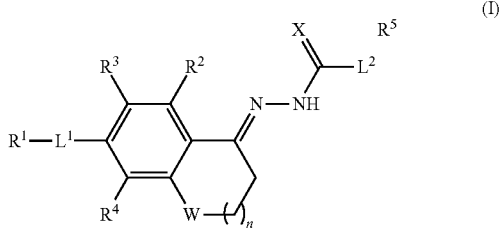

wherein:
R$^1$ and R$^5$ are independently a reactive functional group selected from a Michael addition acceptor, C$_{2-6}$alkenyl, C$_{2-6}$alkynyl, OH,

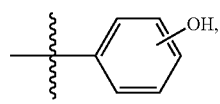

OC$_{1-6}$alkyl, halo, C(O)H, C(O)C$_{1-6}$alkyl, COOH, COOC$_{1-6}$alkyl, NH$_2$, NHC$_{1-6}$alkyl, N(C$_{1-6}$alkyl)$_2$, SH, SC$_{1-6}$alkyl, C(O)NH$_2$, C(O)NHC$_{1-6}$alkyl, C(O)N(C$_{1-6}$alkyl)$_2$, OCN, NCO, SCN, NCS, NHNH$_2$, C=NNH$_2$, C(O)NHNH$_2$, C=N$_2$, NO$_2$, CN, S—S(C$_{1-6}$alkyl), S(O)C$_{1-6}$alkyl, SO$_2$C$_{1-6}$alkyl, SO$_2$H, S(O)OH, C(O)OC(O)C$_{1-6}$alkyl, S(O)H, N≡C, C(O)NHC(O)C$_{1-6}$alkyl, C(NH)OC$_{1-6}$alkyl, NHOH, C=(NOH)H, C(NOH)alkyl, C(O)NHOH, C(S)NHOH, C(OC$_{1-6}$alkyl)$_3$,

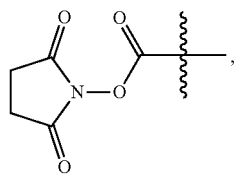 [SMILES: *C(=O)ON1C(=O)CCC1=O]

NHC(O)NH$_2$, NHC(O)NHNH$_2$, OC(O)NH$_2$, OC(O)NHC$_{1-6}$alkyl, OC(O)N(C$_{1-6}$alkyl)$_2$, C(NH)C$_{1-6}$alkyl, N$_3$, and N=NC$_{1-6}$alkyl,
R$^2$ is selected from H, halo, C$_{1-6}$alkyl, C$_{1-6}$fluoroalkyl, OR$^6$, SR$^6$ and NR$^6$R$^7$;
R$^3$ and R$^4$ are independently selected from H, CN, NO$_2$, halo, C$_{1-6}$alkyl, C$_{1-6}$fluoroalkyl, OR$^8$, SR$^8$ and NR$^8$R$^9$;
X is selected from O, S and NR$^{10}$;
W is selected from O, NR$^{11}$, S, and S(O)$_2$;
R$^6$, R$^7$, R$^8$, R$^9$, R$^{10}$, and R$^{11}$ are independently selected from H, C$_{1-6}$alkyl and C$_{1-6}$fluoroalkyl;
L$^1$ and L$^2$ are independently a linker moiety selected from Z, R$^a$, Z—R$^a$, R$^a$—Z, R$^a$—Z—R$^b$ and Z—R$^a$—Z$^a$, wherein Z and Z$^a$ are independently selected from O, S, S(O), SO$_2$, NH, N(C$_{1-6}$alkyl), C(Q), C(Q)Y, YC(Q), YC(Q)Y$^a$, (YC$_{1-6}$alkylene)$_p$, (C$_{1-6}$alkyleneY)$_p$ and Y—(C$_{1-6}$alkyleneY)$_p$, wherein R$^a$ and R$^b$ are independently selected from C$_{1-10}$alkylene, C$_{2-10}$alkenylene and C$_{2-10}$alkynylene; Q, Y and Y$^a$ are independently selected from O, S, NH and N(C$_{1-6}$alkyl); and p is selected from 1, 2, 3, 4, 5 and 6; and
n is 0, 1, 2 or 3.

2. The compound of claim 1, wherein R$^1$ and R$^5$ have different reactivities so that one of R$^1$ and R$^5$ is functionalized by reaction with a complementary functional group in the presence of the other of R$^1$ and R$^5$, and without the other of R$^1$ and R$^5$ participating in the reaction.

3. The compound of claim 1, wherein the compound has the following structure:

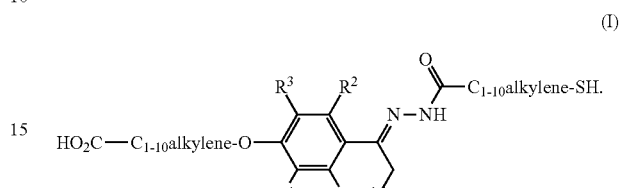

4. The compound of claim 1, wherein the compound has the following structure:

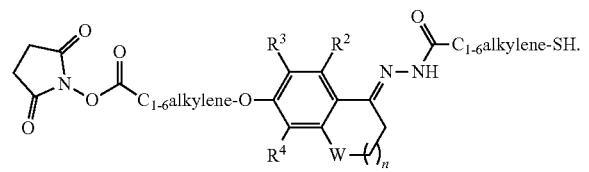

5. The compound of claim 1, wherein the compound is selected from

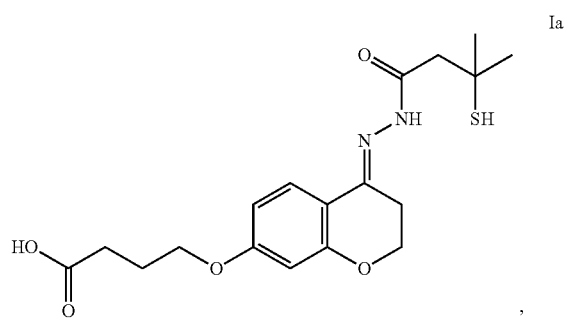

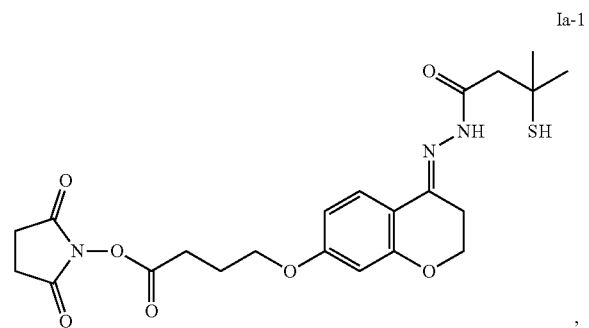

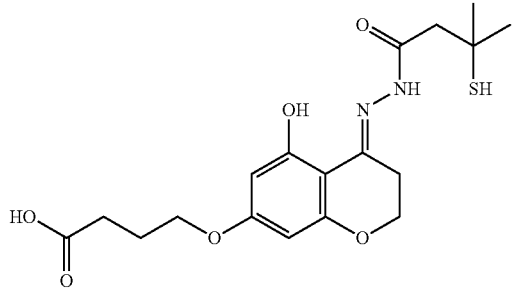

Ib

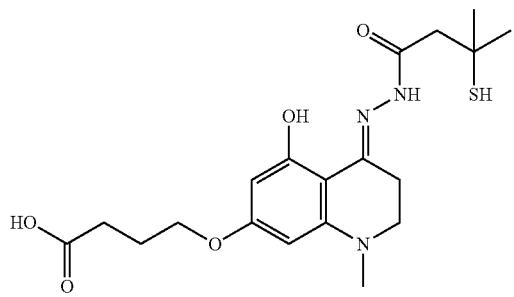

Ic

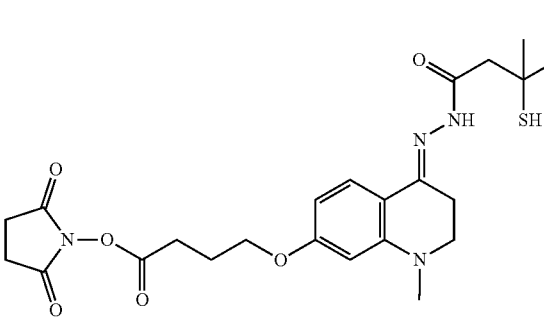

Ic-1

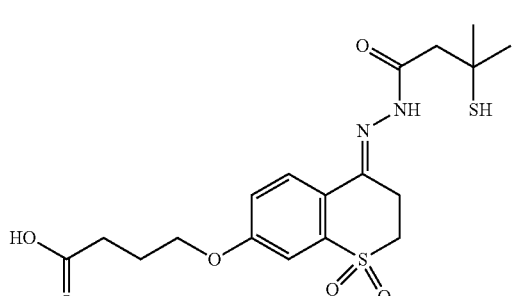

Id

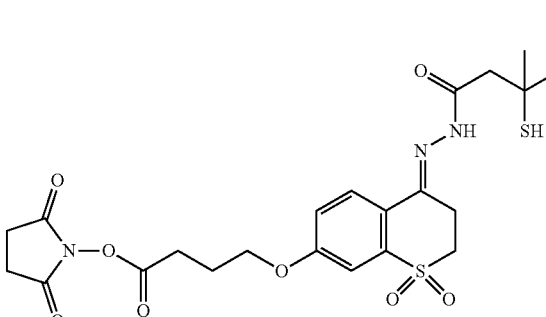

Id-1

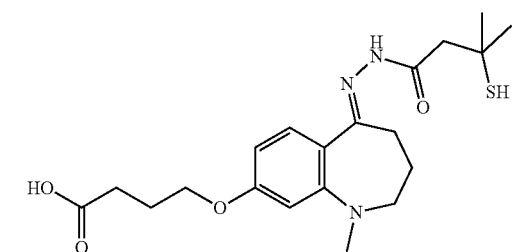

If

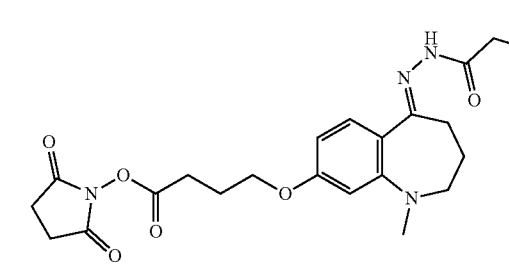

If-1

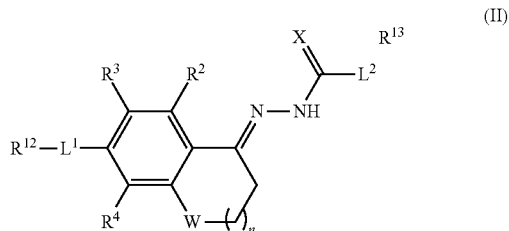

or a pharmaceutically acceptable salt or solvate thereof.

6. A compound of Formula (II) or a pharmaceutically acceptable salt or solvate thereof:

$$\text{(II)}$$

wherein:
$R^2$ is selected from H, halo, $C_{1-6}$alkyl, $C_{1-6}$fluoroalkyl, $OR^6$, $SR^7$ and $NR^8R^9$;
$R^3$ and $R^4$ are independently selected from H, CN, $NO_2$, halo, $C_{1-6}$alkyl, $C_{1-6}$fluoroalkyl, $OR^6$, $SR^7$ and $NR^8R^9$;
X is selected from O, S and $NR^{19}$;
W is selected from O, $NR^{11}$, S, and $S(O)_2$;
$R^6$, $R^7$, $R^8$, $R^9$, $R^{10}$, and $R^{11}$ are independently selected from H, $C_{1-6}$alkyl and $C_{1-6}$fluoroalkyl;
$L^1$ and $L^2$ are independently a linker moiety selected from $R^a$, $Z-R^a$, $R^a-Z$, $R^a-Z-R^b$ and $Z-R^a-Z^a$, wherein Z and $Z^a$ are independently selected from O, S, S(O), $SO_2$, NH, $N(C_{1-6}$alkyl), C(Q), C(Q)Y, YC(Q), YC(Q)$Y^a$, $(YC_{1-6}$alkylene$)_p$, $(C_{1-6}$alkyleneY$)_p$ and Y—$(C_{1-6}$alkyleneY$)_p$, wherein $R^a$ and $R^b$ are independently selected from $C_{1-10}$alkylene, $C_{2-10}$alkenylene and $C_{2-10}$alkynylene; Q, Y and $Y^a$ are independently selected from O, S, NH and N($C_{1-6}$alkyl); and p is selected from 1, 2, 3, 4, 5 and 6;
n is 0, 1, 2 or 3; and
$R^{12}$ and $R^{13}$ are different and are independently selected from a fluorescent dye, drug, antibody, nucleic acid, peptide, radiolabel, PET label, nanoparticle, metal complex.

7. The compound of claim 6, wherein the compound has the following structure:

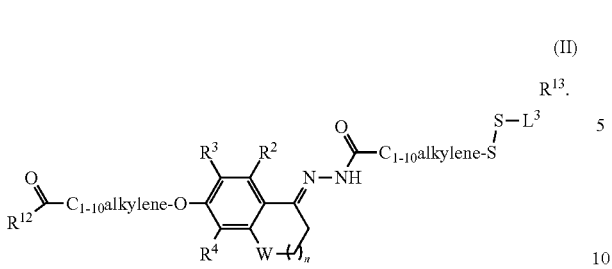

(II)

8. The compound of claim 7, wherein $R^{12}$ and $R^{13}$ are different and are independently selected from an antibody and drug.

9. A compound of Formula IV or a pharmaceutically acceptable salt or solvate thereof:

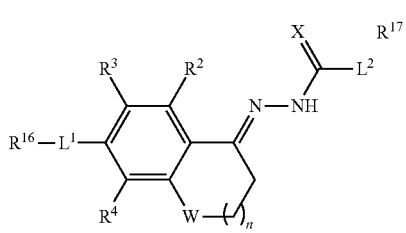

(IV)

wherein $R^2$ is selected from H, halo, $C_{1-6}$alkyl, $C_{1-6}$fluoroalkyl, $OR^6$, $SR^7$ and $NR^8R^9$;

$R^3$ and $R^4$ are independently selected from H, CN, $NO_2$, halo, $C_{1-6}$alkyl, $C_{1-6}$fluoroalkyl, $OR^6$, $SR^7$ and $NR^8R^9$;

X is selected from O, S and $NR^{10}$;

W is selected from O, $NR^{11}$, S, and $S(O)_2$;

$R^6$, $R^7$, $R^8$, $R^9$, $R^{10}$, and $R^{11}$ are independently selected from H, $C_{1-6}$alkyl and $C_{1-6}$fluoroalkyl;

$L^1$ and $L^2$ are independently a linker moiety selected from Z, $R^a$, Z—$R^a$, $R^a$—Z, $R^a$—Z—$R^b$ and Z—$R^a$—$Z^a$, wherein Z and $Z^a$ are independently selected from O, S, S(O), $SO_2$, NH, N($C_{1-6}$alkyl), C(Q), C(Q)Y, YC(Q), YC(Q)$Y^a$, (YC$_{1-6}$alkylene)$_p$, ($C_{1-6}$alkyleneY)$_p$ and Y—($C_{1-6}$alkyleneY)$_p$, wherein $R^a$ and $R^b$ are independently selected from $C_{1-10}$alkylene, $C_{1-10}$alkenylene and $C_{2-10}$alkynylene; Q, Y and $Y^a$ are independently selected from O, S, NH and N($C_{1-6}$alkyl); and p is selected from 1, 2, 3, 4, 5 and 6;

n is 0, 1, 2 or 3; and one of $R^{16}$ and $R^{17}$ is a reactive functional group selected a Michael addition acceptor, $C_{2-6}$alkenyl, $C_{2-6}$alkynyl, OH,

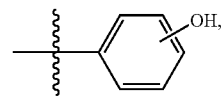

$OC_{1-6}$alkyl, halo, C(O)H, C(O)$C_{1-6}$alkyl, COOH, COOC$_{1-6}$alkyl, $NH_2$, NHC$_{1-6}$alkyl, N($C_{1-6}$alkyl)$_2$, SH, SC$_{1-6}$alkyl, C(O)$NH_2$, C(O)NHC$_{1-6}$alkyl, C(O)N($C_{1-6}$alkyl)$_2$, OCN, NCO, SCN, NCS, $NHNH_2$, C=$NNH_2$, C(O)$NHNH_2$, C=$N_2$, $NO_2$, CN, S—S($C_{1-6}$alkyl), S(O)$C_{1-6}$alkyl, $SO_2C_{1-6}$alkyl, $SO_2H$, S(O)OH, C(O)OC(O)$C_{1-6}$alkyl, S(O)H, N≡C, C(O)NHC(O)$C_{1-6}$alkyl, C(NH)OC$_{1-6}$alkyl, NHOH, C=(NOH)H, C(NOH)alkyl, C(O)NHOH, C(S)NHOH, C(OC$_{1-6}$alkyl)$_3$,

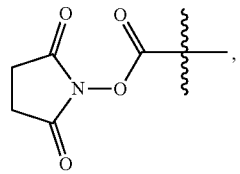 [SMILES: *C(=O)ON1C(=O)CCC1=O]

$NHC(O)NH_2$, $NHC(O)NHNH_2$, $OC(O)NH_2$, OC(O)NHC$_{1-6}$alkyl, OC(O)N($C_{1-6}$alkyl)$_2$, C(NH)$C_{1-6}$alkyl, $N_3$, and N=NC$_{1-6}$alkyl, and the other of $R^{16}$ and $R^{17}$ is selected from a fluorescent dye, drug, antibody, nucleic acid, peptide, radiolabel, PET label, nanoparticle, and metal complex.

10. The compound of claim 9, wherein the compound is selected from

IVa

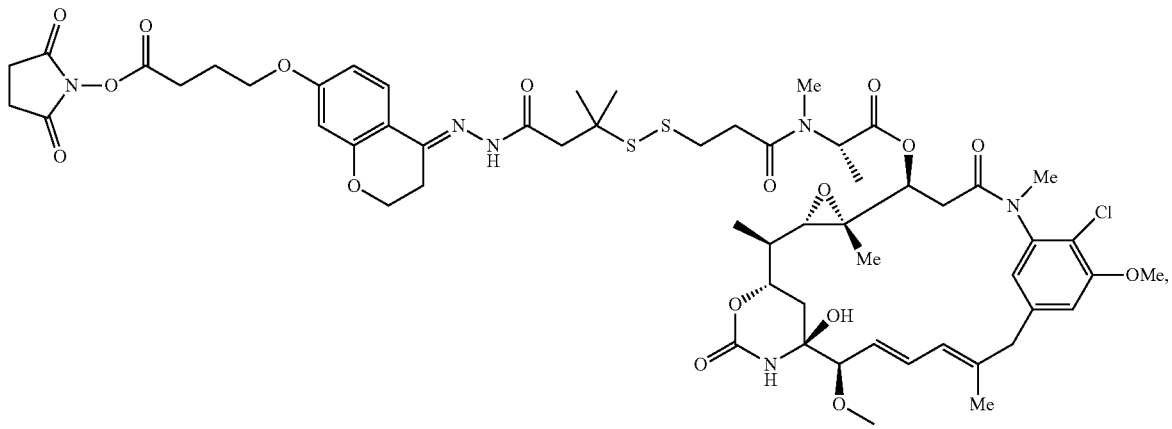

-continued
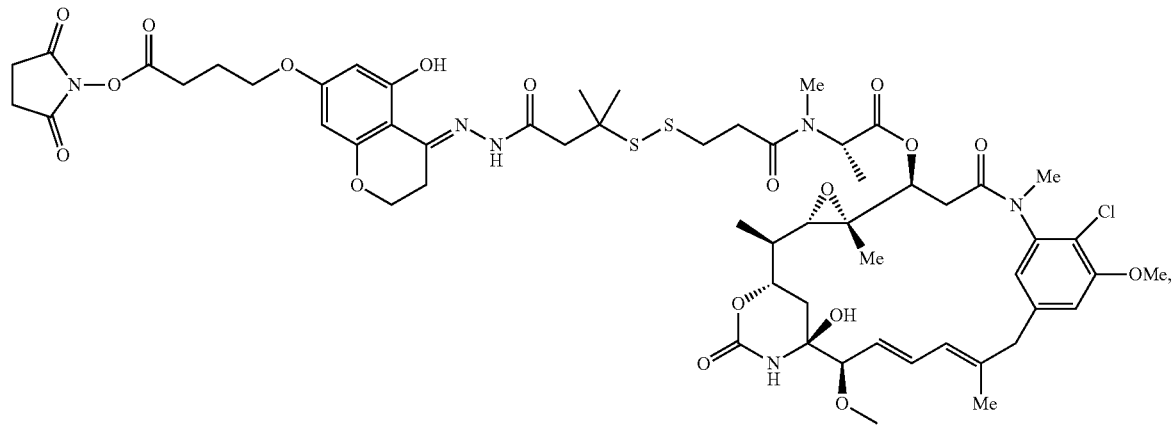
IVb
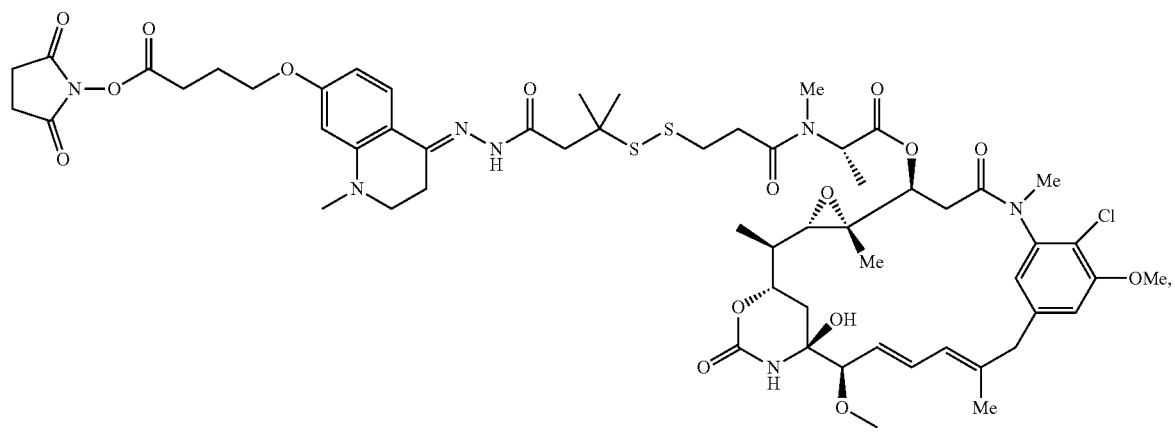
IVc
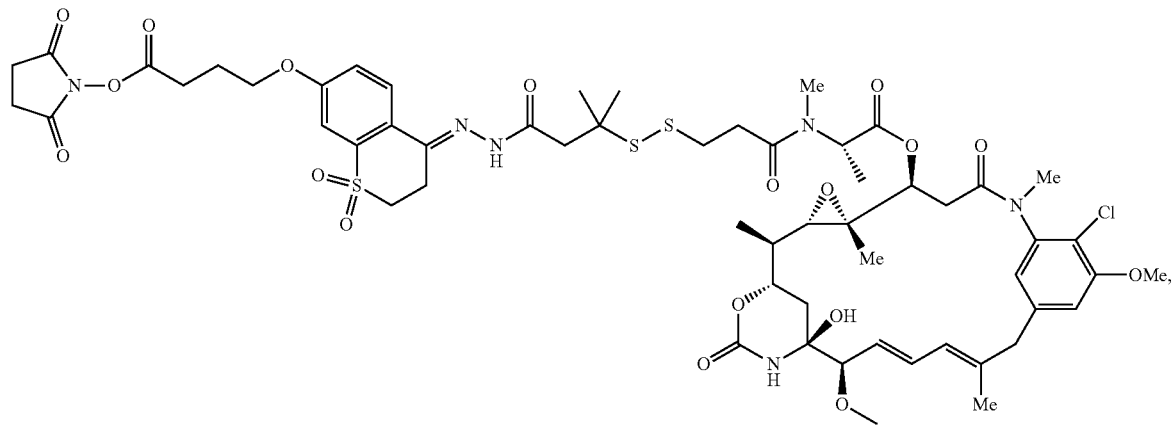
IVd

-continued
IVf
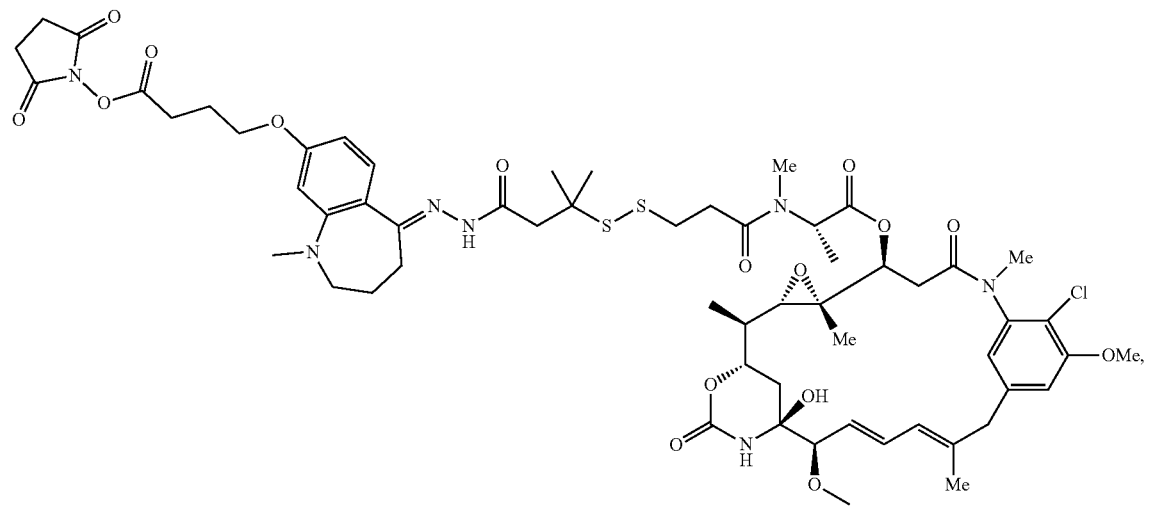
IVg
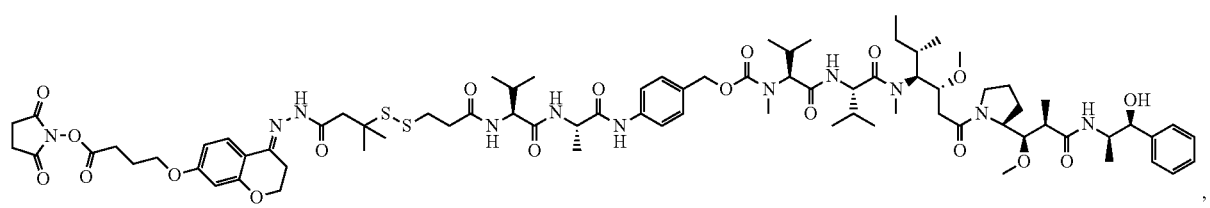
IVh
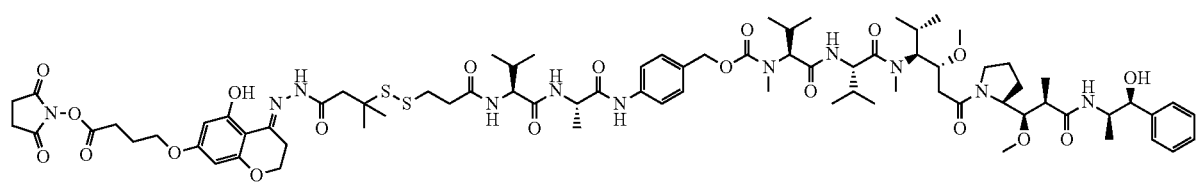
IVi
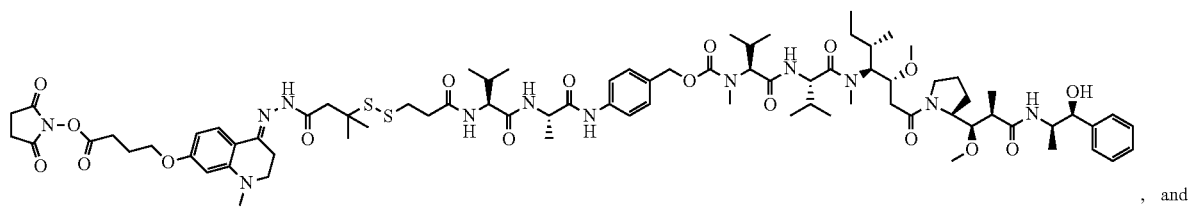
, and
IVj
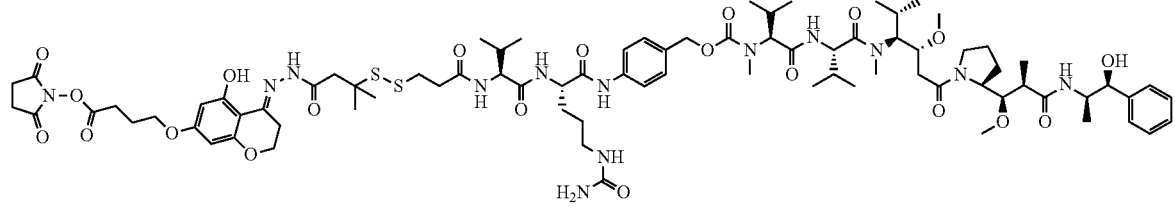
or a pharmaceutically acceptable salt or solvate thereof.

11. An antibody-drug conjugate comprising an antibody covalently attached by a linker to one or more drugs, the conjugate having a Formula (III):

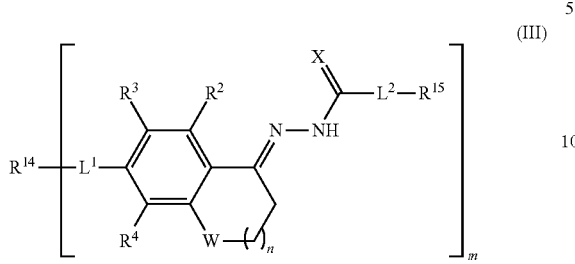

or a pharmaceutically acceptable salt or solvate thereof, wherein $R^{14}$ is an antibody;
$R^{15}$ is a drug;
$L^1$ and $L^2$ are independently a linker moiety selected from $R^a$, $Z$—$R^a$, $R^a$—$Z$, $R^a$—$Z$—$R^b$ and $Z$—$R^a$—$Z^a$, wherein Z and $Z^a$ are independently selected from O, S, S(O), $SO_2$, NH, $N(C_{1-6}alkyl)$, C(Q), C(Q)Y, YC(Q), $YC(Q)Y^a$, $(YC_{1-6}alkylene)_p$, $(C_{1-6}alkyleneY)_p$ and $Y$—$(C_{1-6}alkyleneY)_p$, wherein $R^a$ and $R^b$ are independently selected from $C_{1-10}$alkylene, $C_{2-10}$alkenylene and $C_{2-10}$alkynylene; Q, Y and $Y^a$ are independently selected from O, S, NH and $N(C_{1-6}alkyl)$; and p is selected from 1, 2, 3, 4, 5 and 6;

$R^2$ is selected from H, halo, $C_{1-6}$alkyl, $C_{1-6}$fluoroalkyl, $OR^6$, $SR^7$ and $NR^8R^9$;

$R^3$ and $R^4$ are independently selected from H, CN, $NO_2$, halo, $C_{1-6}$alkyl, $C_{1-6}$fluoroalkyl, $OR^6$, $SR^7$ and $NR^8R^9$;

W is selected from O, $NR^{11}$, S, and $S(O)_2$;

$R^6$, $R^7$, $R^8$, $R^9$, and $R^{11}$ are independently selected from H, $C_{1-6}$alkyl and $C_{1-6}$fluoroalkyl;

n is 0, 1, 2 or 3;

and m is an integer from 1 to 20.

12. The antibody-drug conjugate of claim 10, wherein the antibody-drug conjugate is selected from

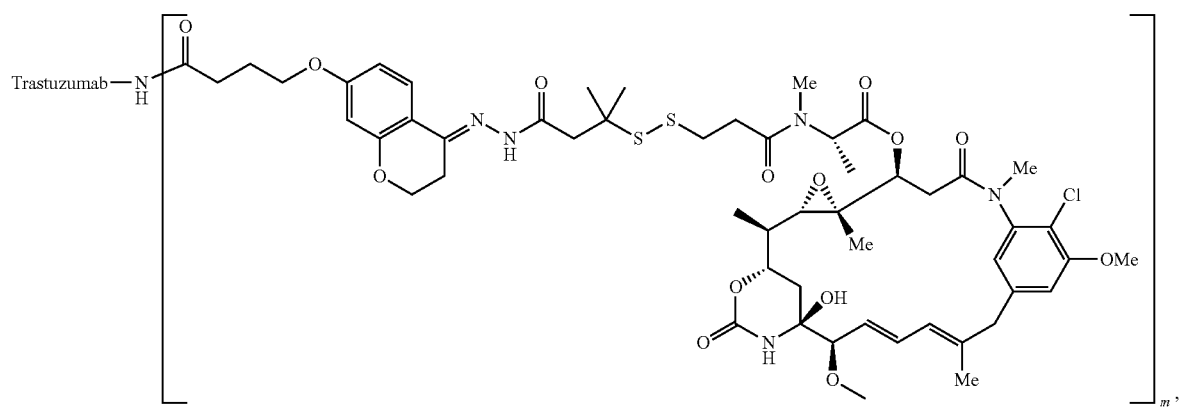

IIIa

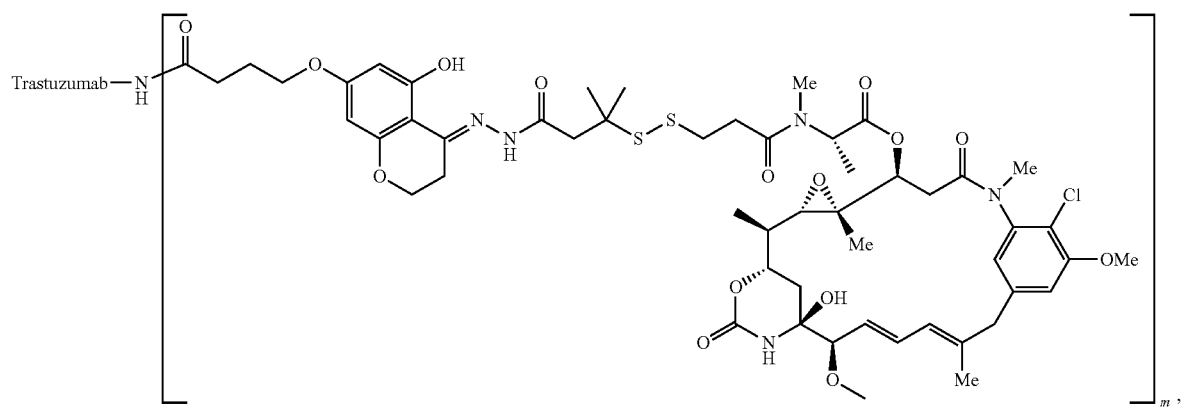

IIIb

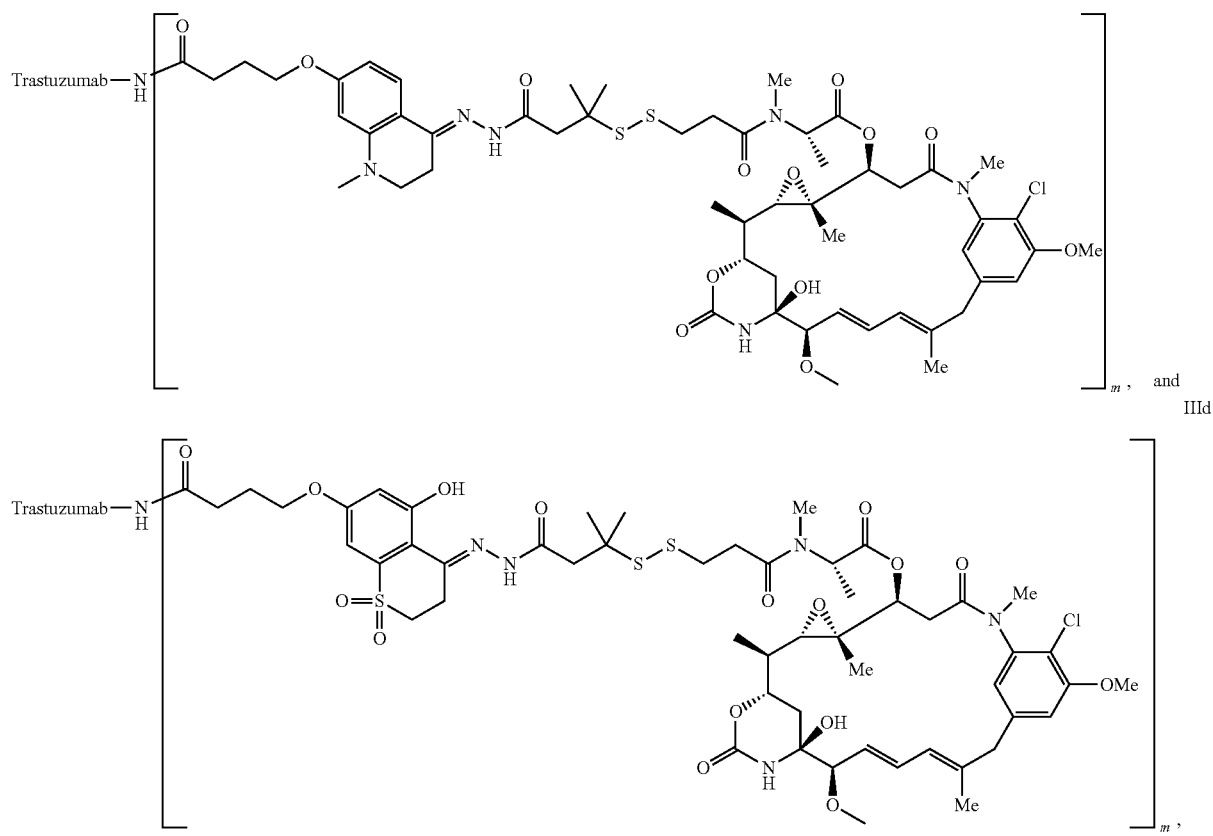

or pharmaceutically acceptable salt or solvate thereof.

13. A pharmaceutical composition comprising one or more compounds of Formula (III) of claim 11, or a pharmaceutically acceptable salt thereof, and a pharmaceutically acceptable carrier and/or diluent.

14. A method of preparing an ADC of Formula (III) of claim comprising:

(a) reacting a compound of Formula (I):

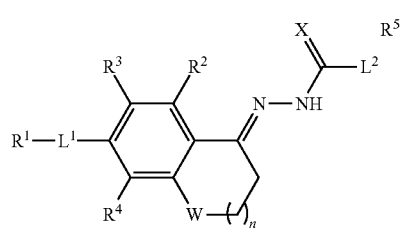

wherein:

$R^1$ and $R^5$ are independently a reactive functional group selected from a Michael addition acceptor, $C_{2-6}$alkenyl, $C_{2-6}$alkynyl, OH,

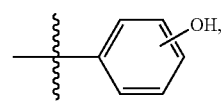

$OC_{1-6}$alkyl, halo, C(O)H, C(O)$C_{1-6}$alkyl, COOH, COO$C_{1-6}$alkyl, $NH_2$, NH$C_{1-6}$alkyl, N($C_{1-6}$alkyl)$_2$, SH, S$C_{1-6}$alkyl, C(O)$NH_2$, C(O)NH$C_{1-6}$alkyl, C(O)N($C_{1-6}$alkyl)$_2$, OCN, NCO, SCN, NCS, NHNH$_2$, C=NNH$_2$, C(O)NHNH$_2$, C=N$_2$, NO$_2$, CN, S—S($C_{1-6}$alkyl), S(O)$C_{1-6}$alkyl, SO$_2$$C_{1-6}$alkyl, SO$_2$H, S(O)OH, C(O)OC(O)$C_{1-6}$alkyl, S(O)H, N≡C, C(O)NHC(O)$C_{1-6}$alkyl, C(NH)O$C_{1-6}$alkyl, NHOH, C=(NOH)H, C(NOH)alkyl, C(O)NHOH, C(S)NHOH, C(O$C_{1-6}$alkyl)$_3$,

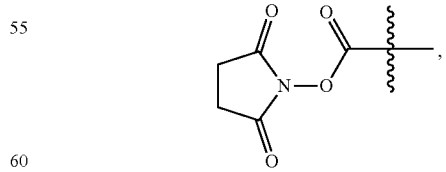

NHC(O)$NH_2$, NHC(O)NHNH$_2$, OC(O)$NH_2$, OC(O)NH$C_{1-6}$alkyl, OC(O)N($C_{1-6}$alkyl)$_2$, C(NH)$C_{1-6}$alkyl, N$_3$, and N=N$C_{1-6}$alkyl, $R^2$ is selected from H, halo, $C_{1-6}$alkyl, $C_{1-6}$fluoroalkyl, $OR^6$, $SR^6$ and $NR^6R^7$;

$R^3$ and $R^4$ are independently selected from H, CN, $NO_2$, halo, $C_{1-6}$alkyl, $C_{1-6}$fluoroalkyl, $OR^8$, $SR^8$ and $NR^8R^9$;

X is selected from O, S and $NR^{19}$;

W is selected from O, $NR^{11}$, S, and $S(O)_2$;

$R^6$, $R^7$, $R^8$, $R^9$, $R^{19}$, and $R^{11}$ are independently selected from H, $C_{1-6}$alkyl and $C_{1-6}$fluoroalkyl;

$L^1$ and $L^2$ are independently a linker moiety selected from Z, $R^a$, Z—$R^a$, $R^a$—Z, $R^a$—Z—$R^b$ and Z—$R^a$—$Z^a$, wherein Z and $Z^a$ are independently selected from O, S, S(O), $SO_2$, NH, N($C_{1-6}$alkyl), C(Q), C(Q)Y, YC(Q), YC(Q)$Y^a$, (YC$_{1-6}$alkylene)$_p$, (C$_{1-6}$alkyleneY)$_p$ and Y—(C$_{1-6}$alkyleneY)$_p$, wherein $R^a$ and $R^b$ are independently selected from $C_{1-10}$alkylene, $C_{2-10}$alkenylene and $C_{2-10}$alkynylene; Q, Y and $Y^a$ are independently selected from O, S, NH and N($C_{1-6}$alkyl); and p is selected from 1, 2, 3, 4, 5 and 6; and n is 0, 1, 2 or 3, with a drug to provide a Formula (I)-drug conjugate;

(b) reacting the Formula (I)-drug conjugate with an antibody to provide the ADC of Formula (III); and optionally (c) purifying the ADC of Formula (III).

15. The compound of claim 1, wherein the reactive functional groups of $R^1$ and $R^5$ are selected from

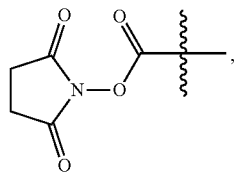 [SMILES: *C(=O)ON1C(=O)CCC1=O]

Michael addition acceptors, $NH_2$, $NHC_{1-6}$alkyl, $N(C_{1-6}$alkyl$)_2$, and SH.

16. The compound of claim 1, wherein X is O.

17. The compound of claim 1, wherein n is 1.

18. The compound of claim 1, wherein $L^1$ is selected from $OC(O)C_{1-10}$alkyleneO, $NHC(O)C_{1-10}$alkyleneO, $C_{1-6}$alkyleneO, $OC(O)C_{1-10}$alkyleneNH, $NHC(O)C_{1-10}$alkyleneNH, $C_{1-6}$alkyleneNH, $C(O)C_{1-10}$alkyleneO and $C(O)C_{1-10}$alkyleneNH, and wherein $L^2$ is selected from $C_{1-10}$alkyleneS and $C_{1-10}$alkylene.

19. The compound of claim 1, wherein $R^1$ and $R^5$ are independently a reactive functional group selected from a Michael addition acceptor, $C_{2-4}$alkenyl, $C_{2-4}$alkynyl, OH,

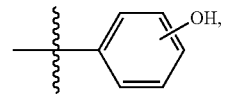

$OC_{1-4}$alkyl, halo, C(O)H, $C(O)C_{1-4}$alkyl, COOH, $COOC_{1-4}$alkyl, $NH_2$, $NHC_{1-4}$alkyl, $N(C_{1-4}$alkyl$)_2$, SH, $SC_{1-4}$alkyl, $C(O)NH_2$, $C(O)NHC_{1-4}$alkyl, $C(O)N(C_{1-4}$alkyl$)_2$, OCN, NCO, SCN, NCS, $NHNH_2$, $C=NNH_2$, $C(O)NHNH_2$, $C=N_2$, $NO_2$, CN, S—$S(C_{1-4}$alkyl$)$, $S(O)C_{1-4}$alkyl, $SO_2C_{1-4}$alkyl, $SO_2H$, S(O)OH, $C(O)OC(O)C_{1-4}$alkyl, S(O)H, N≡C, $C(O)NHC(O)C_{1-4}$alkyl, $C(NH)OC_{1-4}$alkyl, NHOH, C=(NOH)H, $C(NOH)C_{1-4}$alkyl, C(O)NHOH, C(S)NHOH, $C(OC_{1-4}$alkyl$)_3$,

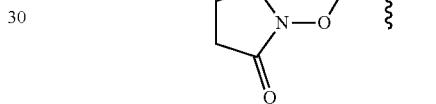

$ONHC(O)NH_2$, $NHC(O)NHNH_2$, $OC(O)NH_2$, $OC(O)NHC_{1-4}$alkyl, $OC(O)N(C_{1-4}$alkyl$)_2$, $C(NH)C_{1-4}$alkyl, $N_3$, and N=$NC_{1-4}$alkyl.

* * * * *